(12) United States Patent
Maupin-Furlow et al.

(10) Patent No.: US 8,414,660 B2
(45) Date of Patent: Apr. 9, 2013

(54) HALOFERAX VOLCANII LACCASE AND VARIANTS AND FRAGMENTS THEREOF

(75) Inventors: Julie A. Maupin-Furlow, Gainesville, FL (US); Sivakumar Uthandi, Coimbatore (IN); Boutaiba Saad, Algiers (DZ); Matthew A. Humbard, Hyattsville, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/264,165

(22) PCT Filed: May 10, 2010

(86) PCT No.: PCT/US2010/034177
§ 371 (c)(1),
(2), (4) Date: Jan. 4, 2012

(87) PCT Pub. No.: WO2010/129940
PCT Pub. Date: Nov. 11, 2010

(65) Prior Publication Data
US 2012/0094335 A1   Apr. 19, 2012

Related U.S. Application Data

(60) Provisional application No. 61/176,587, filed on May 8, 2009.

(51) Int. Cl.
*C09B 67/00* (2006.01)
*C12N 9/02* (2006.01)
*C08H 7/00* (2011.01)
*C02F 1/00* (2006.01)

(52) U.S. Cl. ............. 8/401; 435/189; 527/400; 210/632

(58) Field of Classification Search ........................ None
See application file for complete search history.

(56) References Cited

U.S. PATENT DOCUMENTS

| 6,207,430 | B1 | 3/2001 | Yaver et al. |
| 6,242,232 | B1 | 6/2001 | Yaver et al. |
| 2005/0089980 | A1 | 4/2005 | Kruus et al. |
| 2006/0063246 | A1 | 3/2006 | Paloheimo et al. |
| 2007/0105112 | A1 | 5/2007 | Hitchman et al. |

FOREIGN PATENT DOCUMENTS

WO   WO 2007/096184   8/2007

OTHER PUBLICATIONS

Uthandi et al., Appl. Environ. Microbiol. 76:733-743, Dec. 2009.*
GenBank Accession No. CP001953, Mar. 23, 2010, 174 pages.*
Written Opinion in International Application No. PCT/US2010/034177, Jan. 28, 2011, pp. 1-3.
Sakurai, T. et al. "Basic and Applied Features of Multicopper Oxidases, CueO, Bilirubin Oxidase, and Laccase" *The Chemical Record*, 2007, pp. 220-229, vol. 7.
Shleev, S. et al "Direct electron transfer between copper-containing proteins and electrodes" *Biosensors and Bioelectronics*, 2005, pp. 2517-2554, vol. 20.
Widsten, P. et al. "Adhesion improvement of lignocellulosic products by enzymatic pre-treatment" *Biotechnology Advances*, 2008, pp. 379-386, vol. 26.
Claus, H. et al. "Degradation and Transformation of Aquatic Humic Substances by Laccase-producing Fungi *Cladosporium cladosporioides* and *Polyporus versicolor*" *Acta Hydrochimica et Hydrobiologica*, 1998, pp. 180-185, vol. 26.
Fitz-Gibbon, S. T. et al. "Genome sequence of the hyperthermophilic crenarchaeon *Pyrobaculum aerophilum*" *Proceedings of the National Academy of Sciences*, Jan. 22, 2002, pp. 984-989, vol. 99, No. 2.
Martins. L. O. et al. "Molecular and Biochemical Characterization of a Highly Stable Bacterial Laccase That Occurs as a Structural Component of the *Bacillus subtilis* Endospore Coat" *The Journal of Biological Chemistry*, May 24, 2002, pp. 18849-18859, vol. 227, No. 21.
Koschorreck, S. et al. "Cloning and characterization of a new laccase from *Bacillus licheniformis* catalyzing dimerization of phenolic acids" *Applied Microbiology and Biotechnology*, 2008, pp. 217-224, vol. 79.
Cozen, A. E. et al. "Transcriptional Map of Respiratory Versatility in the Hyperthermophilic Crenarchaeon *Pyrobaculum aerophilum*" *Journal of Bacteriology*, Feb. 2009, pp. 782-794, vol. 191, No. 3.
Hartman, A. L. et al. "The Complete Genome Sequence of *Haloferax volcanil* DS2, a Model Archaeon" *PLoS One*, Mar. 2010, pp. 1-20, vol. 5, Issue 3.

* cited by examiner

*Primary Examiner* — David J Steadman
(74) *Attorney, Agent, or Firm* — Saliwanchik, Lloyd & Eisenschenk

(57) ABSTRACT

The subject invention pertains to a novel purified polypeptide having laccase activity and the nucleic acid sequences encoding the polypeptide. The disclosed polypeptide works at moderately high temperatures from below 20° C. to about 70° C., both acidic and alkaline pH conditions, high salt concentrations and in the presence of organo solvents. The high stability of the enzyme enables its wide applications under even extreme conditions. The invention also provides methods of producing the laccase enzyme.

54 Claims, 21 Drawing Sheets

FIG. 7

| N-terminal amino acid residue | C-terminal amino acid residue | N-terminal amino acid residue | C-terminal amino acid residue | N-terminal amino acid residue | C-terminal amino acid residue | N-terminal amino acid residue | C-terminal amino acid residue | N-terminal amino acid residue | C-terminal amino acid residue | N-terminal amino acid residue | C-terminal amino acid residue |
|---|---|---|---|---|---|---|---|---|---|---|---|
| 140 | 524 | 141 | 524 | 142 | 524 | 143 | 524 | 144 | 524 | 145 | 524 |
| 140 | 525 | 141 | 525 | 142 | 525 | 143 | 525 | 144 | 525 | 145 | 525 |
| 140 | 526 | 141 | 526 | 142 | 526 | 143 | 526 | 144 | 526 | 145 | 526 |
| 140 | 527 | 141 | 527 | 142 | 527 | 143 | 527 | 144 | 527 | 145 | 527 |
| 140 | 528 | 141 | 528 | 142 | 528 | 143 | 528 | 144 | 528 | 145 | 528 |
| 140 | 529 | 141 | 529 | 142 | 529 | 143 | 529 | 144 | 529 | 145 | 529 |
| 140 | 530 | 141 | 530 | 142 | 530 | 143 | 530 | 144 | 530 | 145 | 530 |
| 140 | 531 | 141 | 531 | 142 | 531 | 143 | 531 | 144 | 531 | 145 | 531 |
| 140 | 532 | 141 | 532 | 142 | 532 | 143 | 532 | 144 | 532 | 145 | 532 |
| 140 | 533 | 141 | 533 | 142 | 533 | 143 | 533 | 144 | 533 | 145 | 533 |
| 140 | 534 | 141 | 534 | 142 | 534 | 143 | 534 | 144 | 534 | 145 | 534 |
| 140 | 535 | 141 | 535 | 142 | 535 | 143 | 535 | 144 | 535 | 145 | 535 |
| 140 | 536 | 141 | 536 | 142 | 536 | 143 | 536 | 144 | 536 | 145 | 536 |
| 140 | 537 | 141 | 537 | 142 | 537 | 143 | 537 | 144 | 537 | 145 | 537 |
| 140 | 538 | 141 | 538 | 142 | 538 | 143 | 538 | 144 | 538 | 145 | 538 |
| 140 | 539 | 141 | 539 | 142 | 539 | 143 | 539 | 144 | 539 | 145 | 539 |
| 140 | 540 | 141 | 540 | 142 | 540 | 143 | 540 | 144 | 540 | 145 | 540 |
| 140 | 541 | 141 | 541 | 142 | 541 | 143 | 541 | 144 | 541 | 145 | 541 |
| 140 | 542 | 141 | 542 | 142 | 542 | 143 | 542 | 144 | 542 | 145 | 542 |
| 140 | 543 | 141 | 543 | 142 | 543 | 143 | 543 | 144 | 543 | 145 | 543 |
| 140 | 544 | 141 | 544 | 142 | 544 | 143 | 544 | 144 | 544 | 145 | 544 |
| 140 | 545 | 141 | 545 | 142 | 545 | 143 | 545 | 144 | 545 | 145 | 545 |
| 140 | 546 | 141 | 546 | 142 | 546 | 143 | 546 | 144 | 546 | 145 | 546 |
| 140 | 547 | 141 | 547 | 142 | 547 | 143 | 547 | 144 | 547 | 145 | 547 |
| 140 | 548 | 141 | 548 | 142 | 548 | 143 | 548 | 144 | 548 | 145 | 548 |
| 140 | 549 | 141 | 549 | 142 | 549 | 143 | 549 | 144 | 549 | 145 | 549 |
| 140 | 550 | 141 | 550 | 142 | 550 | 143 | 550 | 144 | 550 | 145 | 550 |
| 140 | 551 | 141 | 551 | 142 | 551 | 143 | 551 | 144 | 551 | 145 | 551 |
| 140 | 552 | 141 | 552 | 142 | 552 | 143 | 552 | 144 | 552 | 145 | 552 |
| 140 | 553 | 141 | 553 | 142 | 553 | 143 | 553 | 144 | 553 | 145 | 553 |
| 140 | 554 | 141 | 554 | 142 | 554 | 143 | 554 | 144 | 554 | 145 | 554 |
| 140 | 555 | 141 | 555 | 142 | 555 | 143 | 555 | 144 | 555 | 145 | 555 |
| 140 | 556 | 141 | 556 | 142 | 556 | 143 | 556 | 144 | 556 | 145 | 556 |
| 140 | 557 | 141 | 557 | 142 | 557 | 143 | 557 | 144 | 557 | 145 | 557 |
| 140 | 558 | 141 | 558 | 142 | 558 | 143 | 558 | 144 | 558 | 145 | 558 |
| 140 | 559 | 141 | 559 | 142 | 559 | 143 | 559 | 144 | 559 | 145 | 559 |
| 140 | 560 | 141 | 560 | 142 | 560 | 143 | 560 | 144 | 560 | 145 | 560 |
| 140 | 561 | 141 | 561 | 142 | 561 | 143 | 561 | 144 | 561 | 145 | 561 |
| 140 | 562 | 141 | 562 | 142 | 562 | 143 | 562 | 144 | 562 | 145 | 562 |
| 140 | 563 | 141 | 563 | 142 | 563 | 143 | 563 | 144 | 563 | 145 | 563 |
| 140 | 564 | 141 | 564 | 142 | 564 | 143 | 564 | 144 | 564 | 145 | 564 |
| 140 | 565 | 141 | 565 | 142 | 565 | 143 | 565 | 144 | 565 | 145 | 565 |
| 140 | 566 | 141 | 566 | 142 | 566 | 143 | 566 | 144 | 566 | 145 | 566 |
| 140 | 567 | 141 | 567 | 142 | 567 | 143 | 567 | 144 | 567 | 145 | 567 |
| 140 | 568 | 141 | 568 | 142 | 568 | 143 | 568 | 144 | 568 | 145 | 568 |
| 140 | 569 | 141 | 569 | 142 | 569 | 143 | 569 | 144 | 569 | 145 | 569 |
| 140 | 570 | 141 | 570 | 142 | 570 | 143 | 570 | 144 | 570 | 145 | 570 |
| 140 | 571 | 141 | 571 | 142 | 571 | 143 | 571 | 144 | 571 | 145 | 571 |
| 140 | 572 | 141 | 572 | 142 | 572 | 143 | 572 | 144 | 572 | 145 | 572 |
| 140 | 573 | 141 | 573 | 142 | 573 | 143 | 573 | 144 | 573 | 145 | 573 |
| 140 | 574 | 141 | 574 | 142 | 574 | 143 | 574 | 144 | 574 | 145 | 574 |
| 140 | 575 | 141 | 575 | 142 | 575 | 143 | 575 | 144 | 575 | 145 | 575 |
| 140 | 576 | 141 | 576 | 142 | 576 | 143 | 576 | 144 | 576 | 145 | 576 |
| 140 | 577 | 141 | 577 | 142 | 577 | 143 | 577 | 144 | 577 | 145 | 577 |
| 140 | 578 | 141 | 578 | 142 | 578 | 143 | 578 | 144 | 578 | 145 | 578 |
| 140 | 579 | 141 | 579 | 142 | 579 | 143 | 579 | 144 | 579 | 145 | 579 |

FIG. 8

LccA from SB01:

```
  1 MTDWSRRRFL QTGAALGIAG TLPQTTTEVS AASPTLEKFV QPLPIPSVRE
 51 PDGQRDGADA YEIAVTEFTQ QLHPDLPETT VWGFDGSYPG PTIEADAGSP
101 VHVRFDNSGL PSEHLFPVDD RLGGTTAENH PGYDGPVPEV RTVTHFHGLE
151 LDPANDGQSD MWTSPGGVEG PRFDSAWQEL PMEQGRTTST YHDHTLGITR
201 LNAYAGLLGL YSITTDAERE LGLPSGDYDI PLLLQDKEFN DDGSLHYPEE
251 FVSAFLGDTA VVNGAVWPYV EVEPRRYRFR ILNGANHRSF DLQLESESGS
301 GVPTMYQFAP GHGFLESVVP IGPNGDLDSL LLTPFERGEL VVDFSDHAGE
351 TLTLANGADM GPELTDLVEF RVSDPSTPPE DASADPTSLS LPTPASYDES
401 DARVTREMTL GTEVRNGLIT HTLNGHVFGD EDAPVYPQLG ATEIWELQNE
451 SGGRHPIHLH LVTFRVIGRG PDGTQPPDPN ELGPKDTVRV DPGERVRILV
501 TFEGYTGQFP WHCHMLEHED NKMMIPFVVE NPVADYANEE NVVDATGLTD
551 AVGDWRNETL ETEVLLEVID QWRSGDEVA
```

LccA from US02:

```
  1 MTDWSRRRFL QTGAALGIAG TLPQTTTEVS AASPTLEKFV QPLPIPSVRE
 51 PDGQRDGADA YEIAVTEFTQ QLHPDLPETT VWGFDGSYPG PTIEADAGSP
101 VHVRFDNSGL PSEHLFPVDD RLGGTTAENH PGYDGPVPEV RTVTHFHGLE
151 LDPANDGQSD MWTSPGGVEG PRFDSAWQEL PMEQGRTTST YHDHTLGITR
201 LNAYAGLLGL YSITTDAERE LGLPSGDYDI PLLLQDKEFN DDGSLHYPEE
251 FVSAFLGDTA VVNGAVWPYV EVEPRRYRFR ILNGANHRSF DLQLESESGS
301 GVPTMYQFAP GHGFLESVVP IGPNGDLDSL LLTPFERGEL VVDFSDHAGE
351 TLTLANGADM GPELTDLVEF RVSDPSTPPE DASADPTSLS LPTPASYDES
401 DARVTREMTL GTEVRNGLIT HTLNGHVFGD EDAPVYPQLG ATEIWELQNE
451 SGGRHPIHLH LVTFRVIGRG PDGTQPPDPN ELGPKDTVRV DPGERVRILV
501 TFEGYTGQFP WHCHMLEHED NKMMIPFVVE NPVADYANEE NVVDATGLTD
551 AVGDWRNETL ETEVLLEVID QWRSGDEVA
```

FIG. 10

SEQUENCE LISTING

```
<160> NUMBER OF SEQ ID NOS: 29

<210> SEQ ID NO 1
<211> LENGTH: 1740
<212> TYPE: DNA
<213> ORGANISM: Haloferax volcanii
<220> FEATURE:
<221> NAME/KEY: CDS
<222> LOCATION: (1)..(1737)

<400> SEQUENCE: 1 atg aca gac tgg tct agg cgg cgg ttc tta cag aca ggc gca gcc ctc      48
Met Thr Asp Trp Ser Arg Arg Arg Phe Leu Gln Thr Gly Ala Ala Leu
1               5                  10                  15 ggc atc gcc gga acg ctc ccg cag acg acg gag gtg tcg gcg gcg          96
Gly Ile Ala Gly Thr Leu Pro Gln Thr Thr Thr Glu Val Ser Ala Ala
            20                  25                  30 tca ccg acg ttg gag aag ttc gtc caa ccg ctt ccg att ccg tcg gtc     144
Ser Pro Thr Leu Glu Lys Phe Val Gln Pro Leu Pro Ile Pro Ser Val
        35                  40                  45 cga gag ccc gac gga cag cga gac ggc gcg gac gcg tac gag ata gcg     192
Arg Glu Pro Asp Gly Gln Arg Asp Gly Ala Asp Ala Tyr Glu Ile Ala
    50                  55                  60 gtc acc gag ttc acc caa cag ctt cac ccg gac ctg ccg gag acg acg     240
Val Thr Glu Phe Thr Gln Gln Leu His Pro Asp Leu Pro Glu Thr Thr
65                  70                  75                  80 gtc tgg ggg ttc gac ggg tcg tat ccc ggc ccg acc atc gag gcg gac     288
Val Trp Gly Phe Asp Gly Ser Tyr Pro Gly Pro Thr Ile Glu Ala Asp
                85                  90                  95 gcc ggg agc ccg gtc cac gtt cgc ttc gac aac agc ggc ctc ccg agc     336
Ala Gly Ser Pro Val His Val Arg Phe Asp Asn Ser Gly Leu Pro Ser
            100                 105                 110 gaa cac ctc ttt ccc gtc gac gac cga ctc ggc ggc acg acc gcg gag     384
Glu His Leu Phe Pro Val Asp Asp Arg Leu Gly Gly Thr Thr Ala Glu
        115                 120                 125 aac cac ccc ggc tac gac ggt ccc gtg ccg gag gtt cgg acc gtc acg     432
Asn His Pro Gly Tyr Asp Gly Pro Val Pro Glu Val Arg Thr Val Thr
    130                 135                 140 cac ttc cac ggc ctt gaa ctc gac ccc gcg aac gac ggg cag tcc gat     480
His Phe His Gly Leu Glu Leu Asp Pro Ala Asn Asp Gly Gln Ser Asp
145                 150                 155                 160 atg tgg acc tcg ccg ggc ggg gtc gag gga ccg cgg ttc gac tcg gcg     528
Met Trp Thr Ser Pro Gly Gly Val Glu Gly Pro Arg Phe Asp Ser Ala
                165                 170                 175 tgg cag gag ctt ccg atg gaa cag ggg cga acg acg tcg acg tac cac     576
Trp Gln Glu Leu Pro Met Glu Gln Gly Arg Thr Thr Ser Thr Tyr His
            180                 185                 190 gac cac acg ctg ggc atc acg cga ctc aac gcc tac gcc ggg ctt ctc     624
Asp His Thr Leu Gly Ile Thr Arg Leu Asn Ala Tyr Ala Gly Leu Leu
        195                 200                 205
```

```
ggt ctc tac tcg att acg acc gac gcg gag cgc gaa ctc ggc ctg ccg      672
Gly Leu Tyr Ser Ile Thr Thr Asp Ala Glu Arg Glu Leu Gly Leu Pro
    210             215                 220 tcg ggc gac tac gac atc ccg ctg ttg ctg caa gac aag gag ttc aac      720
Ser Gly Asp Tyr Asp Ile Pro Leu Leu Leu Gln Asp Lys Glu Phe Asn
225                 230                 235                 240 gac gac ggc tcg ctg cac tac ccc gag gag ttc gtc tcg gcg ttc ctc      768
Asp Asp Gly Ser Leu His Tyr Pro Glu Glu Phe Val Ser Ala Phe Leu
                245                 250                 255 ggc gat acc gcc gtc gtc aac ggg gcc gtg tgg ccg tac gtc gag gtc      816
Gly Asp Thr Ala Val Val Asn Gly Ala Val Trp Pro Tyr Val Glu Val
            260                 265                 270 gaa ccg cgg cgg tac cgg ttc cgc atc ctg aac ggc gcg aat cac cgc      864
Glu Pro Arg Arg Tyr Arg Phe Arg Ile Leu Asn Gly Ala Asn His Arg
        275                 280                 285 tcg ttc gac ctg caa ctg gag agc gaa agc ggg tcg ggc gtc ccg acg      912
Ser Phe Asp Leu Gln Leu Glu Ser Glu Ser Gly Ser Gly Val Pro Thr
    290                 295                 300 atg tac cag ttc gcc ccc ggt cac ggc ttc ctc gaa tcg gtc gtc ccc      960
Met Tyr Gln Phe Ala Pro Gly His Gly Phe Leu Glu Ser Val Val Pro
305                 310                 315                 320 atc ggc ccg aac ggc gac ctc gac tcc ctg ctg ctc acg ccg ttc gag     1008
Ile Gly Pro Asn Gly Asp Leu Asp Ser Leu Leu Leu Thr Pro Phe Glu
                325                 330                 335 cgc ggc gaa ctc gtc gtc gac ttc tcc gac cac gcg ggc gag acg ctc     1056
Arg Gly Glu Leu Val Val Asp Phe Ser Asp His Ala Gly Glu Thr Leu
            340                 345                 350 acg ctc gcc aac ggg gcc gac atg ggt ccc gaa ctg acc gac ctc gtc     1104
Thr Leu Ala Asn Gly Ala Asp Met Gly Pro Glu Leu Thr Asp Leu Val
        355                 360                 365 gag ttc cgc gtc tcg gac ccg tcg acg ccg gag gac gcg agc gcc         1152
Glu Phe Arg Val Ser Asp Pro Ser Thr Pro Glu Asp Ala Ser Ala
    370                 375                 380 gac ccg acg agt ctg tcg ctt ccg acg ccg gcc tcg tac gac gag agc     1200
Asp Pro Thr Ser Leu Ser Leu Pro Thr Pro Ala Ser Tyr Asp Glu Ser
385                 390                 395                 400 gac gcg cgg gtg acc cgc gag atg acg ctc ggg acc gag gtt cga aac     1248
Asp Ala Arg Val Thr Arg Glu Met Thr Leu Gly Thr Glu Val Arg Asn
                405                 410                 415 ggc ctc atc acg cac acg ctg aac ggc cac gtc ttc ggc gac gag gac     1296
Gly Leu Ile Thr His Thr Leu Asn Gly His Val Phe Gly Asp Glu Asp
            420                 425                 430 gcg ccg gtc tac ccg caa ctc gga gcg acc gag ata tgg gaa ctg caa     1344
Ala Pro Val Tyr Pro Gln Leu Gly Ala Thr Glu Ile Trp Glu Leu Gln
        435                 440                 445 aac gag tcg ggc ggg cga cac ccg att cac ctg cat ctg gtc acg ttc     1392
Asn Glu Ser Gly Gly Arg His Pro Ile His Leu His Leu Val Thr Phe
    450                 455                 460 aga gtc atc ggc cgc gga ccc gac ggg acg caa ccg ccg gac ccc aac     1440
Arg Val Ile Gly Arg Gly Pro Asp Gly Thr Gln Pro Pro Asp Pro Asn
465                 470                 475                 480 gaa ctt ggg ccg aaa gac acc gtc cgc gtc gac ccc ggc gaa cgc gtg     1488
Glu Leu Gly Pro Lys Asp Thr Val Arg Val Asp Pro Gly Glu Arg Val
                485                 490                 495 cgg ata ctc gtg acg ttc gag ggc tac acc gga cag ttc ccg tgg cac     1536
Arg Ile Leu Val Thr Phe Glu Gly Tyr Thr Gly Gln Phe Pro Trp His
            500                 505                 510 tgc cac atg ctc gaa cac gag gac aac aag atg atg att ccg ttc gtc     1584
Cys His Met Leu Glu His Glu Asp Asn Lys Met Met Ile Pro Phe Val
        515                 520                 525
```

-continued

```
gtc gag aac ccc gtc gcg gac tac gcg aac gag gag aac gtc gtc gac    1632
Val Glu Asn Pro Val Ala Asp Tyr Ala Asn Glu Glu Asn Val Val Asp
    530                 535                 540 gcg acg ggg ctg acc gac gcg gtc ggt gac tgg cgc aac gaa acc ctc    1680
Ala Thr Gly Leu Thr Asp Ala Val Gly Asp Trp Arg Asn Glu Thr Leu
545                 550                 555                 560 gaa acc gag gtg ctg ctc gaa gtc atc gac cag tgg cga agc ggc gac    1728
Glu Thr Glu Val Leu Leu Glu Val Ile Asp Gln Trp Arg Ser Gly Asp
                565                 570                 575 gaa gtc gcc tga                                                    1740
Glu Val Ala <210> SEQ ID NO 2
<211> LENGTH: 579
<212> TYPE: PRT
<213> ORGANISM: Haloferax volcanii

<400> SEQUENCE: 2

Met Thr Asp Trp Ser Arg Arg Arg Phe Leu Gln Thr Gly Ala Ala Leu
1               5                   10                  15

Gly Ile Ala Gly Thr Leu Pro Gln Thr Thr Thr Glu Val Ser Ala Ala
            20                  25                  30

Ser Pro Thr Leu Glu Lys Phe Val Gln Pro Leu Pro Ile Pro Ser Val
        35                  40                  45

Arg Glu Pro Asp Gly Gln Arg Asp Gly Ala Asp Ala Tyr Glu Ile Ala
    50                  55                  60

Val Thr Glu Phe Thr Gln Gln Leu His Pro Asp Leu Pro Glu Thr Thr
65                  70                  75                  80

Val Trp Gly Phe Asp Gly Ser Tyr Pro Gly Pro Thr Ile Glu Ala Asp
                85                  90                  95

Ala Gly Ser Pro Val His Val Arg Phe Asp Asn Ser Gly Leu Pro Ser
            100                 105                 110

Glu His Leu Phe Pro Val Asp Asp Arg Leu Gly Gly Thr Thr Ala Glu
        115                 120                 125

Asn His Pro Gly Tyr Asp Gly Pro Val Pro Glu Val Arg Thr Val Thr
    130                 135                 140

His Phe His Gly Leu Glu Leu Asp Pro Ala Asn Asp Gly Gln Ser Asp
145                 150                 155                 160

Met Trp Thr Ser Pro Gly Gly Val Glu Gly Pro Arg Phe Asp Ser Ala
                165                 170                 175

Trp Gln Glu Leu Pro Met Glu Gln Gly Arg Thr Thr Ser Thr Tyr His
            180                 185                 190

Asp His Thr Leu Gly Ile Thr Arg Leu Asn Ala Tyr Ala Gly Leu Leu
        195                 200                 205

Gly Leu Tyr Ser Ile Thr Thr Asp Ala Glu Arg Glu Leu Gly Leu Pro
    210                 215                 220

Ser Gly Asp Tyr Asp Ile Pro Leu Leu Leu Gln Asp Lys Glu Phe Asn
225                 230                 235                 240

Asp Asp Gly Ser Leu His Tyr Pro Glu Glu Phe Val Ser Ala Phe Leu
                245                 250                 255

Gly Asp Thr Ala Val Val Asn Gly Ala Val Trp Pro Tyr Val Glu Val
            260                 265                 270

Glu Pro Arg Arg Tyr Arg Phe Arg Ile Leu Asn Gly Ala Asn His Arg
        275                 280                 285

Ser Phe Asp Leu Gln Leu Glu Ser Glu Ser Gly Ser Gly Val Pro Thr
    290                 295                 300
```

```
Met Tyr Gln Phe Ala Pro Gly His Gly Phe Leu Glu Ser Val Val Pro
305                 310                 315                 320

Ile Gly Pro Asn Gly Asp Leu Asp Ser Leu Leu Thr Pro Phe Glu
            325                 330                 335

Arg Gly Glu Leu Val Val Asp Phe Ser Asp His Ala Gly Glu Thr Leu
            340                 345                 350

Thr Leu Ala Asn Gly Ala Asp Met Gly Pro Glu Leu Thr Asp Leu Val
        355                 360                 365

Glu Phe Arg Val Ser Asp Pro Ser Thr Pro Glu Asp Ala Ser Ala
370                 375                 380

Asp Pro Thr Ser Leu Ser Leu Pro Thr Pro Ala Ser Tyr Asp Glu Ser
385                 390                 395                 400

Asp Ala Arg Val Thr Arg Glu Met Thr Leu Gly Thr Glu Val Arg Asn
                405                 410                 415

Gly Leu Ile Thr His Thr Leu Asn Gly His Val Phe Gly Asp Glu Asp
            420                 425                 430

Ala Pro Val Tyr Pro Gln Leu Gly Ala Thr Glu Ile Trp Glu Leu Gln
        435                 440                 445

Asn Glu Ser Gly Gly Arg His Pro Ile His Leu His Leu Val Thr Phe
450                 455                 460

Arg Val Ile Gly Arg Gly Pro Asp Gly Thr Gln Pro Pro Asp Pro Asn
465                 470                 475                 480

Glu Leu Gly Pro Lys Asp Thr Val Arg Val Asp Pro Gly Glu Arg Val
            485                 490                 495

Arg Ile Leu Val Thr Phe Glu Gly Tyr Thr Gly Gln Phe Pro Trp His
        500                 505                 510

Cys His Met Leu Glu His Glu Asp Asn Lys Met Met Ile Pro Phe Val
        515                 520                 525

Val Glu Asn Pro Val Ala Asp Tyr Ala Asn Glu Glu Asn Val Val Asp
530                 535                 540

Ala Thr Gly Leu Thr Asp Ala Val Gly Asp Trp Arg Asn Glu Thr Leu
545                 550                 555                 560

Glu Thr Glu Val Leu Leu Glu Val Ile Asp Gln Trp Arg Ser Gly Asp
                565                 570                 575

Glu Val Ala

<210> SEQ ID NO 3
<211> LENGTH: 630
<212> TYPE: PRT
<213> ORGANISM: Halorubrum lacusprofundi

<400> SEQUENCE: 3

Met Asp Pro Phe Thr Lys Phe Ser Thr Ser Asn Asn Val Cys Ile Thr
1               5                   10                  15

Ile Ser Leu Val Asn Asp Ala Thr Leu Ser Gly Gln Leu Thr Ser Gly
            20                  25                  30

Asp Ser Met Thr Ser Asn Asn Glu Thr Thr Asp His Asp Thr Glu Asn
        35                  40                  45

Arg Lys Arg Leu Ser Arg Arg Ser Val Leu Lys Thr Gly Gly Gly Leu
    50                  55                  60

Gly Ala Ala Ser Val Ile Pro Leu Ser Ala Thr Ser Val Thr Ala Gln
65                  70                  75                  80

Val Glu Glu Leu Thr Ser Pro Asp Ser Ile Leu Asn Ala Gly Trp Gln
                85                  90                  95
```

-continued

```
Glu Ile Gln Ile Gly Asn Ala Lys Pro Ala Val Met Glu Ser Thr Gly
            100                 105                 110

Ser Arg Lys Gly Ala Pro Tyr Tyr His Ile Glu Met Ala Pro Gly Thr
        115                 120                 125

His Glu His His Pro Asp Ile Pro Asp Thr Pro Ile Trp Gly Tyr Lys
    130                 135                 140

Gly Pro Asn Asp Asp Glu Gly Lys Tyr Pro Gly Lys Thr Ile Glu Ala
145                 150                 155                 160

Thr Gln Asn Gln Arg Leu Lys Val Glu Phe Ser Asn Asp Pro Leu Pro
                165                 170                 175

Glu Thr His Leu Leu Thr Asp Ser Val Asp Thr Ala Val His Gly Thr
            180                 185                 190

Lys Pro Glu Asp Tyr Glu Asp Arg Tyr Pro Asp Trp Val Ser Gln Phe
        195                 200                 205

Glu Ala Phe Gly Gly Thr Phe Ala Phe Pro Glu Val Arg Thr Val Thr
    210                 215                 220

His Ala His Gly Val His Val Glu Ser Ala Ser Asp Gly Leu Pro Glu
225                 230                 235                 240

Gln Trp Gln Ser Pro Gly Gly Ile Glu Gly Pro Gln Phe Gln Lys Ala
                245                 250                 255

Val Tyr Asp Tyr Pro Asn Arg Gln Ser Pro Ala Thr Leu Trp Tyr His
            260                 265                 270

Asp His Ala Leu Gly Ile Thr Arg Leu Asn Val Tyr Ala Gly Leu Ala
        275                 280                 285

Gly Phe Tyr Leu Ile Arg Gly Ser Asp Arg Arg Leu Gly Leu Pro
    290                 295                 300

Ser Gly Asp Gln Glu Ile Pro Leu Leu Phe Gln Asp Arg Met Phe His
305                 310                 315                 320

Glu Asn Gly Arg Tyr Lys Tyr Pro Ala Glu Phe Ala Pro Glu Phe Ala
                325                 330                 335

Gly Asp Val Ser Val Val Asn Gly Lys Ala Trp Pro Thr Phe Val Val
            340                 345                 350

Gln Pro Arg Gln Tyr Arg Phe Arg Leu Leu Asn Gly Ser Asn Gly Arg
        355                 360                 365

Phe Phe Asp Ile Ser Leu Glu Asn Glu Asn Asp Gly Glu Val Pro Thr
    370                 375                 380

Ile Tyr Gln Ile Gly Thr Asp Leu Gly Phe Leu Gln Asp Val Val Pro
385                 390                 395                 400

Ile Gly Ser Gly Gln Asp Thr Thr Ser Leu Leu Gly Pro Ala Glu
                405                 410                 415

Arg Ala Asp Val Ile Val Asp Phe Ser Glu Tyr Ala Gly Asp Thr Leu
            420                 425                 430

Thr Val Lys Asn Asp Ala Gly Phe Pro Phe Val Ser Pro Asp Ala Asp
        435                 440                 445

Asn Asn Asp Gly Gly Gly Leu Pro Glu Leu Ala Gln Phe Arg Val Ala
    450                 455                 460

Asp Thr Asp Pro Glu Thr Pro Val Val Asp Pro Thr Thr Leu Lys Leu
465                 470                 475                 480

Pro Gly Pro Glu Thr Phe Arg Glu Glu Ala Thr Lys Thr Thr Arg Gln
                485                 490                 495

Met Ser Leu Glu Thr Thr Thr Leu Asn Gly Leu Asp Thr His Leu Leu
            500                 505                 510

Gly Glu Glu Gly Gly Arg Ala Gly Gly Glu His Trp Asn Asp Pro Val
        515                 520                 525
```

```
Leu Thr Lys Pro Gln Ile Gly Thr Thr Glu Val Trp Glu Ile Thr Asn
    530                 535                 540

Asn Thr Pro Asp Ser His Pro Ile His Leu His Leu Val Asp Phe Gln
545                 550                 555                 560

Val Ile Gly Arg Gly Pro Asp Gly Thr Glu Pro Pro Glu Pro Thr Glu
                565                 570                 575

Arg Gly Asn Lys Asp Thr Val Asn Val Tyr Gly Gly Thr Val Arg
                580                 585                 590

Ile Ile Ser Arg Phe Gly Glu Phe Ser Gly Arg Tyr Val Trp His Cys
            595                 600                 605

His Ile Leu Glu His Glu Asp Gln Glu Met Met Arg Pro Tyr Glu Val
    610                 615                 620

Ile Gln Gly Asn Ser Ser
625                 630

<210> SEQ ID NO 4
<211> LENGTH: 515
<212> TYPE: PRT
<213> ORGANISM: Bacillus subtilis

<400> SEQUENCE: 4

Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125

Phe Glu Gln Thr Gly Pro Tyr Phe Lys Arg Glu Val Tyr His Tyr Pro
    130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270
```

```
Gly Asp Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
    370                 375                 380

Arg Pro Val Leu Leu Leu Asn Asn Lys Arg Trp His Asp Pro Val Thr
385                 390                 395                 400

Glu Thr Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
    450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
            500                 505                 510

Pro His Lys
        515

<210> SEQ ID NO 5
<211> LENGTH: 594
<212> TYPE: PRT
<213> ORGANISM: Stachybotrys chartarum

<400> SEQUENCE: 5

Met Leu Phe Lys Ser Trp Gln Leu Ala Ala Ala Ser Gly Leu Leu Ser
1               5                   10                  15

Gly Val Leu Gly Ile Pro Met Asp Thr Gly Ser His Pro Ile Glu Ala
            20                  25                  30

Val Asp Pro Glu Val Lys Thr Glu Val Phe Ala Asp Ser Leu Leu Ala
        35                  40                  45

Ala Ala Gly Asp Asp Asp Trp Glu Ser Pro Pro Tyr Asn Leu Leu Tyr
    50                  55                  60

Arg Asn Ala Leu Pro Ile Pro Pro Val Lys Gln Pro Lys Met Ile Ile
65                  70                  75                  80

Thr Asn Pro Val Thr Gly Lys Asp Ile Trp Tyr Tyr Glu Ile Glu Ile
                85                  90                  95

Lys Pro Phe Gln Gln Arg Ile Tyr Pro Thr Leu Arg Pro Ala Thr Leu
            100                 105                 110

Val Gly Tyr Asp Gly Met Ser Pro Gly Pro Thr Phe Asn Val Pro Arg
        115                 120                 125
```

-continued

```
Gly Thr Glu Thr Val Val Arg Phe Ile Asn Asn Ala Thr Val Glu Asn
    130                 135                 140

Ser Val His Leu His Gly Ser Pro Ser Arg Ala Pro Phe Asp Gly Trp
145                 150                 155                 160

Ala Glu Asp Val Thr Phe Pro Gly Glu Tyr Lys Asp Tyr Tyr Phe Pro
                    165                 170                 175

Asn Tyr Gln Ser Ala Arg Leu Leu Trp Tyr His Asp His Ala Phe Met
                180                 185                 190

Lys Thr Ala Glu Asn Ala Tyr Phe Gly Gln Ala Gly Ala Tyr Ile Ile
            195                 200                 205

Asn Asp Glu Ala Glu Asp Ala Leu Gly Leu Pro Ser Gly Tyr Gly Glu
210                 215                 220

Phe Asp Ile Pro Leu Ile Leu Thr Ala Lys Tyr Tyr Asn Ala Asp Gly
225                 230                 235                 240

Thr Leu Arg Ser Thr Glu Gly Glu Asp Gln Asp Leu Trp Gly Asp Val
                    245                 250                 255

Ile His Val Asn Gly Gln Pro Trp Pro Phe Leu Asn Val Gln Pro Arg
                260                 265                 270

Lys Tyr Arg Phe Arg Phe Leu Asn Ala Ala Val Ser Arg Ala Trp Leu
            275                 280                 285

Leu Tyr Leu Val Arg Thr Ser Ser Pro Asn Val Arg Ile Pro Phe Gln
290                 295                 300

Val Ile Ala Ser Asp Ala Gly Leu Leu Gln Ala Pro Val Gln Thr Ser
305                 310                 315                 320

Asn Leu Tyr Leu Ala Val Ala Glu Arg Tyr Glu Ile Ile Ile Asp Phe
                    325                 330                 335

Thr Asn Phe Ala Gly Gln Thr Leu Asp Leu Arg Asn Val Ala Glu Thr
                340                 345                 350

Asn Asp Val Gly Asp Glu Asp Glu Tyr Ala Arg Thr Leu Glu Val Met
            355                 360                 365

Arg Phe Val Val Ser Ser Gly Thr Val Glu Asp Asn Ser Gln Val Pro
370                 375                 380

Ser Thr Leu Arg Asp Val Pro Phe Pro Pro His Lys Glu Gly Pro Ala
385                 390                 395                 400

Asp Lys His Phe Lys Phe Glu Arg Ser Asn Gly His Tyr Leu Ile Asn
                    405                 410                 415

Asp Val Gly Phe Ala Asp Val Asn Glu Arg Val Leu Ala Lys Pro Glu
                420                 425                 430

Leu Gly Thr Val Glu Val Trp Glu Leu Glu Asn Ser Ser Gly Gly Trp
            435                 440                 445

Ser His Pro Val His Ile His Leu Val Asp Phe Lys Ile Leu Lys Arg
450                 455                 460

Thr Gly Gly Arg Gly Gln Val Met Pro Tyr Glu Ser Ala Gly Leu Lys
465                 470                 475                 480

Asp Val Val Trp Leu Gly Arg Gly Glu Thr Leu Thr Ile Glu Ala His
                    485                 490                 495

Tyr Gln Pro Trp Thr Gly Ala Tyr Met Trp His Cys His Asn Leu Ile
                500                 505                 510

His Glu Asp Asn Asp Met Met Ala Val Phe Asn Val Thr Ala Met Glu
            515                 520                 525

Glu Lys Gly Tyr Leu Gln Glu Asp Phe Glu Asp Pro Met Asn Pro Lys
530                 535                 540

Trp Arg Ala Val Pro Tyr Asn Arg Asn Asp Phe His Ala Arg Ala Gly
```

```
                    545                 550                 555                 560
Asn Phe Ser Ala Glu Ser Ile Thr Ala Arg Val Gln Glu Leu Ala Glu
                565                 570                 575

Gln Glu Pro Tyr Asn Arg Leu Asp Glu Ile Leu Glu Asp Leu Gly Ile
                580                 585                 590

Glu Glu

<210> SEQ ID NO 6
<211> LENGTH: 572
<212> TYPE: PRT
<213> ORGANISM: Myrothecium verrucaria

<400> SEQUENCE: 6

Met Phe Lys His Thr Leu Gly Ala Ala Ala Leu Ser Leu Leu Phe Asn
1               5                   10                  15

Ser Asn Ala Val Gln Ala Ser Pro Val Pro Glu Thr Ser Pro Ala Thr
                20                  25                  30

Gly His Leu Phe Lys Arg Val Ala Gln Ile Ser Pro Gln Tyr Pro Met
            35                  40                  45

Phe Thr Val Pro Leu Pro Ile Pro Pro Val Lys Gln Pro Arg Leu Thr
50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
130                 135                 140

Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
                165                 170                 175

His Ile Thr Ala Glu Asn Ala Tyr Arg Gly Gln Ala Gly Leu Tyr Met
            180                 185                 190

Leu Thr Asp Pro Ala Glu Asp Ala Leu Asn Leu Pro Ser Gly Tyr Gly
        195                 200                 205

Glu Phe Asp Ile Pro Met Ile Leu Thr Ser Lys Gln Tyr Thr Ala Asn
    210                 215                 220

Gly Asn Leu Val Thr Thr Asn Gly Glu Leu Asn Ser Phe Trp Gly Asp
225                 230                 235                 240

Val Ile His Val Asn Gly Gln Pro Trp Pro Phe Lys Asn Val Glu Pro
                245                 250                 255

Arg Lys Tyr Arg Phe Arg Phe Leu Asp Ala Ala Val Ser Arg Ser Phe
            260                 265                 270

Gly Leu Tyr Phe Ala Asp Thr Asp Ala Ile Asp Thr Arg Leu Pro Phe
        275                 280                 285

Lys Val Ile Ala Ser Asp Ser Gly Leu Leu Glu His Pro Ala Asp Thr
    290                 295                 300

Ser Leu Leu Tyr Ile Ser Met Ala Glu Arg Tyr Glu Val Val Phe Asp
305                 310                 315                 320

Phe Ser Asp Tyr Ala Gly Lys Thr Ile Glu Leu Arg Asn Leu Gly Gly
                325                 330                 335
```

Ser Ile Gly Gly Ile Gly Thr Asp Thr Asp Tyr Asp Asn Thr Asp Lys
                340                 345                 350

Val Met Arg Phe Val Val Ala Asp Asp Thr Thr Gln Pro Asp Thr Ser
            355                 360                 365

Val Val Pro Ala Asn Leu Arg Asp Val Pro Phe Pro Ser Pro Thr Thr
        370                 375                 380

Asn Thr Pro Arg Gln Phe Arg Phe Gly Arg Thr Gly Pro Thr Trp Thr
385                 390                 395                 400

Ile Asn Gly Val Ala Phe Ala Asp Val Gln Asn Arg Leu Leu Ala Asn
                405                 410                 415

Val Pro Val Gly Thr Val Glu Arg Trp Glu Leu Ile Asn Ala Gly Asn
            420                 425                 430

Gly Trp Thr His Pro Ile His Ile His Leu Val Asp Phe Lys Val Ile
        435                 440                 445

Ser Arg Thr Ser Gly Asn Asn Ala Arg Thr Val Met Pro Tyr Glu Ser
450                 455                 460

Gly Leu Lys Asp Val Val Trp Leu Gly Arg Arg Glu Thr Val Val Val
465                 470                 475                 480

Glu Ala His Tyr Ala Pro Phe Pro Gly Val Tyr Met Phe His Cys His
                485                 490                 495

Asn Leu Ile His Glu Asp His Asp Met Met Ala Ala Phe Asn Ala Thr
            500                 505                 510

Val Leu Pro Asp Tyr Gly Tyr Asn Ala Thr Val Phe Val Asp Pro Met
        515                 520                 525

Glu Glu Leu Trp Gln Ala Arg Pro Tyr Glu Leu Gly Glu Phe Gln Ala
530                 535                 540

Gln Ser Gly Gln Phe Ser Val Gln Ala Val Thr Glu Arg Ile Gln Thr
545                 550                 555                 560

Met Ala Glu Tyr Arg Pro Tyr Ala Ala Ala Asp Glu
                565                 570

<210> SEQ ID NO 7
<211> LENGTH: 34
<212> TYPE: PRT
<213> ORGANISM: Artificial sequence
<220> FEATURE:
<223> OTHER INFORMATION: HvoB0205 (lccA) up primer

<400> SEQUENCE: 7

Thr Gly Gly Gly Cys Gly Thr Cys Ala Thr Ala Gly Ala Cys Ala
1               5                   10                  15

Gly Ala Cys Thr Gly Gly Thr Cys Thr Ala Gly Gly Cys Gly Gly Cys
                20                  25                  30

Gly Gly

<210> SEQ ID NO 8
<211> LENGTH: 60
<212> TYPE: PRT
<213> ORGANISM: Artificial sequence
<220> FEATURE:
<223> OTHER INFORMATION: HvoB0205 (lccA) down

<400> SEQUENCE: 8

Ala Ala Ala Ala Gly Cys Thr Thr Cys Ala Cys Thr Cys Thr Cys
1               5                   10                  15

Gly Ala Ala Cys Thr Gly Cys Gly Gly Gly Thr Gly Cys Gly Ala Cys
                20                  25                  30

```
Cys Ala Ala Gly Thr Ala Cys Thr Gly Gly Cys Gly Ala Cys Thr Thr
        35                  40                  45

Cys Gly Thr Cys Gly Cys Cys Gly Cys Thr Thr Cys
        50                  55                  60

<210> SEQ ID NO 9
<211> LENGTH: 31
<212> TYPE: PRT
<213> ORGANISM: Artificial sequence
<220> FEATURE:
<223> OTHER INFORMATION: HvoB0205 (lccA) down 2

<400> SEQUENCE: 9

Ala Ala Ala Ala Gly Cys Thr Thr Thr Cys Ala Gly Cys Cys Ala
1               5                   10                  15

Cys Thr Thr Cys Gly Thr Cys Gly Cys Cys Gly Cys Thr Thr Cys
                20                  25                  30

<210> SEQ ID NO 10
<211> LENGTH: 13
<212> TYPE: PRT
<213> ORGANISM: Artificial sequence
<220> FEATURE:
<223> OTHER INFORMATION: peptide sequence

<400> SEQUENCE: 10

Lys Phe Val Gln Pro Leu Pro Ile Pro Ser Val Arg Glu
1               5                   10

<210> SEQ ID NO 11
<211> LENGTH: 19
<212> TYPE: PRT
<213> ORGANISM: Artificial sequence
<220> FEATURE:
<223> OTHER INFORMATION: peptide sequence

<400> SEQUENCE: 11

Lys Phe Val Gln Pro Leu Pro Ile Pro Ser Val Arg Glu Pro Asp Gly
1               5                   10                  15

Gln Arg Asp

<210> SEQ ID NO 12
<211> LENGTH: 40
<212> TYPE: PRT
<213> ORGANISM: Artificial sequence
<220> FEATURE:
<223> OTHER INFORMATION: peptide sequence

<400> SEQUENCE: 12

Lys Glu Phe Asn Asp Asp Gly Ser Leu His Tyr Pro Glu Glu Phe Val
1               5                   10                  15

Ser Ala Phe Leu Gly Asp Thr Ala Val Val Asn Gly Ala Val Trp Pro
                20                  25                  30

Tyr Val Glu Val Glu Pro Arg Arg
        35                  40

<210> SEQ ID NO 13
<211> LENGTH: 19
<212> TYPE: PRT
<213> ORGANISM: Artificial sequence
<220> FEATURE:
<223> OTHER INFORMATION: peptide sequence

<400> SEQUENCE: 13

Arg Phe Asp Asn Ser Gly Leu Pro Ser Glu His Leu Phe Pro Val Asp
```

```
            1               5                  10                 15
Asp Arg Leu

<210> SEQ ID NO 14
<211> LENGTH: 22
<212> TYPE: PRT
<213> ORGANISM: Artificial sequence
<220> FEATURE:
<223> OTHER INFORMATION: peptide sequence

<400> SEQUENCE: 14

Arg Leu Gly Gly Thr Thr Ala Glu Asn His Pro Gly Tyr Asp Gly Pro
1               5                  10                 15

Val Pro Glu Val Arg Thr
            20

<210> SEQ ID NO 15
<211> LENGTH: 33
<212> TYPE: PRT
<213> ORGANISM: Artificial sequence
<220> FEATURE:
<223> OTHER INFORMATION: peptide sequence

<400> SEQUENCE: 15

Arg Thr Val Thr His Phe His Gly Leu Glu Leu Asp Pro Ala Asn Asp
1               5                  10                 15

Gly Gln Ser Asp Met Trp Thr Ser Pro Gly Gly Val Glu Gly Pro Arg
            20                  25                 30

Phe

<210> SEQ ID NO 16
<211> LENGTH: 16
<212> TYPE: PRT
<213> ORGANISM: Artificial sequence
<220> FEATURE:
<223> OTHER INFORMATION: peptide sequence

<400> SEQUENCE: 16

Arg Phe Asp Ser Ala Trp Gln Glu Leu Pro Met Glu Gln Gly Arg Thr
1               5                  10                 15

<210> SEQ ID NO 17
<211> LENGTH: 16
<212> TYPE: PRT
<213> ORGANISM: Artificial sequence
<220> FEATURE:
<223> OTHER INFORMATION: peptide sequence

<400> SEQUENCE: 17

Arg Thr Thr Ser Thr Tyr His Asp His Thr Leu Gly Ile Thr Arg Leu
1               5                  10                 15

<210> SEQ ID NO 18
<211> LENGTH: 21
<212> TYPE: PRT
<213> ORGANISM: Artificial sequence
<220> FEATURE:
<223> OTHER INFORMATION: peptide sequence

<400> SEQUENCE: 18

Arg Leu Asn Ala Tyr Ala Gly Leu Leu Gly Leu Tyr Ser Ile Thr Thr
1               5                  10                 15

Asp Ala Glu Arg Glu
            20
```

```
<210> SEQ ID NO 19
<211> LENGTH: 20
<212> TYPE: PRT
<213> ORGANISM: Artificial sequence
<220> FEATURE:
<223> OTHER INFORMATION: peptide sequence

<400> SEQUENCE: 19

Arg Glu Leu Gly Leu Pro Ser Gly Asp Tyr Asp Ile Pro Leu Leu Leu
1               5                   10                  15

Gln Asp Lys Glu
            20

<210> SEQ ID NO 20
<211> LENGTH: 12
<212> TYPE: PRT
<213> ORGANISM: Artificial sequence
<220> FEATURE:
<223> OTHER INFORMATION: peptide sequence

<400> SEQUENCE: 20

Arg Phe Arg Ile Leu Asn Gly Ala Asn His Arg Ser
1               5                   10

<210> SEQ ID NO 21
<211> LENGTH: 11
<212> TYPE: PRT
<213> ORGANISM: Artificial sequence
<220> FEATURE:
<223> OTHER INFORMATION: peptide sequence

<400> SEQUENCE: 21

Arg Glu Met Thr Leu Gly Thr Glu Val Arg Asn
1               5                   10

<210> SEQ ID NO 22
<211> LENGTH: 37
<212> TYPE: PRT
<213> ORGANISM: Artificial sequence
<220> FEATURE:
<223> OTHER INFORMATION: peptide sequence

<400> SEQUENCE: 22

Arg Val Ser Asp Pro Ser Thr Pro Glu Ala Ser Ala Asp Pro
1               5                   10                  15

Thr Ser Leu Ser Leu Pro Thr Pro Ala Ser Tyr Asp Glu Ser Asp Ala
                20                  25                  30

Arg Val Thr Arg Glu
        35

<210> SEQ ID NO 23
<211> LENGTH: 13
<212> TYPE: PRT
<213> ORGANISM: Artificial sequence
<220> FEATURE:
<223> OTHER INFORMATION: peptide sequence

<400> SEQUENCE: 23

Arg His Pro Ile His Leu His Leu Val Thr Phe Arg Val
1               5                   10

<210> SEQ ID NO 24
<211> LENGTH: 22
<212> TYPE: PRT
<213> ORGANISM: Artificial sequence
<220> FEATURE:
```

```
<223> OTHER INFORMATION: peptide sequence

<400> SEQUENCE: 24

Arg Val Ile Gly Arg Gly Pro Asp Gly Thr Gln Pro Pro Asp Pro Asn
1               5                   10                  15

Glu Leu Gly Pro Lys Asp
            20

<210> SEQ ID NO 25
<211> LENGTH: 26
<212> TYPE: PRT
<213> ORGANISM: Artificial sequence
<220> FEATURE:
<223> OTHER INFORMATION: peptide sequence

<400> SEQUENCE: 25

Arg Val Ile Gly Arg Gly Pro Asp Gly Thr Gln Pro Pro Asp Pro Asn
1               5                   10                  15

Glu Leu Gly Pro Lys Asp Thr Val Arg Val
            20                  25

<210> SEQ ID NO 26
<211> LENGTH: 18
<212> TYPE: PRT
<213> ORGANISM: Artificial sequence
<220> FEATURE:
<223> OTHER INFORMATION: peptide sequence

<400> SEQUENCE: 26

Arg Gly Pro Asp Gly Thr Gln Pro Pro Asp Pro Asn Glu Leu Gly Pro
1               5                   10                  15

Lys Asp

<210> SEQ ID NO 27
<211> LENGTH: 22
<212> TYPE: PRT
<213> ORGANISM: Artificial sequence
<220> FEATURE:
<223> OTHER INFORMATION: peptide sequence

<400> SEQUENCE: 27

Arg Gly Pro Asp Gly Thr Gln Pro Pro Asp Pro Asn Glu Leu Gly Pro
1               5                   10                  15

Lys Asp Thr Val Arg Val
            20

<210> SEQ ID NO 28
<211> LENGTH: 579
<212> TYPE: PRT
<213> ORGANISM: Haloferax volcanii SB01

<400> SEQUENCE: 28

Met Thr Asp Trp Ser Arg Arg Arg Phe Leu Gln Thr Gly Ala Ala Leu
1               5                   10                  15

Gly Ile Ala Gly Thr Leu Pro Gln Thr Thr Thr Glu Val Ser Ala Ala
            20                  25                  30

Ser Pro Thr Leu Glu Lys Phe Val Gln Pro Leu Pro Ile Pro Ser Val
        35                  40                  45

Arg Glu Pro Asp Gly Gln Arg Asp Gly Ala Asp Ala Tyr Glu Ile Ala
    50                  55                  60

Val Thr Glu Phe Thr Gln Gln Leu His Pro Asp Leu Pro Glu Thr Thr
65              70                  75                  80
```

-continued

```
Val Trp Gly Phe Asp Gly Ser Tyr Pro Gly Pro Thr Ile Glu Ala Asp
             85                  90                  95

Ala Gly Ser Pro Val His Val Arg Phe Asp Asn Ser Gly Leu Pro Ser
            100                 105                 110

Glu His Leu Phe Pro Val Asp Asp Arg Leu Gly Gly Thr Thr Ala Glu
            115                 120                 125

Asn His Pro Gly Tyr Asp Gly Pro Val Pro Glu Val Arg Thr Val Thr
            130                 135                 140

His Phe His Gly Leu Glu Leu Asp Pro Ala Asn Asp Gly Gln Ser Asp
145                 150                 155                 160

Met Trp Thr Ser Pro Gly Gly Val Glu Gly Pro Arg Phe Asp Ser Ala
                165                 170                 175

Trp Gln Glu Leu Pro Met Glu Gln Gly Arg Thr Thr Ser Thr Tyr His
            180                 185                 190

Asp His Thr Leu Gly Ile Thr Arg Leu Asn Ala Tyr Ala Gly Leu Leu
            195                 200                 205

Gly Leu Tyr Ser Ile Thr Thr Asp Ala Glu Arg Glu Leu Gly Leu Pro
            210                 215                 220

Ser Gly Asp Tyr Asp Ile Pro Leu Leu Leu Gln Asp Lys Glu Phe Asn
225                 230                 235                 240

Asp Asp Gly Ser Leu His Tyr Pro Glu Glu Phe Val Ser Ala Phe Leu
                245                 250                 255

Gly Asp Thr Ala Val Val Asn Gly Ala Val Trp Pro Tyr Val Glu Val
            260                 265                 270

Glu Pro Arg Arg Tyr Arg Phe Arg Ile Leu Asn Gly Ala Asn His Arg
            275                 280                 285

Ser Phe Asp Leu Gln Leu Glu Ser Glu Ser Gly Ser Gly Val Pro Thr
            290                 295                 300

Met Tyr Gln Phe Ala Pro Gly His Gly Phe Leu Glu Ser Val Val Pro
305                 310                 315                 320

Ile Gly Pro Asn Gly Asp Leu Asp Ser Leu Leu Leu Thr Pro Phe Glu
                325                 330                 335

Arg Gly Glu Leu Val Val Asp Phe Ser Asp His Ala Gly Glu Thr Leu
            340                 345                 350

Thr Leu Ala Asn Gly Ala Asp Met Gly Pro Glu Leu Thr Asp Leu Val
            355                 360                 365

Glu Phe Arg Val Ser Asp Pro Ser Thr Pro Pro Glu Asp Ala Ser Ala
            370                 375                 380

Asp Pro Thr Ser Leu Ser Leu Pro Thr Pro Ala Ser Tyr Asp Glu Ser
385                 390                 395                 400

Asp Ala Arg Val Thr Arg Glu Met Thr Leu Gly Thr Glu Val Arg Asn
                405                 410                 415

Gly Leu Ile Thr His Thr Leu Asn Gly His Val Phe Gly Asp Glu Asp
            420                 425                 430

Ala Pro Val Tyr Pro Gln Leu Gly Ala Thr Glu Ile Trp Glu Leu Gln
            435                 440                 445

Asn Glu Ser Gly Gly Arg His Pro Ile His Leu His Leu Val Thr Phe
            450                 455                 460

Arg Val Ile Gly Arg Gly Pro Asp Gly Thr Gln Pro Pro Asp Pro Asn
465                 470                 475                 480

Glu Leu Gly Pro Lys Asp Thr Val Arg Val Asp Pro Gly Glu Arg Val
                485                 490                 495

Arg Ile Leu Val Thr Phe Glu Gly Tyr Thr Gly Gln Phe Pro Trp His
            500                 505                 510
```

```
Cys His Met Leu Glu His Glu Asp Asn Lys Met Met Ile Pro Phe Val
            515                 520                 525

Val Glu Asn Pro Val Ala Asp Tyr Ala Asn Glu Glu Asn Val Val Asp
        530                 535                 540

Ala Thr Gly Leu Thr Asp Ala Val Gly Asp Trp Arg Asn Glu Thr Leu
545                 550                 555                 560

Glu Thr Glu Val Leu Leu Glu Val Ile Asp Gln Trp Arg Ser Gly Asp
            565                 570                 575

Glu Val Ala

<210> SEQ ID NO 29
<211> LENGTH: 579
<212> TYPE: PRT
<213> ORGANISM: Haloferax volcanii US02

<400> SEQUENCE: 29

Met Thr Asp Trp Ser Arg Arg Phe Leu Gln Thr Gly Ala Ala Leu
1               5                   10                  15

Gly Ile Ala Gly Thr Leu Pro Gln Thr Thr Glu Val Ser Ala Ala
            20                  25                  30

Ser Pro Thr Leu Glu Lys Phe Val Gln Pro Leu Pro Ile Pro Ser Val
            35                  40                  45

Arg Glu Pro Asp Gly Gln Arg Asp Gly Ala Asp Ala Tyr Glu Ile Ala
        50                  55                  60

Val Thr Glu Phe Thr Gln Gln Leu His Pro Asp Leu Pro Glu Thr Thr
65                  70                  75                  80

Val Trp Gly Phe Asp Gly Ser Tyr Pro Gly Pro Thr Ile Glu Ala Asp
                85                  90                  95

Ala Gly Ser Pro Val His Val Arg Phe Asp Asn Ser Gly Leu Pro Ser
            100                 105                 110

Glu His Leu Phe Pro Val Asp Asp Arg Leu Gly Gly Thr Thr Ala Glu
        115                 120                 125

Asn His Pro Gly Tyr Asp Gly Pro Val Pro Glu Val Arg Thr Val Thr
    130                 135                 140

His Phe His Gly Leu Glu Leu Asp Pro Ala Asn Asp Gly Gln Ser Asp
145                 150                 155                 160

Met Trp Thr Ser Pro Gly Gly Val Glu Gly Pro Arg Phe Asp Ser Ala
                165                 170                 175

Trp Gln Glu Leu Pro Met Glu Gln Gly Arg Thr Thr Ser Thr Tyr His
            180                 185                 190

Asp His Thr Leu Gly Ile Thr Arg Leu Asn Ala Tyr Ala Gly Leu Leu
        195                 200                 205

Gly Leu Tyr Ser Ile Thr Thr Asp Ala Glu Arg Glu Leu Gly Leu Pro
    210                 215                 220

Ser Gly Asp Tyr Asp Ile Pro Leu Leu Leu Gln Asp Lys Glu Phe Asn
225                 230                 235                 240

Asp Asp Gly Ser Leu His Tyr Pro Glu Glu Phe Val Ser Ala Phe Leu
                245                 250                 255

Gly Asp Thr Ala Val Val Asn Gly Ala Val Trp Pro Tyr Val Glu Val
            260                 265                 270

Glu Pro Arg Arg Tyr Arg Phe Arg Ile Leu Asn Gly Ala Asn His Arg
        275                 280                 285

Ser Phe Asp Leu Gln Leu Glu Ser Glu Ser Gly Ser Gly Val Pro Thr
    290                 295                 300
```

-continued

```
Met Tyr Gln Phe Ala Pro Gly His Gly Phe Leu Glu Ser Val Val Pro
305                 310                315                    320

Ile Gly Pro Asn Gly Asp Leu Asp Ser Leu Leu Leu Thr Pro Phe Glu
                325             330                 335

Arg Gly Glu Leu Val Val Asp Phe Ser Asp His Ala Gly Glu Thr Leu
            340             345                 350

Thr Leu Ala Asn Gly Ala Asp Met Gly Pro Glu Leu Thr Asp Leu Val
            355             360             365

Glu Phe Arg Val Ser Asp Pro Ser Thr Pro Pro Glu Asp Ala Ser Ala
    370                 375                 380

Asp Pro Thr Ser Leu Ser Leu Pro Thr Pro Ala Ser Tyr Asp Glu Ser
385                 390             395                     400

Asp Ala Arg Val Thr Arg Glu Met Thr Leu Gly Thr Glu Val Arg Asn
                405             410                 415

Gly Leu Ile Thr His Thr Leu Asn Gly His Val Phe Gly Asp Glu Asp
                420             425             430

Ala Pro Val Tyr Pro Gln Leu Gly Ala Thr Glu Ile Trp Glu Leu Gln
            435             440             445

Asn Glu Ser Gly Gly Arg His Pro Ile His Leu His Leu Val Thr Phe
450                     455             460

Arg Val Ile Gly Arg Gly Pro Asp Gly Thr Gln Pro Pro Asp Pro Asn
465             470             475                     480

Glu Leu Gly Pro Lys Asp Thr Val Arg Val Asp Pro Gly Glu Arg Val
            485             490             495

Arg Ile Leu Val Thr Phe Glu Gly Tyr Thr Gly Gln Phe Pro Trp His
                500             505             510

Cys His Met Leu Glu His Glu Asp Asn Lys Met Met Ile Pro Phe Val
        515             520             525

Val Glu Asn Pro Val Ala Asp Tyr Ala Asn Glu Glu Asn Val Val Asp
    530             535             540

Ala Thr Gly Leu Thr Asp Ala Val Gly Asp Trp Arg Asn Glu Thr Leu
545             550             555                     560

Glu Thr Glu Val Leu Leu Glu Val Ile Asp Gln Trp Arg Ser Gly Asp
                565             570             575

Glu Val Ala
```

HALOFERAX VOLCANII LACCASE AND VARIANTS AND FRAGMENTS THEREOF

This application is the U.S. national stage application of International Patent Application No. PCT/US2010/034177, filed May 10, 2010, which claims the benefit of U.S. Provisional Application Ser. No. 61/176,587, filed May 8, 2009, the disclosures of which are hereby incorporated by reference in their entirety, including all figures, tables and amino acid or nucleic acid sequences.

This invention was made with government support under grant number 5R01GM057498 awarded by the National Institutes of Health. The government has certain rights in the invention.

BACKGROUND OF THE INVENTION

Multicopper oxidases (MCOs) are a family of enzymes that include laccases (p-diphenol: dioxygen oxidoreductases, EC 1.10.3.2), ascorbate oxidases (EC 1.10.3.3), ferroxidases (EC 1.16.3.1), bilirubin oxidases (EC 1.3.3.5) and other enzyme subfamilies (Solomon et al, 1996; Hoegger et al., 2006). MCOs couple the oxidation of organic and/or inorganic substrates to the four-electron reduction of molecular oxygen to water. These enzymes often have four Cu atoms classified into Type 1 (T1), Type 2 (T2) and Type 3 (T3) centers, in which a mononuclear T1 center on the surface of the enzyme provides long range intramolecular one-electron transfer from electron-donating substrates to an internal trinuclear T2/T3 center formed by a T2 Cu coordinated to a T3 Cu pair. The T2/T3 cluster subsequently reduces dioxygen to water.

Enzymes of the laccase subfamily oxidize a broad range of compounds including phenols, polyphenols, aromatic amines, and non-phenolic substrates by one-electron transfer to molecular oxygen and, thus, have a wide variety of applications spanning from biofuels to human health. A lacquer tree laccase (from *Rhus vernicifera*) has been used in paint and adhesives in East Asia for more than 6000 years (Hüttermann et al., 2001). Laccases have also been used in the delignification of pulp, bleaching of textile and carcinogenic dyes, detoxification of water and soils, removal of phenolics from wines, improving adhesive properties of lignocellulosic products, determination of bilirubin levels in serum, and transformation of antibiotics and steroids (Sakurai et al., 2007). Likewise, laccases have demonstrated potential in biosensors, bioreactors and biofuel cells (Shleev et al., 2005).

Although laccases were once thought to be restricted to eukaryotes (fungi, plants, insects), recent evidence suggests their widespread distribution in bacteria (Claus, 2004). In plants, laccases are required for normal cell wall structure and integrity in xylem fibers and apparently involved in lignification (Ranocha et al., 2002). In fungi, laccases mediate the modification and degradation of complex natural polymers such as lignin and humic acids (Widsten et al, 2008; Claus et al., 1998). The lacasse-like MCOs of insects seem to play an important role in cuticular sclerotization, melanization, iron homeostasis and the oxidation of toxic compounds in the diet (Claus, 2004). Likewise, the more recently described laccase-like MCOs of bacteria have a wide variety of biological roles including sporulation, electron transport, pigmentation, metal (copper, iron, manganese) homeostasis, oxidation of phenolate-siderophorcs, phenoxazinone synthesis, cell division and morphorgenesis (Claus, 2003). For example, Martins et al. (2002) characterized a laccase enzyme isolated from the endospore coat of *Bacillus subtilis*. Koschorreck et al. (2008) recently disclosed a laccase isolated from *Bacillus licheniformis* and found it to catalyze dimerization of phenolic acids.

However, these laccases usually have very limited temperature, pH, and salt range because of the living conditions of the plants and bacteria. Their industrial application, which sometimes requires high laccase activity under extreme conditions, may, thus, be further limited. Therefore, laccases with extreme thermal and salt/solvent stability are highly desired.

Archaea, one of the three domains of life along with the Bacteria and Eukarya, have evolved to thrive in harsh environmental conditions including high temperature, extreme pH, and/or low water activity. Thus, their systems and enzymes are deemed ideal for a number of industrial processes. In contrast to the widespread occurrence of laccases in eukaryotes and bacteria, only a few putative MCOs are predicted in genomes of archaea including the hyperthermophilic crenarchaeote *Pyrobaculum aerophilum* (PAE1888) (Fitz-Gibbon et al., 2002) and the PAE1888-encoded enzyme is not likely to catalyze the oxidation of phenolic compounds particularly in the absence of metal supplementation. This limitation in PAE1888 activity is based on the inventors' dendrogram analysis (see report) and transcriptional mapping by Cozen et al. (2009, J. Bacteriol. 191(3): 782-794), both of which suggest PAE1888 is not a true laccase and instead encodes a metal oxidase and/or $NO_2^-$ or $N_2O$ reductase. In addition, whereas all of the archaea with identified MCO grow in the presence of oxygen, most archaea with sequenced genomes are strict anaerobes, likely limiting the distribution of the oxygen-utilizing MCOs among this group.

BRIEF SUMMARY OF THE INVENTION

The subject invention provides a novel laccase that is highly thermostable and salt/solvent tolerant and nucleic acids encoding the laccase. In one embodiment, the purified laccase has a molecular weight of about 65 kDa and an amino acid sequence comprising SEQ ID NO: 2.

In another embodiment, the novel laccase is isolated and purified from strains of *Haloferax volcanii* species. Examples of some *Haloferax volcanii* strains are listed in Table 1. Preferably, the laccase is produced by *Hfx. volcanii* SB01 and US02 The molecular weight is about 65 kDa, determined by gel-filtration chromatography.

Also provided by the subject invention is a method of producing the above disclosed laccase. In one embodiment, the laccase is produced in the culture media of its natural host, for example, *Hfx. volcanii* SB01, the method comprising the steps of culturing a *Haloferax volcanii* strain under conditions suitable to produce the enzyme and then recovering the enzyme from the cells or the culture media. In another embodiment, the laccase is produced in a production host, such as *E. coli, Bacillus megaterium* and *Saccharomyces cerevisiae*, by means of recombinant technology.

The subject invention further relates to the use of the claimed laccase in various industrially important protocols that utilize laccases.

BRIEF DESCRIPTION OF THE DRAWINGS

FIG. 6A-*Effect* of temperature on the catalytic activity of LccA. LccA (51 µg·ml$^{-1}$) activity was assayed at different temperatures (22° to 70° C.) in T buffer with 185 mM NaCl using SGZ (1 mM) as the substrate. Activity is expressed as percent relative to the optimum at 45° C.; FIG. 6B-*Effect* of salt on the catalytic activity of LccA. The SGZ oxidizing activity of LccA was measured at different concentrations (up to 1.0 M) of NaCl (●) and KCl (○) in T buffer at 45° C. Activity is expressed as percent relative to 185 mM NaCl; FIG. 6C-*Effect* of pH on the catalytic activity of LccA. LccA activity was assayed with SGZ (●) from pH 6 to 11 and with ABTS (○) from pH 3 to 8 at 45° C. using following buffers: 100 mM sodium acetate for pH 3 to 6, 25 mM Tris-HCl for pH 7 to 10, and 25 mM glycine-NaOH for pH 11. Activity is expressed as percent relative to oxidation of ABTS at pH 6. FIG. 6D-T*hermostability* of LccA. Purified enzyme (50.6 µg·ml$^{-1}$) was pre-incubated in T buffer supplemented with 185 mM NaCl at temperatures from 37° to 70° C. for up to 60 h, as indicated. After incubation, laccase activity was estimated by oxidation of SGZ at standard conditions. Activity is presented as percent relative to incubation on ice (37° C. (●), 45° C. (■), 50° C. (▲), 55° C. (◆), 60° C. (○), 65° C. (□) and 70° C. (Δ)); FIG. 6E-S*alt* tolerance of LccA protein. Purified enzyme (16.5 µg·ml$^{-1}$) was pre-incubated for 30 min in T buffer at pH 8.4 supplemented with different concentrations of NaCl (0 to 1.4 M) as indicated. Samples were diluted to a final concentration 4.12 µg·ml$^{-1}$ protein and 185 mM NaCl in T buffer and assayed for SGZ oxidizing activity under standard conditions. Residual activity was calculated as percent relative to incubation at 185 mM NaCl. FIG. 6F—Effect of mixed organo-solvents on LccA activity. Enzyme (7.5 µg·ml$^{-1}$) was incubated in T buffer with 185 mM NaCl in the presence and absence of 25% (v/v) solvent (DMSO, DMF, ethanol and methanol) at room temperature for 90 min (white bar), 3 h (grey bar) and 24 h (black bar). Enzyme and solvent were diluted 4-fold in T buffer with 185 mM NaCl and residual enzyme activity was estimated under standard conditions using SGZ as the substrate. Activity is calculated as percent relative to incubation without solvent.

FIG. 7 shows sequence alignment of *Hfx. volcanii* laccase (LccA, Hvo_B0205, SEQ ID NO: 2) to multicopper oxidases. Vertical line (|) represents cleavage site which has experimental evidence for LccA and Mver_Q12737. TAT motifs, indicated by a bold double underline, are based on in silico analysis using TATFIND v1.4 server. The one cysteine and 10 histidine residues that bind the four copper atoms to form the Type I, II and III active sites of known multicopper oxidases are indicated above the amino acid residue (●). Potential O- and N-linked glycosylation sites with EnsembleGly scores above 0.8 are indicated by respective O* and N* above the residue with the Thr-X$_5$-P-X-P and N-X-T/S motifs boxed. Amino acid sequences in bold and underlined represent peptides detected by MS/MS analysis of the laccase purified from *Hfx. volcanii* (details of MS/MS analysis in Table 5). Abbreviation and GenBank accession number: Hlac_ZP-02016827 (SEQ ID NO: 3), *Halorubrum lacusprofundi* putative multicopper oxidase (Copeland et al., 2008); Bsub_BAA22774 (SEQ ID NO: 4), *Bacillus subtilis* spore coat protein A (CotA) with laccase activity (Martins et al., 2002); Scha_AAY23005 (SEQ ID NO: 5), *Stachybotrys chartarum* phenol oxidase A (Mander et al., 2006); Mver_Q12737 (SEQ ID NO: 6), *Myrothecium verrucaria* bilirubin oxidase (Koikeda et al., 1993).

FIG. 8 provides various exemplary fragments of the laccase disclosed herein. The numbering of the N- and C-terminal amino acid residue is provided with reference to FIG. 7 and SEQ ID NO: 2.

FIG. 10 shows MS-analysis of LccA. LccA fractions purified from *H. volcanii* SB01 (SEQ ID NO: 28) and US02 (SEQ ID NO: 29) were digested with trypsin and analyzed by MS as described in methods. Tryptic peptides identified by MS are underlined and detailed in Table 5.

BRIEF DESCRIPTION OF THE SEQUENCES

Figure 1A:
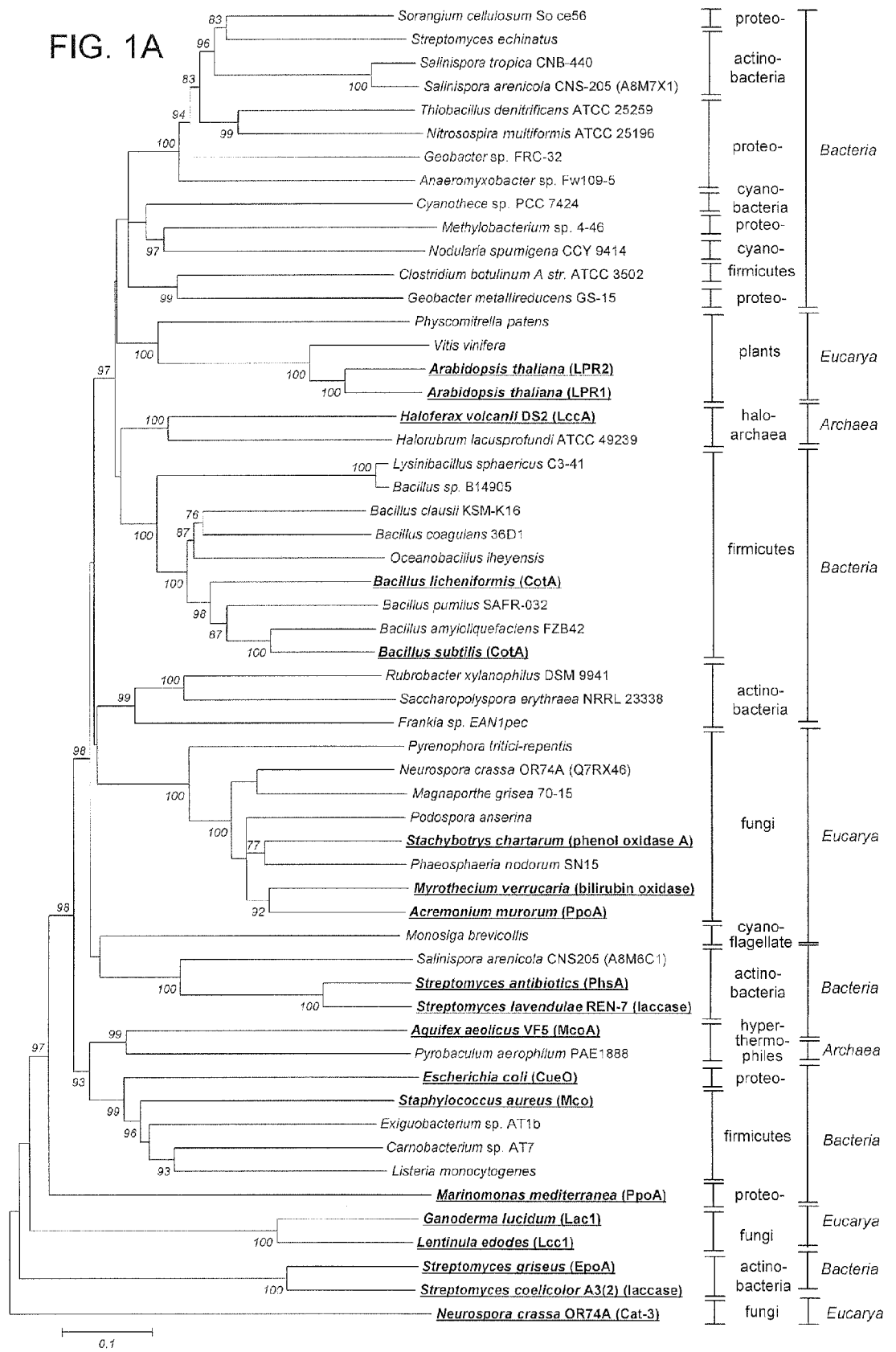
FIG. 1A shows phylogenetic comparison of laccase and related multicopper oxidase protein sequences. Origin of protein sequences used for the analysis with corresponding accession numbers and references to biochemical and/or physiological studies in parenthesis were as follows: *Hfx. volcanii* DS2 (HvoB0205, LccA this study), *Acremonium murorum* (polyphenol oxidase or PpoA, Q9P8C3) (Gouka et al., 2001), *Anaeromyxobacter* sp. Fw109-5 (A7H7L9), *Aquifex aeolicus* (McoA, AAC07157.1) (Fernandes et al., 2007), *Arabidopsis thaliana* (ABG81319, LPR1) and (NP_565008.1, LPR2) (Svistoonoff et al., 2007), *Bacillus amyloliquefaciens* FZB42 (A7Z229), *Bacillus clausii* KSM-K16 (Q5WEM6), *Bacillus coagulans* 36D1 (A2U4V3), *Bacillus licheniformis* DSM 13/ATCC 14580 (Q65MU7) (Koschoor et al., 2008), *Bacillus pumilus* SAFR-032 (A8FAG9), *Bacillus subtilis* (P07788, CotA) (Martins et al., 2002), *Bacillus* sp. B 14905 (A318L4), *Carnobacterium* sp. AT7 (ZP 02185070.1), *Clostridium botulinum* ATCC 3502 (A51081), *Cyanothece* sp. PCC 7424 (B2F9S5), *Escherichia coli* (P36649.2, CueO) (Wang et al., 2004), *Exiguobacterium* sp. AT1b (ZP_02990140.1), *Frankia* sp. EAN1pec (A8LFX9), *Ganoderma lucidum* (Lac1, Q9HG17) (Joo et al., 2008), *Geobacter metallireducens* GS-15 (Q39TP0), *Geobacter* sp. FRC-32 (QOYK09), *Halorubrum lacusprofundi* ATCC 49239 (A7D715), *Lentinula edodes* (Lcc1, Q68LM1) (Sakamoto et al., 2008), *Listeria monocytogenes* (ABV56573.1), *Lysinibacillus sphaericus* C3-41 (B1HU92), *Magnaporthe grisea* (A4RGT9), *Marinomonas mediterranea* MMB-1 (PpoA, Q9KJB8) (Sanchez-Amat et al., 2001), *Methylobacterium* sp. 4-46 (B0U918), *Monosiga brevicollis* (XP_001748107.1), *Myrothecium verrucaria* (Q12737) (Koikeda et al., 1993), *Neurospora crassa* (Q7RX46), *Nitrosospira multiformis* ATCC 25196 (Q2Y8L3), *Nodularia spumigena* CCY 9414 (AOZH42), *Oceanobacillus iheyensis* (Q8CXJ7), *Phaeosphaeria nodorum* (QOUUB4), *Physcomitrella patens* (XP_001760041), *Podospora anserine* (B2ANK8), *Pyrenophora tritici-repentis* Pt-1C-BFP (XP_001940237), *Pyrobaculum aerophilum* (PAE1888, AAL63794.1), *Rubrobacter xylanophilus* DSM 9941 (NC 008148), *Saccharopolyspora erythraea* NRRL 23338 (A4FAR2), *Salinispora arenicola* CNS-205 (A8M6C1 and A8M7X1), *Salinispora tropica* CNB-440 (A4X8A2), *Sorangium cellulosum* So ce56 (A9GCD5), *Stachybotrys chartarum* (Q4ZIR9) (Mander et al., 2006), *Staphylococcus aureus* (Mco, Q69HT9) (Sitthisak et al., 2005), *Streptomyces antibioticus* (phenoxazinone synthase or PhsA, Q53692) (Choy et al., 1981), *Streptomyces coelicolor* A3(2) (NP 630785, SLAC) (Machczynski et al., 2004), *Streptomyces echinatus* (A1C171), *Streptomyces griseus* (EpoA, Q93HV5) (Endo et al., 2003), *Streptomyces lavendulae* REN-7 (laccase, Q8 GB87) (Suzuki et al., 2003), *Thiobacillus denitrificans* ATCC 25259 (Q3SJX4) and *Vitis vinifera* (CA042253.1). *Neurospora crassa* catalase-3 (Cat-3, Q9C169) served as the outgroup for this analysis. Species with associated biochemical and/or physiological studies of their MCO family member are underlined and in bold.

SEQ ID NO: 1 polynucleotide sequence encoding *Hfx. volcanii* laccase.
SEQ ID NO: 2 polypeptide sequence of *Hfx. volcanii* laccase.

DETAILED DISCLOSURE OF THE INVENTION

In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis).

"Nucleotide sequence", "polynucleotide" or "nucleic acid" can be used interchangeably and are understood to mean, according to the present invention, either a double-stranded DNA, a single-stranded. DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

The terms "comprising", "consisting of" and "consisting essentially of" are defined according to their standard meaning. The terms may be substituted for one another throughout the instant application in order to attach the specific meaning associated with each term.

The phrases "isolated" or "biologically pure" refer to material that is substantially or essentially free from components which normally accompany the material as it is found in its native state. The term "isolated" requires that the material be removed from its original environment (e.g., the natural environment if it is naturally occurring). For example, a naturally-occurring polynucleotide or polypeptide present in a viable eukaryotic cell or a prokaryotic cell is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. Specifically excluded from the term "isolated" are: nucleic acid sequences found in databases containing the complete genomic sequence of *Haloferax volcanii*, naturally-occurring chromosomes (such as chromosome spreads of *Haloferax volcanii* or chromosomes isolated from *Haloferax volcanii*), artificial chromosomal libraries of *Haloferax volcanii*, genomic libraries of *Haloferax volcanii*, and cDNA libraries of *Haloferax volcanii* that exist either as an in vitro nucleic acid preparation or as a transfected/transformed host cell preparation, wherein the host cells are either an in vitro heterogeneous preparation or plated as a heterogeneous population of single colonies. Thus, "an isolated polynucleotide comprising SEQ ID NO: 1 is specifically defined as excluding those sequences found in a database containing the genomic sequence of *Haloferax volcanii*, naturally-occurring chromosomes of *Haloferax volcanii* (e.g., chromosome spreads of *Haloferax volcanii* or chromosomes isolated from *Haloferax volcanii*), artificial chromosomal libraries of *Haloferax volcanii*, genomic libraries of *Haloferax volcanii*, and/or cDNA libraries of *Haloferax volcanii* that contain SEQ ID NO: 1 or a polynucleotide encoding SEQ ID NO: 2. Further specifically excluded are whole cell (*Haloferax volcanii*) genomic DNA or whole cell RNA preparations (including whole cell preparations which are mechanically sheared or enzymatically digested). Further specifically excluded are the above whole cell *Haloferax volcanii* preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

In one aspect of the invention, antibodies that specifically bind to SEQ ID NO: 2 are provided. In various embodiments, these antibodies do not cross-react with other proteins that are structurally related.

One aspect of the subject invention provides isolated, purified, and/or recombinant polypeptides having laccase activity, wherein the polypeptides have a molecular weight of about 65 kDa (using gel-filtration chromatography) and/or comprise the amino acid sequence SEQ ID NO: 2. Another aspect of the invention provides for fragments of the polypeptides disclosed herein, wherein the polypeptide fragments retain laccase activity. Polypeptide fragments, as described herein, can be obtained by cleaving the polypeptides of the invention with a proteolytic enzyme (such as trypsin, chymotrypsin, collagenase or other known proteases) or with a chemical reagent, such as cyanogen bromide (CNBr). Alternatively, polypeptide fragments can be generated in a highly acidic environment, for example at pH 2.5. After cleavage via any of these agents, the polypeptide fragments can be assayed for laccase activity as described herein. Also provided are compositions comprising SEQ ID NO: 2, or fragments thereof retaining laccase activity and a carrier (e.g., an aqueous or organic liquid). In various aspects of the invention, fragments having laccase activity, such as those disclosed in FIG. 8, are provided. Alternatively, fragments of SEQ ID NO: 2 having laccase activity can start at any one of amino acid residues 140, 141, 142, 143, 144 or 145 and the C-terminal amino acid of the fragment can be any amino acid found at positions 524 through 579 of SEQ ID NO: 2.

The polypeptides can be obtained from a *Haloferax volcanii* strain, for example, *Hfx. volcanii* DS2 or a mutant strain thereof. In a preferred embodiment, a mutant strain *Hfx. volcanii* SB01 is used. In another embodiment, the polypeptide has the amino acid sequence set forth in SEQ ID NO: 2.

A "variant polypeptide" (or polypeptide variant) is to be understood to designate polypeptides exhibiting, in relation to SEQ ID NO: 2, certain modifications. These modifications can include a deletion, addition, or substitution of at least one amino acid, a truncation, an extension, a chimeric fusion, a mutation, or polypeptides exhibiting post-translational modifications. Among these homologous variant polypeptides, are those comprising amino acid sequences exhibiting between at least (or at least about) 39.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to SEQ ID NO: 2. Typically, the percent identity is calculated with reference to the full-length, native, and/or naturally occurring polypeptide (e.g., SEQ ID NO: 2). In all instances, variant polypeptides retain the laccase activity associated with SEQ ID NO: 2. Variant polypeptides can also comprise one or more heterologous polypeptide sequences (e.g., tags that facilitate purification of the polypeptides of the invention (see, for example, U.S. Pat. No. 6,342,362, hereby incorporated by reference in its entirety).

Strains of *Haloferax volcanii* are available from various public culture collections, including the American Type Culture Collection (ATCC, USA), ATCC 29605; Deutsche Sammlung von Mikroorganismenn and Zellkulturen GmbH (DSMZ, Germany), DSM 3757 and 5716; Czechoslovak Collection of Microorganisms (CCM, Czech Republic), CCM 2852; National Collection of Industrial and Marine Bacteria (NCIMB, Scotland), NCIMB 2012; and Institute for Fermentation (IFO, Japan), IFO 14742. The microorganisms can be cultivated on a suitable medium, including, for example, a halobacterium medium ATCC 974. The medium can also include other ingredients, such as salts, buffers, drugs, and nutrients. In one embodiment, the strain is grown in complex medium ATCC 974 and lactate-minimal medium (Hv-LMM). The medium can also include other ingredients such as antibiotics, e.g. ampicillin and novobiocin. The culture can be grown in liquid or solid medium. In some embodiments, the Hv-LMM is supplemented with $CuSO_4$ for faster production of the enzyme in *Hfx. volcanii*, presumably based on a more efficient conversion of the apoenzyme to the mature copper-loaded, active form. For example, the concentration of $CuSO_4$ can be about 100 µM. Various other embodiments utilize less agitated culture conditions over heavily agitated conditions in obtaining greater production of the claimed laccase.

The production of the polypeptide can be detected by measuring the laccase activity (e.g., oxidation of a substrate). Suitable substrates for measuring the enzyme activity include 2,2'-azino-bis-3-ethylbenzthiazoline-6-sulphonic acid (ABTS), 2,6-dimethoxyphenol (DMP), 2-methoxyphenol (guaiacol), and 4-hydroxy-3,5-dimethoxybenzaldehyde azine (syringaldazine or SGZ). Oxidation of the substrate can be determined by absorbance increase or decrease by spectroscopy at certain wavelength, for example, ABTS at 420 nm with $\epsilon=36,000$ $M^{-1}$ $cm^{-1}$; SGZ at 526 nm with $\epsilon=65,000$ $M^{-1}$ $cm^{-1}$; DMP at 468 nm with $\epsilon=49,000$ $M^{-1}$ $cm^{-1}$; guaiacol at 436 nm with $\epsilon=26,600$ $M^{-1}$ $cm^{-1}$; bilirubin at 440 nm with $\epsilon=56,300$ $M^{-1}$ $cm^{-1}$.

As discussed above, the polypeptide can be produced in its native host. In one embodiment, the native host is *Hfx. volcanii* DS70. The polypeptide of SEQ ID NO: 2 can also be produced by an engineered host cell expressing a nucleic acid encoding SEQ ID NO: 2. Non-limiting examples of engineered host cells expressing a nucleic acid encoding SEQ ID NO: 2 include *E. coli*, *Bacillus megaterium* and *Saccharomyces cerevisiae*.

Therefore, the subject invention relates to methods of producing a polypeptide comprising cultivating a *Haloferax volcanii* strain that is able to secrete the polypeptide naturally or a host cell containing the encoding gene, under conditions suitable to produce the polypeptide, and recovering the polypeptide from the culture medium.

The recovered polypeptide can then be isolated and purified by using known methods of protein purification, such as precipitation, centrifugation, filtration, anion exchange chromatography, and gel-filtration chromatography. In several embodiments, the laccase is purified from a culture broth by filtration. The culture broth is further purified by ethanol precipitation and centrifugation. Anion-exchange chromatography is further used for purification. The purified product can be verified by SDS-PAGE, mass spectroscopy and in gel activity staining. In one embodiment, the purity of the obtained laccase is between 38 to 68% from the above application. In another embodiment, SDS-PAGE gives a molecular weight of 70.7 kDa. In yet another embodiment, the gel filtration chromatography estimates the native molecular mass to be about 65 kDa.

The purified and concentrated polypeptide can be characterized for enzyme activity, thermostability, salt/solvent stability, or other properties. The laccase activity of the purified polypeptide at various temperatures, pH, and salt concentrations can be determined using SGZ and/or ABTS as substrates. The thermo, salt or solvent stability can be determined by incubating the purified polypeptide at various temperatures, salt concentrations, or solvent types with the other factors fixed.

The polypeptide, and biologically active fragments thereof, disclosed herein exhibits laccase activity at temperatures of about 20° C. to about 70° C., about 30° C. to about 55° C. (with over 80% laccase activity) or between about 45° C. to about 50° C. In addition, the polypeptide is salt resistant exhibits laccase activity at all concentrations between about 100 mM and 300 mM NaCl or KCl (e.g., >100 mM NaCl or KCl, between 100-250 mM NaCl or KCl, between about 150-250 mM NaCl or KCl, or about 200 mM NaCl or KCl). In one embodiment, at same protein concentration, the polypeptide displays about 1.5-fold higher activity in KCl than NaCl.

Figure 6A:
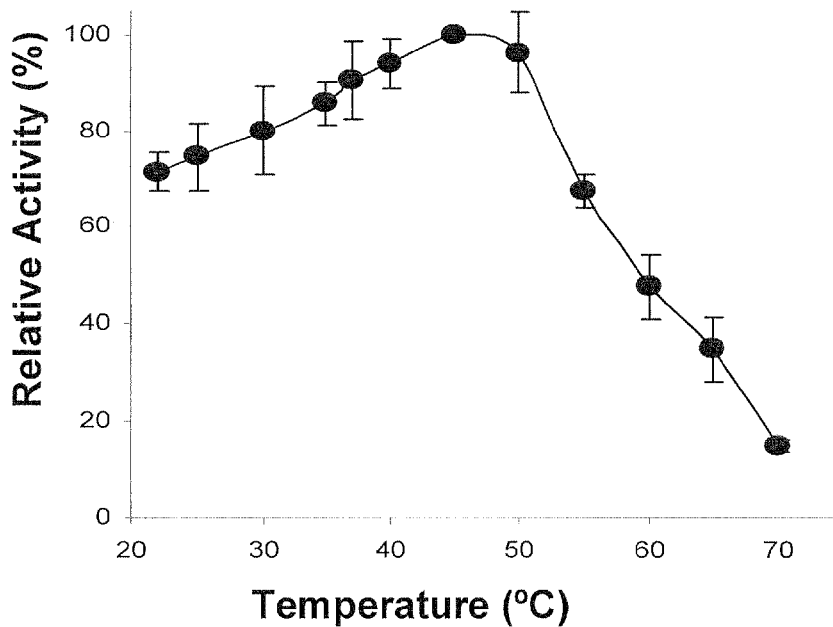
FIGS. 6A-6F show temperature (FIG. 6A), salt (FIG. 6B) and pH (FIG. 6C) optima of LccA purified from *Hfx. volcanii* SB01.
Figure 6B:
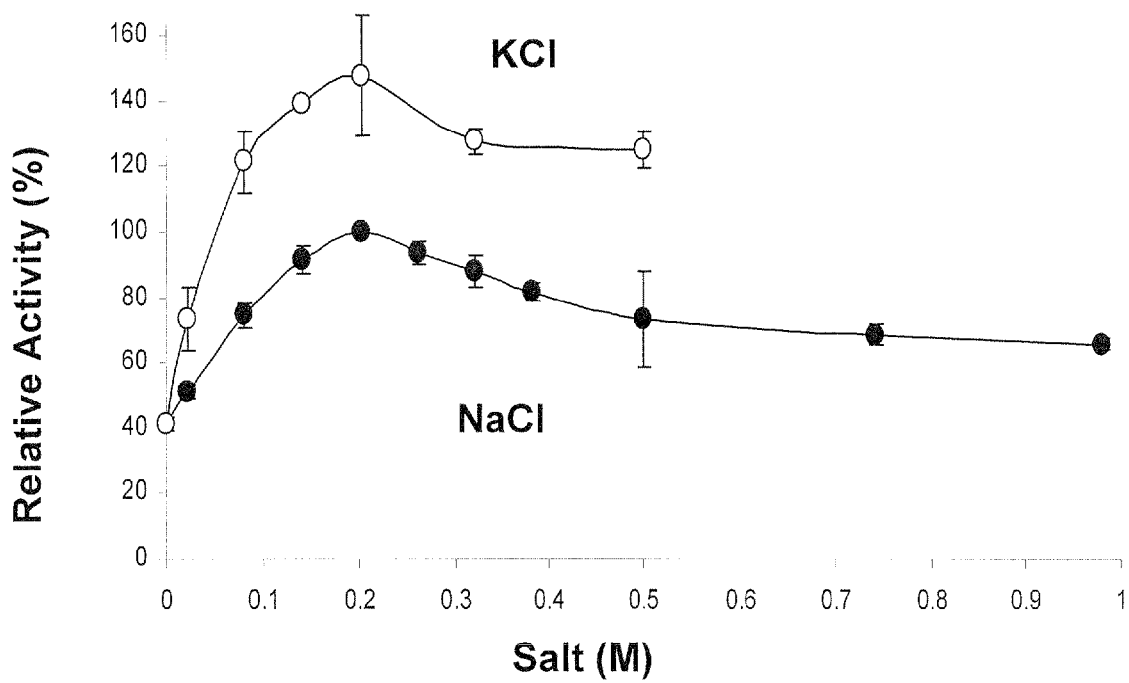
Figure 6C:
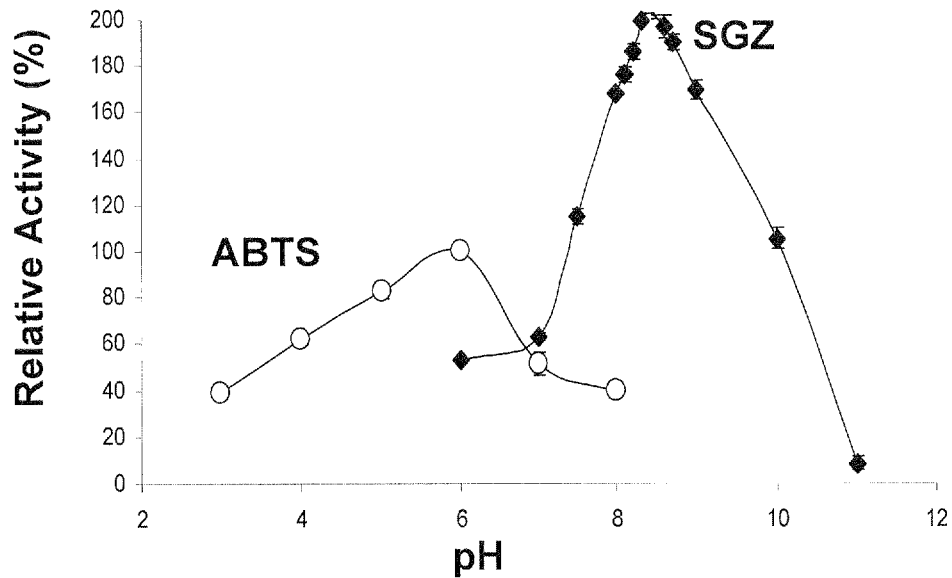

The polypeptide of the subject invention is catalytically active under both acidic and alkaline pH conditions while being substrate dependent (FIG. 6C). In the presence of ABTS, the polypeptide has laccase activity over the range of pH=3-8, 4-7, or 5-6.5. The activity is at its highest at about pH 6. The subject polypeptide can also oxidize SGZ at pH range of pH=6-11, 7-10, or 8-9. The optimum pH for SGZ, oxidation is about 8.4.

Most microbial laccases display optimal activity at low pH. The alkalophilic nature of the polypeptide disclosed herein is advantageous in various industrial applications including paper pulp bleaching and wastewater treatment processes. Unlike the subject polypeptide, the few microbial laccases that are active at alkaline pH do not exhibit significant activity below pH 6.0. These unique catalytic properties of the described polypeptide underline its potential as a source of high-value laccases.

Figure 6D:
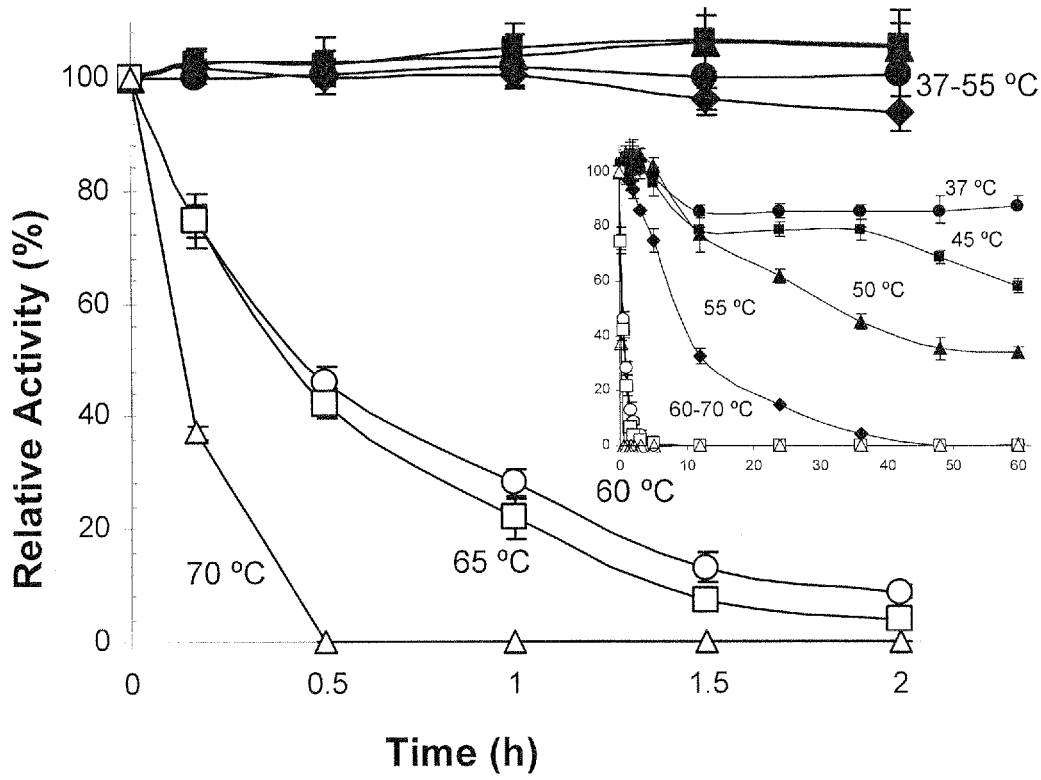

The subject polypeptide is also thermostable at temperatures from 37 to 70° C. In one embodiment, it is fully active after 1 h at 55° C. and 5 h at 50° C., with a half-live of inactivation at 50° C. of 31.5 h (FIGS. 6A and 6D). The polypeptide retains nearly all of its original laccase activity at 37° C. and 35 to 60% of its activity at 45 to 50° C., after incubation for 2½ days. These results reveal that the polypeptide described herein is highly thermostable, retaining most of its activity after prolonged incubation at moderately high temperatures. Advantageously, most of industrial processes work at optimal temperatures of not more than 50° C. Hence the temperature optima and thermal stability of the subject polypeptide are well within the required range for most of the industrial bioprocesses.

Figure 6E:
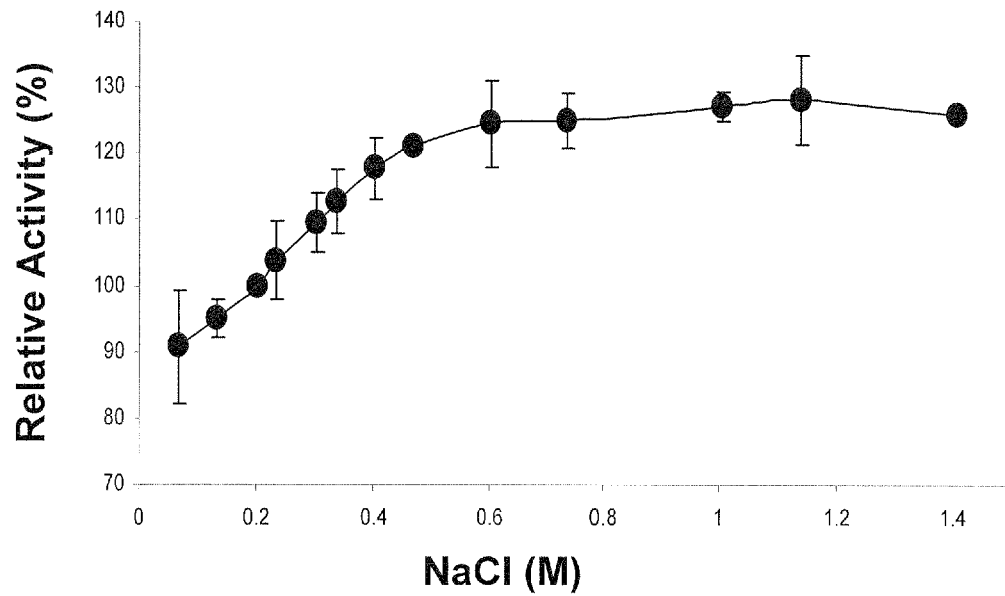

Furthermore, the purified polypeptide is stable in a wide range of NaCl concentrations from 100 mM to, at least, 1.4 M, retaining nearly all of its original activity if not higher (FIGS. 6B and 6E). Prolonged incubation, from about 90 min to 24 h, of the polypeptide in salt does not alter this activity profile. This is better than a recently analyzed laccase from a bacterium isolated from a mangrove swamp (i.e., *Streptomyces psammoticus*) which only demonstrated salt tolerance with full activity after incubation for 24 h in 0.8 M NaCl (Niladevi et al., 2008). Salt tolerance is one of the preferred characteristics from an industrial stand-point as laccases are used for effluent treatment including bleaching and decolorization of phenolilc dyes where salt concentration can be a constraint for in situ enzymatic treatment of wastewaters rich in salts.

Figure 6F:
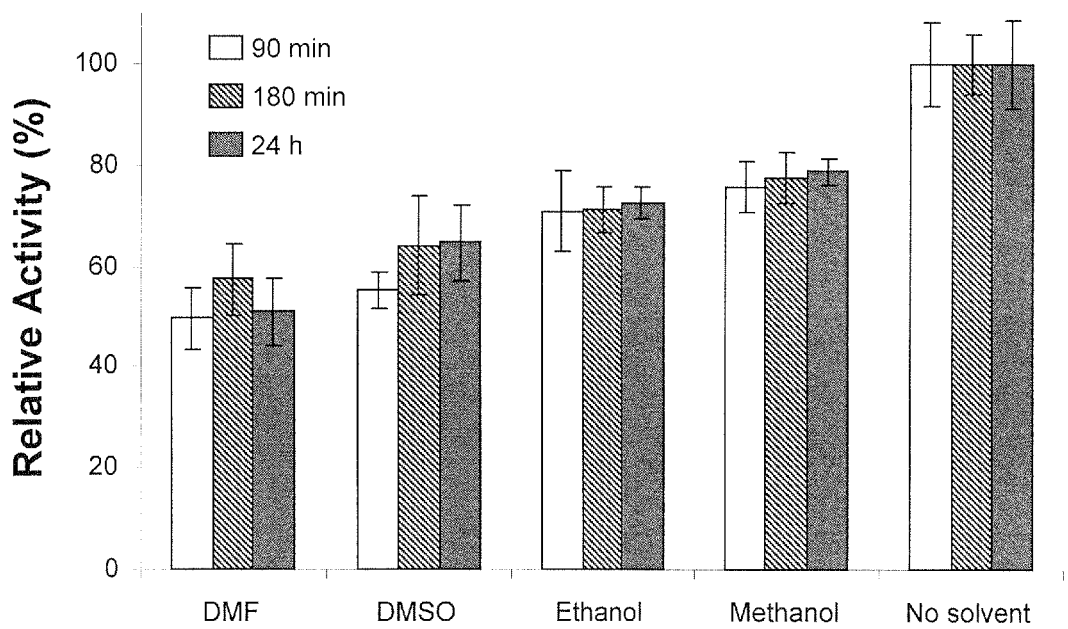

The purified polypeptide is highly solvent tolerant. In the experimental conditions described in Example 5, the polypeptide is relatively stable in all solvents (i.e., methanol, ethanol, dimethyl sulfoxide or DMSO and dimethylformamide or DMF) examined, retaining nearly 75% of its activity after about 24 h incubation in methanol or ethanol and over 50% of its activity after incubation in DMSO or DMF (FIG. 6F). Solvent compatibility of the subject polypeptide from *Hfx. volcanii* may be used to facilitate transformation of insoluble lignin components and lower the degree of polymerization of phenoxyl radicals originated during lignin oxidation. More importantly, many laccase substrates and mediators are insoluble or poorly soluble in water and the solvent stability of the disclosed polypeptide would be of much interest to change the direction of catalytic reactions and to gain access to insoluble substrates and enhance the solubility of mediators. Additionally, several potential applications of laccases need to be performed in the presence of significant amounts (in some cases up to 50% v/v) of water-miscible organic cosolvent. Therefore, several industrial applications would greatly benefit from the addition of water-miscible organic cosolvents to laccase-mediated reactions, particularly the conversion of insoluble substrates such as lignin and its derivatives to useful products (Barreca et al., 2003; Potthast et al., 1995; d'Acunzo et al, 2004).

The subject invention also provides polynucleotides, vectors, genetic constructs and transformed host cells. These polynucleotides, vectors, genetic constructs, and transformed host cells contain nucleic acids encoding a laccase as described herein. Nucleic acid probes derived from such nucleic acids are also provided by the subject invention. Thus, the subject invention also provides isolated, recombinant, and/or purified polynucleotide sequences comprising:

a) a polynucleotide sequence encoding a polypeptide comprising SEQ ID NO: 2;

b) a homologous polynucleotide sequence having at least about 20% to 99.99% identity to a polynucleotide sequence encoding a polypeptide SEQ ID NO: 2, wherein said polynucleotide encodes a polypeptide having laccase activity;

c) a polynucleotide sequence comprising SEQ ID NO: 1;

d) a homologous polynucleotide sequence having at least about 20% to 99.99% identity to the polynucleotide sequence of SEQ ID NO: 1 and encoding a polypeptide having laccase activity;

e) a polynucleotide that is complementary to the polynucleotides set forth in (a), (h), (c), or (d);

a genetic construct comprising a polynucleotide sequence as set forth in (a), (b), (c), (d), or (e);

g) a vector comprising a polynucleotide or genetic construct as set forth in (a), (b), (c), (d), (e), or (f);

h) a host cell comprising a vector as set forth in (g);

i) a polynucleotide that hybridizes under low, intermediate or high stringency with a polynucleotide sequence as set forth in (a), (b), (c), (d) or (e); or j) a probe comprising a polynucleotide according to (a), (b), (c), (d), (e), (0, or (g) and, optionally, a label or marker;

A homologous polynucleotide sequence, for the purposes of the present invention, encompasses a sequence having a percentage identity with the polynucleotide sequences, set forth herein, of between at least (or at least about) 20.00% to 99.99% (inclusive). The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J Mol. Biol.* 215(3): 403-410; Thompson et al., 1994; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$$Tm=81.5° C.+16.6 \text{ Log }[Na^+]+0.41(\% G+C)-0.61 (\%\text{formamide})-600/\text{length of duplex in base pairs.}$$

Washes are typically carried out as follows:

(1) twice at room temperature for 15 minutes in 1×SSPE, 0.1% SDS (low stringency wash);

(2) once at $T_m$-20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$$Tm(° C.)=2(\text{number } T/A \text{ base pairs})+4(\text{number } G/C \text{ base pairs})$$

(Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment>70 or so bases in length, the following conditions can be used:

Low: 1 or 2×SSPE, room temperature
Low: 1 or 2×SSPE, 42° C.
Intermediate: 0.2× or 1×SSPE, 65° C.
High: 0.1×SSPE, 65° C.

By way of another non-limiting example, procedures using conditions of high stringency can also be performed as follows: pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10⁶ cpm of $^{32}$P-labeled probe. Alternatively, the hybridization step can be performed at 65° C. in the presence of SSC buffer, 1×SSC corresponding to 0.15 M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments is the total number of nucleotides found in the full-length sequence encoding a particular polypeptide (e.g., a polypeptide such as that of SEQ ID NO: 2). The term "successive" can be interchanged with the term "consecutive" or the phrase "contiguous span". Thus, in some embodiments, a polynucleotide fragment may be referred to as "a contiguous span of at least X nucleotides, wherein X is any integer value beginning with 5; the upper limit for such fragments is one nucleotide less than the total number of nucleotides found in the full-length sequence encoding a particular polypeptide (e.g., a polypeptide comprising SEQ ID NO: 2).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

The subject invention provides, in one embodiment, methods for the identification of the presence of nucleic acids according to the subject invention in transformed host cells or in cells expressing similar laccases. In these varied embodiments, the invention provides for the detection of nucleic acids in a sample (obtained from a cell) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine, et al., *Proc. Natl. Acad. Sci.* 74:5350), 4) magnetic particle separation, 5) nucleic acid or DNA chips, 6) reverse Northern blot assay, 7) dot blot assay, 8) in situ hybridization, 9) RNase protection assay (Melton, et al., *Nuc. Acids Res.* 12:7035 and as described in the 1998 catalog of Ambion, Inc., Austin, Tex.), 10) ligase chain reaction, 11) polymerase chain reaction (PCR), 12) reverse transcriptase (RT)-PCR (Berchtold, et al., *Nuc. Acids. Res.* 17:453), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (*Science* 270:467-470, 1995; *Proc. Natl. Acad. Sci, U.S.A.* 93:10614-10619, 1996). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 cm² microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (Genome Research 6:492-503, 1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences of to the invention may also be used in analytical systems, such as DNA chips. DNA chips and their uses are well known in the art and (see for example, U.S. Pat. Nos. 5,561,071; 5,753,439; 6,214,545; Schena et al., *BioEssays,* 1996, 18:427-431; Bianchi et al., *Clin. Diagn. Viral.,* 1997, 8:199-208; each of which is hereby incorporated by reference in their entireties) and/or are provided by commercial vendors such as Affymetrix, Inc. (Santa Clara, Calif.). In addition, the nucleic acid sequences of the subject invention can be used as molecular weight markers in nucleic acid analysis procedures.

The subject invention also provides for modified nucleotide sequences. Modified nucleic acid sequences will be understood to mean any nucleotide sequence that has been modified, according to techniques well known to persons skilled in the art, and exhibiting modifications in relation to the native, naturally occurring nucleotide sequences.

The subject invention also provides genetic constructs comprising: a) a polynucleotide sequence encoding a polypeptide comprising SEQ ID No: 2, or a fragment thereof, optionally having laccase activity; b) a polynucleotide sequence having at least about 20% to 99.99% identity to a polynucleotide sequence encoding a polypeptide comprising SEQ ID No: 2 or a fragment of SEQ ID NO: 2, wherein said polynucleotide encodes a polypeptide or fragment thereof has laccase activity; c) a polynucleotide sequence encoding a fragment of a polypeptide comprising SEQ ID No: 2, wherein said fragment has laccase activity; d) a polynucleotide sequence comprising SEQ ID NO: 1; e) a polynucleotide sequence having at least about 20% to 99.99% identity to the polynucleotide sequence of SEQ ID NO: 1) a polynucleotide sequence encoding variant (e.g., a variant polypeptide) of the polypeptide of SEQ ID No: 2, wherein said variant has laccase activity; or f) a polynucleotide sequence encoding a fragment of a variant polypeptide as set forth in (e). Genetic constructs of the subject invention can also contain additional regulatory elements such as promoters and enhancers and, optionally, selectable markers. In one aspect of the subject invention, the genetic construct comprises a promoter operably linked to a polynucleotide sequence encoding SEQ ID NO: 2.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and a transcriptional and translational termination regions.

Another aspect of the invention provides vectors for the cloning and/or the expression of a polynucleotide sequence taught herein. Vectors of this invention, including vaccine vectors, can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide, peptide, fragment, or variant encoded by a polynucleotide sequence disclosed herein comprising the culture of a host cell transformed with a polynucleotide of the subject invention under conditions that allow for the expression of the polypeptide and, optionally, recovering the expressed polypeptide.

One aspect of the invention provides for methods of oxidizing a phenolic substrate comprising contacting the polypeptide as described herein, or fragments thereof retaining laccase activity, with a substrate comprising phenolic compounds under conditions that allow for the oxidation of the phenolic compounds. Examples of the phenolic substrates include 2,6-dimethoxyphenol (DMP) and 4-hydroxy-3,5-dimethoxybenzaldehyde azine (syringaldazine or SGZ). Wine is another source of phenolic substrates that can be oxidized by the disclosed laccase. In one aspect, the contacting step can be performed by adding a composition comprising the purified laccase as described herein, or fragments thereof retaining laccase activity, to the phenolic compounds. The contacting step can be performed in the presence of other materials, such as salts and buffers. Additionally, the oxidation process can be optimized on specific substrate by manipulating the reaction conditions including temperature, pH, salt, and dissolved oxygen.

In another embodiment, the subject polypeptide, or fragments thereof retaining laccase activity, is capable of oxidizing bilirubin to biliverdin and water, which is desirable for a variety of clinical applications. In plasma samples, bilirubin interferes with adsorption bands between 400 and 500 nm. Addition of the polypeptide to plasma samples diminishes interference enables quantification of molecules at 400 to 500 nm such as plasma hemoglobin at 415 nm.

In yet another embodiment, the polypeptide of SEQ ID NO: 2, or fragments thereof retaining laccase activity, is able to mediate the delignification and detoxification of acid-pretreated biomass. Simultaneous saccharification and fermentation of hemicellulosic biomass is limited by the toxic compounds generated during the biomass pretreatment that restrict activity of the saccharifying enzymes and productivity of the microbial biocatalysts. Likewise, steps taken to optimize the modification of lignin by enzymes could bypass the need for harsher pretreatment steps and thereby facilitate bioprocess consolidation. Thus, the subject invention provides methods of delignification and detoxification of acid-pretreated biomass comprising contacting acid-pretreated biomass with a laccase comprising SEQ ID NO: 2, or fragments thereof retaining laccase activity.

In another aspect of the invention, the laccase of SEQ ID NO: 2, or fragments thereof retaining laccase activity, can be used for bleaching of dye in solutions. Such a method comprises contacting the dye with the laccase comprising SEQ ID NO: 2 within the solution.

Yet another aspect of the invention provides methods of bleaching pulp for paper production that comprises contacting paper pulp with a laccase comprising SEQ ID NO: 2, or fragments thereof retaining laccase activity. Alternatively, the disclosed laccase can be used in methods of lignin modification (e.g. in the manufacture of wood composites, such as wood fiber materials such as chipboards, fiber boards, or particle boards, or in the manufacture of laminated wood products, such as laminated beams and plywood) comprising contacting a lignin with a laccase comprising SEQ ID NO: 2, or fragments thereof retaining laccase activity.

An additional aspect of the invention comprises the treatment of waste water from: chemical or pharmaceutical factories; dye manufacturing facilities or dye-works; textile facilities or pulp production facilities. This aspect of the invention comprises contacting waste water from such facilities with a laccase comprising SEQ ID NO: 2, or fragments thereof retaining laccase activity.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

MATERIALS AND METHODS

Materials

Biochemicals were from Sigma-Aldrich (St. Louis, Mo.). Other organic and inorganic analytical grade chemicals were from Fisher Scientific (Atlanta, Ga.). Restriction endonucleases, T4 DNA ligase and Vent DNA polymerase were from New England. Biolabs (Ipswich, Mass.). AccuPrime GC-rich DNA polymerase was from Invitrogen (Carlsbad, Calif.). Desalted oligonucleotides were from Integrated DNA Technologies (Coralville, Iowa). Agarose for routine analysis of DNA was from BioRad Laboratories (Hercules, Calif.). SeaKem GTG agarose used for separation and isolation of DNA fragments prior to ligation was from FMC Bioproducts (Rockland, Me.).

Strains, Media and Plasmids

Strains, primers and plasmids are summarized in Table 1. *Escherichia coli* DH5α was used for routine recombinant DNA experiments, and *E. coli* GM2163 was used to generate plasmid DNA for transformation of *Hfx. volcanii* (Dyall-Smith, 2008). *E. coli* strains were grown at 37° C. in Luria-Bertani medium. *Hfx. volcanii* strains were grown at 42° C. in complex (ATCC 974 and yeast-peptone-Casamino Acids) and lactate-minimal medium (Hv-LMM). Hv-LMM included 2.46 M NaCl, 84 mM MgCl$_2$·6H$_2$O, 84 mM MgSO$_4$·7H$_2$O, 56 mM KCl, 6 mM CaCl$_2$·2H$_2$O, 5 mM NH$_4$Cl, 4.6 mM NaBr, 1.4 mM NaHCO$_3$, 9.75 mM KPO$_4$ pH 7.5, 30 mM Tris pH 7.5, 0.25% (v/v) DL-lactic acid, 14 mM succinic acid, 0.0255% (v/v) glycerol, 1.8 nM MnCl$_2$·4H$_2$O, 1.5 nM ZnSO$_4$·7H$_2$O, 8.28 nM FeSO$_4$·7H$_2$O, 100 μM CuSO$_4$·5H$_2$O, 66 μg·ml$^{-1}$ histidine, 51 μg·ml$^{-1}$ each of leucine, methionine, tryptophan, glycine, DL-pantothenic acid and uracil, 41 μg·ml$^{-1}$ each of thymidine and hypoxantine, 800 ng thiamine and 100 ng D-biotin. Ampicillin (0.1 mg·ml$^{-1}$), novobiocin (0.1 μg·ml$^{-1}$), and CuSO$_4$ (50 to 500 μM) were included as needed. Cultures were grown in liquid (150 to 200 rpm) and solid medium (15% [w/v] agar plates).

Genome Analysis

NCBI Local BlastP (Altschul et al., 1997) with BioEdit sequence editor software v7.0.4.1 (Hall, 1999) was used to compare the theoretical *Hfx. volcanii* DS2 proteome See Worldwide Website: archaea.ucsc.edu/, April 2007 version) (Hartman et al., 2009) to fungal and bacterial proteins with known laccase activity. Laccase protein sequences included phenol oxidase A of the ligno-cellulolytic ascomycete *Stachybotrys chartarum* (Mander et al., 2006), spore coat protein A (CotA) from *Bacillus subtilis* (Martins et al., 2002) and polyphenoloxidase (PPO) from *Streptomyces lavendulae* (Suzuki et al., 2003). Phylogenetic and molecular evolutionary analyses of the primary sequences of proteins were conducted using MEGA v3.1 (Kumar et al., 2004). Pairwise and multiple sequence alignment was performed using Clustal W (Thompson et al., 1994). Non-conserved regions in the N- and C-termini were excluded from the alignment. Evolutionary distances were estimated from the protein sequences using the proportion (p-) distance substitution model. Consensus tree inference was by neighbor joining with bootstrap phylogeny test (1000 replicates; seed number for bootstrap, 64238) and pairwise gap deletion. TatP v1.0 (Bendtsen et al., 2005), TATFIND v1.4 (Rose et al., 2002) and EnsembleGly (Caragea et al., 2007) servers were used for prediction of twin arginine translocation (TAT) and glycosylation motifs in the LccA protein (see FIG. 7).

DNA Isolation, Analysis and Strain Construction

*Hfx. volcanii* DS70 genomic DNA (a strain of DS2 cured of plasmid pHV2) (Wendoloski et al., 2001) was prepared for polymerase chain reaction (PCR) by transfer of isolated colonies to 30 μl deionized H$_2$O using toothpicks. Cells were boiled (5 min), and the resulting lysate was chilled on ice (10 min) and centrifuged (14,000×g; 10 min at 4° C.). Supernatant (5-10 μl) was used as template for PCR with primer pairs specific for the *Hfx. volcanii* laccase gene (lccA, HvoB0205), as listed in Table 1. A mixture of AccuPrime GC-Rich and Vent DNA polymerase at a 9:1 ratio was used for PCR with buffer and nucleotide concentrations according to Invitrogen. PCR was performed with an iCycler (BioRad Laboratories), and sizes of products were analyzed by electrophoresis using 0.8% (w/v) agarose gels in TAE buffer (40 mM Tris acetate, 2 mM EDTA, pH 8.5) with Hi-Lo DNA molecular weight markers as standards (Minnesota Molecular, Minneapolis, Minn.). Gels were photographed after staining with ethidium bromide at 0.5 μg·ml$^{-1}$ with a Mini visionary imaging system (FOTODYNE, Hartland, Wis.). PCR generated-DNA fragments of appropriate size for the lccA gene (1.8 kb) were isolated from 0.8% (w/v) SeaKem GTG agarose (FMC Bioproducts, Rockland, Me.) gels in TAE buffer using the QIAquick gel extraction kit (Qiagen) and ligated into the NdeI to HindIII sites of pET24b to generate plasmid pJAM821 and pJAM823 for expression of the lccA gene in recombinant *E. coli* Rosetta (DE3). In addition, the lccA gene was excised from plasmids pJAM821 and pJAM823 and ligated into the NdeI to BlpI sites of a *Hfx. volcanii* shuttle vector (pJAM202) to position the lccA gene downstream of a constitutive ribosomal RNA promoter P2. These expression plasmids (pJAM822 and pJAM824) were transformed into *Hfx. volcanii* 1126 to generate strain SB01 and US02 for high-level synthesis of lccA with and without a C-terminal strepII tag (-WSHPQFEK), respectively. Plasmid DNA was isolated using the QIAprep Spin Miniprep Kit (Qiagen, Valencia, Calif.), and the fidelity of cloned DNA sequences and the 100% identity of lccA genes from DS2 and DS70 strains were confirmed by Sanger DNA Sequencing (ICBR Genomics Facility, University of Florida).

Enzyme Purification

*Hfx. volcanii* SB01 and US02 cells were grown in media supplemented with 100 μM CuSO$_4$ (LMM or YPC; 25 ml per 125-ml Erlenmeyer flask) and harvested by centrifugation (15,000×g; 20 min at 4° C.). Culture broth was filtered by 3 MM Whatman chromatography paper. Protein was concentrated by gradual addition of one volume of cold absolute ethanol, incubation on ice (1 h) and centrifugation (7,000×g at 4° C., 10 min). The resulting precipitate was suspended in 25 mM Tris-HCl buffer at pH 8.4 (T buffer) to ⅕ original sample volume and recentrifuged to eliminate insoluble material. US02 precipitate (from an original culture of 360 ml) was concentrated to 3 ml using a Centricon PL-30 centrifugal filter according to the instructions of the supplier (Millipore, Billerica, Mass.) and separated into two 1.5-ml fractions (where F1 and F2 represent the more viscous lower and upper fractions, respectively) and diluted 6.7-fold with T buffer. For both SB01 and US02 samples, proteins were filtered (0.20 μm) immediately prior to application to an anion-exchange MonoQ HR 5/5 or 10/10 column (Pharmacia) equilibrated with T buffer, as indicated in Table 1. Elution was carried out with a linear NaCl gradient (0 to 1 M in 1 ml T buffer) with fractions containing peak activity at 625 to 675 mM NaCl. Additional steps were included for purification of LccA from SB01, including application of active fractions (0.25 ml per run) to a Superdex 200 HR 10/30 column (Pharmacia) equilibrated in T buffer with 150 mM NaCl, followed by a MonoQ HR 10/10 column (Pharmacia) equilibrated in T buffer and developed with a linear NaCl gradient (600 to 800 mM in 1 ml T buffer). Fractions were monitored for purity by assay with 4-hydroxy-3,5-dimethoxybenzaldehyde azine (syringaldazine [SGZ]) under standard assay conditions (see below for details) and staining with Coomassie blue R-250 after separation by reducing 12% SDS-PAGE according to Laemmli (1970). Prestained SDS-PAGE standards and Kaleidoscope standards (BioRad) were used as protein standards for PAGE. They included: phosphorylase B (100.9 kDa), bovine serum albumin (97.3), ovalbumin (54.1 kDa), carbonic anhydrase (37.6 kDa), soybean trypsin inhibitor (29.2 kDa), lysozyme (20.0 kDa). Native molecular mass was determined by applying samples to a calibrated Superose 200 HR 10/30 column as recommended by supplier (Pharmacia). Molecular mass standards for gel filtration calibration included: cytochrome c (12.4 kDa), carbonic anhydrase (29 kDa), bovine serum albumin (66 kDa), alcohol dehydrogenase (150 kDa), β-amylase (200 kDa) and apoferritin (443 kDa) (Sigma). Samples were stored in the presence of oxygen at 4° C.

Enzyme Activity and Protein Estimation

Substrates for enzyme activity assay included 2,2'-azino-bis-3-ethylbenzthiazoline-6-sulphonic acid (ABTS) (Sigma; A1888), 2,6-dimethoxyphenol (DMP) (Sigma; D135550), 2-methoxyphenol (guaiacol) (Sigma; G5502), 4-hydroxy-3,5-dimethoxybenzaldehyde azine (syringaldazine or SGZ) (Sigma; S7896), bilirubin (Sigma; B4126), and ferrous ammonium sulfate. Enzyme activity was determined by change in absorbance, in triplicate, by UV/Visible-spectroscopy using a BioTek Synergy HT multi-detection microplate reader with a 96-well plate. Oxidation of substrate was monitored by absorbance increase (ABTS at 420 nm with $\epsilon=36,000$ M$^{-1}$ cm$^{-1}$; SGZ at 526 nm with $\epsilon=65,000$ M$^{-1}$ cm$^{-1}$; DMP at 468 nm with $\epsilon=49,000$ M$^{-1}$ cm$^{-1}$; guaiacol at 436 nm with $\epsilon=26,600$ M$^{-1}$ cm$^{-1}$; ferrous ammonium sulfate at 315 nm with $\epsilon=2,200$ M$^{-1}$ cm$^{-1}$) or decrease (bilirubin at 440 nm with $\epsilon=56,300$ M$^{-1}$ cm$^{-1}$). Standard assay conditions were 185 mM NaCl at 45° C. with the following buffers and substrate concentrations: 100 mM sodium acetate buffer at pH 6.0 for ABTS (at 5 mM), DMP (at 2 mM) and guaiacol (at 5 mM); 25 mM Tris-HCl buffer at pH 8.4 for SGZ (at 1 mM); and 200 mM Tris-HCl buffer at pH 8.4 for bilirubin (0.45 mM). Copper sulfate (1 mM) was included for assay of DMP oxidation. Oxidation of ferrous ammonium sulphate (1 mM) was monitored at 315 nm ($\epsilon=2,200$ M$^{-1}$ cm$^{-1}$) with and without salt (185 mM NaCl) in 100 mM MES (morpholineethanesulfonic acid) buffer at pH 5 as well as 25 mM Tris-HCl buffer at pH 7.0 and 8.4. One unit of enzyme activity is defined as the amount of enzyme that oxidizes 1 μmol of substrate per min at standard conditions. Kinetic studies were conducted using purified LccA at a final concentration of 0.61 μg·ml$^{-1}$ with 5 to 160 μM of SGZ, 50 to 1,250 mM ABTS, and 90 to 540 μM bilirubin. Kinetic parameters ($K_m$, $V_{max}$, and $k_{cat}$) were determined using the Michaelis-Menten equation. Protein concentration was determined according to Bradford (1976) using a Bio-Rad protein assay with bovine serum albumin as a standard (BioRad Laboratories). All assays and protein purifications were performed at least in triplicate.

For detection of laccase activity in gel, non-boiled samples were separated by 7.5% PAGE gels devoid of SDS and β-mercaptoethanol. Gels were immersed in either T buffer containing 1 mM SGZ activity was rapidly visualized as a pink color. For detection of total protein, gels were counterstained in Coomassie blue R-250 stain and destained according to instructions of the supplier (BioRad). Images of activity and protein staining were acquired using a VersaDoc 1000 imaging system (BioRad).

Mass Spectrometry (MS) Analysis

Purified LccA was provided for MS analysis as an in-solution sample and as protein bands separated by reducing SDS-PAGE (7.5%). Gels were stained with Biosafe Coomassie (BioRad), and LccA-protein bands (71 kDa) were excised from the gel and destained with 100 mM NH$_4$HCO$_3$ (pH 7.5) in 50% (v/v) acetonitrile (4° C. overnight). Protein samples were reduced, alkylated in gel or in solution, digested with a 1:20 mg ratio of trypsin (Promega) to protein (18 to 24 h, 37° C.) and desalted with a PepMap C18 cartridge. Peptides were further separated by capillary reverse-phase high-performance liquid chromatography (RP HPLC) using a PepMap C$_{18}$ column (15 cm×75 μm inside diameter [i.d.]) and an Ultimate Capillary HPLC System (LC Packings, San Francisco, Calif.) with a linear gradient of 5% to 40% (v/v) acetonitrile for 25 min at 200 nl/min. Tandem MS (MS-MS) analysis was performed online using a hybrid quadrupole time-of-flight instrument (QSTAR XL hybrid LC/MS/MS) equipped with a nanoelectrospray source (Applied Biosystems, Foster City, Calif.) and operated with the Analyst QS v1.1 data acquisition software. Spectra from all experiments were converted to DTA files and merged to facilitate database searching using the Mascot search algorithm v2.1 (Matrix Science, Boston, Mass.) against the theoretical HA volcanii proteome (http://archaea.ucsc.edu/, April 2007 version). Search parameters included trypsin as the cleavage enzyme and carbamidomethylation as a fixed modification. Variable modifications included deamidation of asparagine and glutamine, oxidation of methionine, methyl-esterification of aspartate and glutamate, and N-acetylation and phosphorylation of serine, threonine and tyrosine. Mass tolerances for all QSTAR analyses were 0.3 Da, and peptides with assigned probability-based Mascot ion scores less than 30 were excluded.

N-Terminal Sequence Analysis of Protein

Purified LccA was separated by reducing 12% SDS PAGE and transferred by electroblotting to Immobilon-P (PVDF) membranes (Amersham Biosciences) at 100 V for 100 min at 4° C. Proteins were stained in membrane with 0.2% (w/v) Coomassie blue R-250 in 40% acetic acid for 30 sec and rinsed with deionized water. The LccA-specific protein band was excised and subjected to automated Edman degradation for N-terminal sequencing (Edman, 1970).

Glycoprotein Analysis

LccA was separated by reducing SDS-PAGE and stained in gel for glycosylation using Pro-Q Emerald 300 (Invitrogen P21857) and total protein was separated using Sypro Ruby (BioRad; 1703126) with a VersaDoc 4000 imaging system according to the instructions of the manufacturer (BioRad Laboratories). The carbohydrate content of purified LocA was estimated by the colorimetric method of Dubois et al. (Dubois et al., 1956) using glucose as a standard. Pure LccA was deglycosylated by the trifluoromethanesulfonic acid (TFMS) method (Edge et al., 1981) for 0 to 10 hours on ice and analyzed by reducing SDS-PAGE. *Trametes versicolor* laccase (Sigma Fluka; 53739) and bovine carbonic anhydrase (Sigma-Aldrich; C7025) were included for glycoprotein analysis as positive and negative controls, respectively.

Example 1

LccA is Related to Laccases of the Multicopper Oxidase Family

Figure 7:
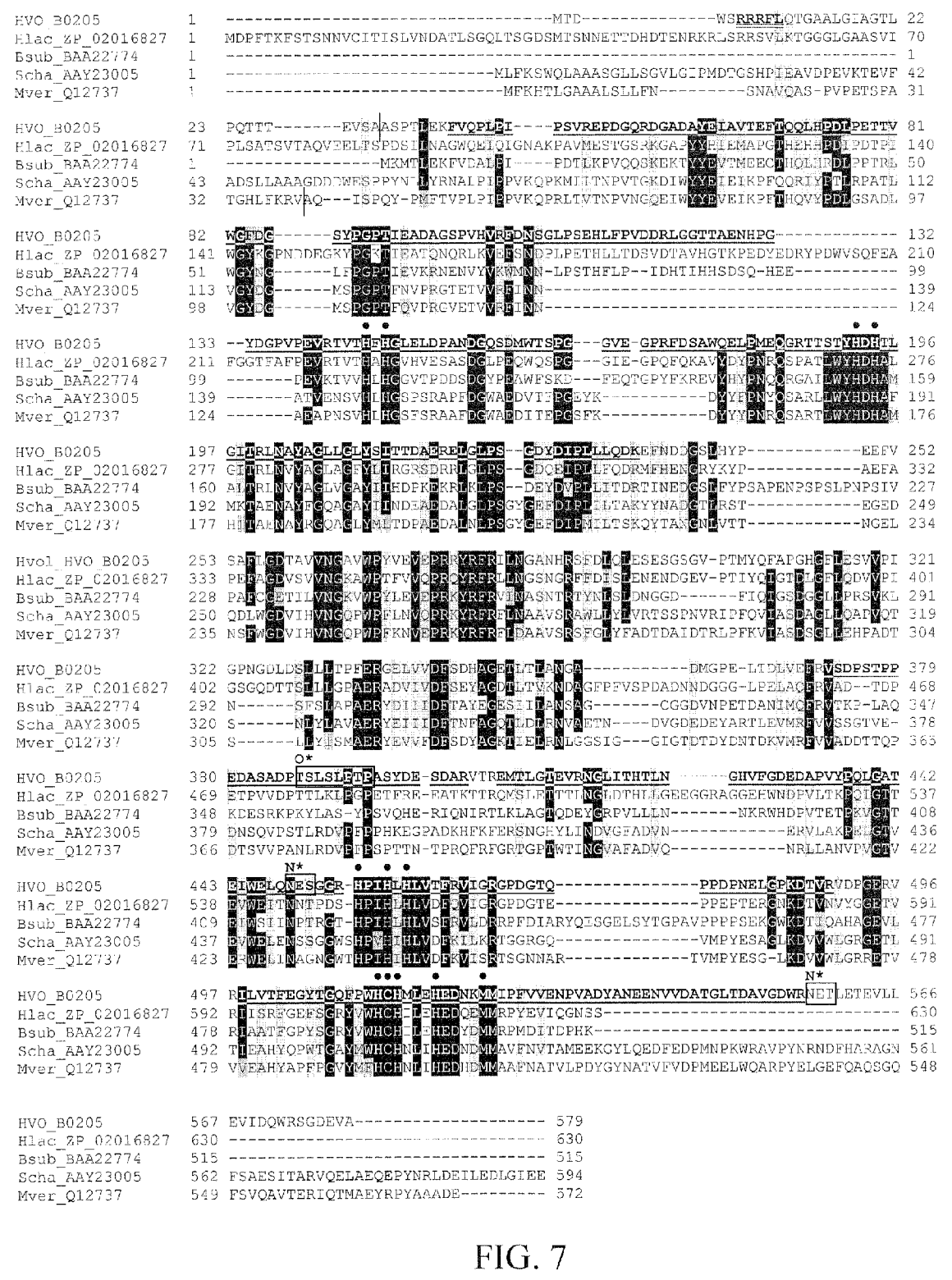

Basic local alignment search tool (BLAST) analysis of the *Hfx. volcanii* genome revealed a 63,397 Da-polypeptide of pI 4.34 (Hvo_B0205; designated as LccA in this study) related to laccases of the multicopper oxidase (MCO) family. The gene locus encoding LccA resided on pHV3 (440 kb), one of three large replicons with cdc6- and orc1-associated replication origins separate from the 2.848-Mb chromosome (Norais et al., 2007). Proteins that cluster to the MCO family are rare in archaea with only a few examples, all of which remain to be characterized. The one cysteine and 10 histidine residues required for coordination of the Type 1, 2 and 3 copper centers of blue copper laccases were highly conserved in the *Hfx. volcanii* LccA (FIG. 7) suggesting this protein may catalyze the oxidation of phenolic compounds. The *Hfx. volcanii* LccA was also predicted to be secreted by the twin-arginine translocation (TAT) system, based on a N-terminal twin arginine motif (SRRRFL) preceding a hydrophobic patch. LccA was also predicted to be cleaved between Ala31 and Ala 32 to generate a mature protein of 60.1 kDa and to be glycosylated based on the presence of O- and N-linked glycosylation motifs, Thr-X$_5$-Pro-X-Pro and Asn-X-(Thr/Ser) (where X represents any amino acid) (FIG. 7).

Figure 1B:
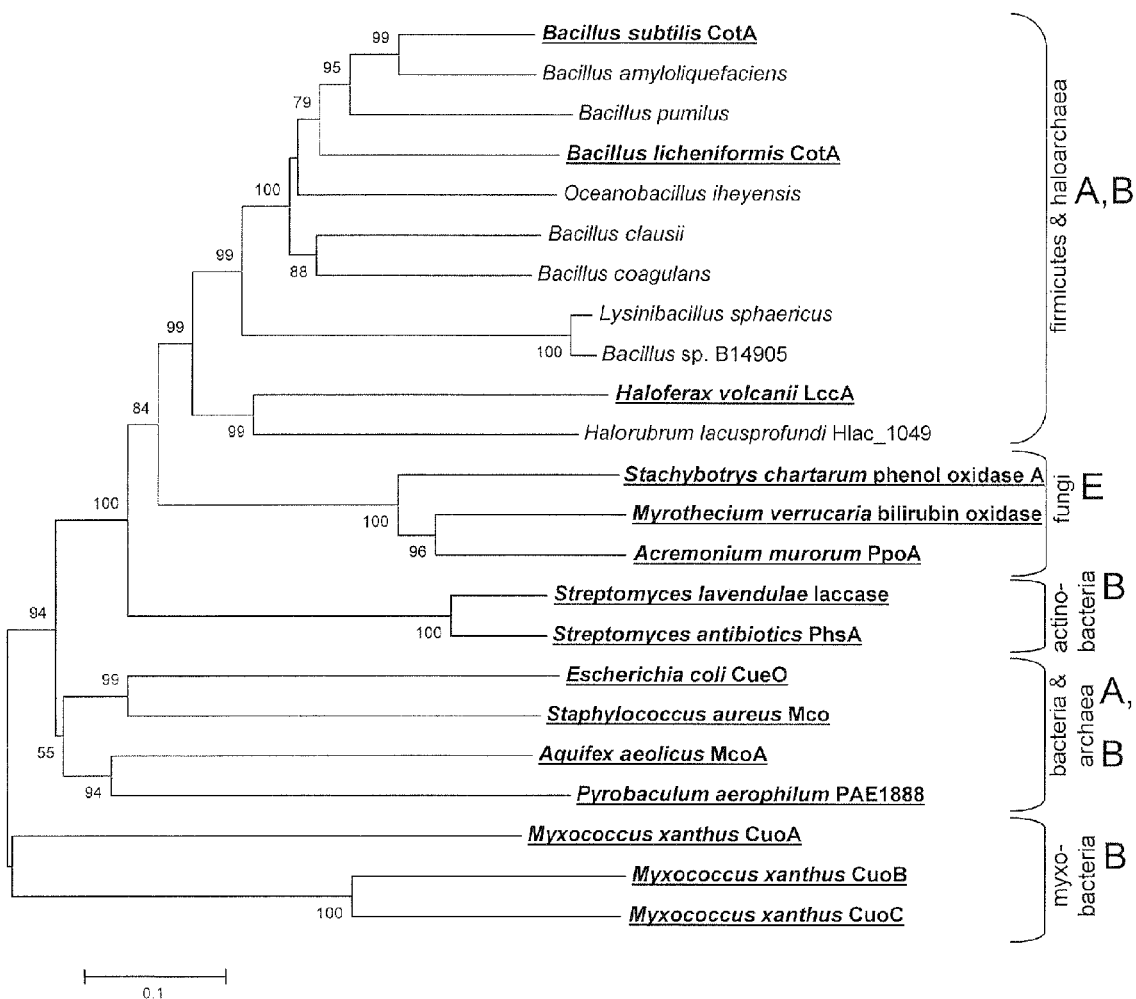
FIG. 1B. Phylogenetic comparison of *H. volcanii* LccA to laccases and other multicopper oxidase protein sequences. Proteins with associated biochemical, microarray and/or physiological studies are underlined and in bold. Origin of protein sequences used for the analysis with corresponding accession numbers and references were as follows: *H. volcanii* DS2 (HVO_B0205, LccA this study), *Acremonium murorum* (polyphenol oxidase or PpoA, Q9P8C3), *Aquifex aeolicus* (McoA, AAC07157.1), *Bacillus amyloliquefaciens* FZB42 (A7Z229), *Bacillus clausii* KSM-K16 (QSWEM6), *Bacillus coagulans* 36D1 (A2U4V3), *Bacillus licheniformis* DSM 13/ATCC 14580 (Q65MU7), *Bacillus pumilus* SAM-032 (A8FAG9), *Bacillus subtilis* (P07788, CotA), *Bacillus* sp. B14905 (A318L4), *Escherichia coli* (P36649.2, CueO), *Halorubrum lacusprofundi* ATCC 49239 (ACM56646, Hlac__1049), *Lysinibacillus sphaericus* C3-41 (B1HU92), *Myrothecium verrucaria* (Q12737, billirubin oxidase), *Oceanobacillus iheyensis* (Q8CXJ7), *Pyrobaculum aerophilum* (AAL63794.1, PAE1888), *Stachybotrys chartarum* (Q4ZIR9), *Staphylococcus aureus* (Q69HT9, Mco), *Streptomyces antibioticus* (Q53692, phenoxazinone synthase or PhsA) and *Streptomyces lavendulae* REN-7 (laccase, Q8 GB87). *Myxococcus xanthus* (Q1D6V6, CuoA; Q1D6V1, CuoB; Q1D6U4, CuoC) served as an outgroup for this analysis.

Although an ORF closely related to the *Hfx. volcanii* LccA was present in the draft genome of the haloarchaeon *Halorubrum lacusprofundi* (HlacDRAFT_2279), LccA homologs were not universal among the haloarchaea and were absent from the genomes of *Halobacterium* sp. NRC-1 (*Hb. salinarum* R1) (Ng et al., 2000), *Haloquadratum walsbyi* DSM 16790 (Bolhuis et al., 2006), *Haloarcula marismortui* ATCC 43049 (Baliga et al., 2004) and *Natronomonas pharaonis* DSM 2160 (Falb et al., 2005). Based on consensus tree inference (FIGS. 1A and 1B), the *Hfx. volcanii* LccA was closely related to MCO proteins of the gram-positive firmicutes, including CotA proteins of *B. subtilis* and *Bacillus licheniformis*, which have demonstrated thermostable laccase activity (Martins et al., 2002; Koschorreck et al., 2008). Among the archaea, LccA was closely related (45% identity) only to Hlac_1049, encoded on the main chromosome of *Halorubrum lacusprofundi*. Other archaeal genomes (completed as of November 2009) did not encode LccA homologs, including the haloarchaea *Halobacterium* sp. NRC-1 (*Halobacterium salinarum* R1). *Haloquadratum walsbyi* DSM 16790, *Haloarcula marismortui* ATCC 43049, and *Natronomonas pharaonis* DSM 2160. The *Hfx. volcanii* LccA was distinct, however, from an MCO of the hyperthermophilic archaeon *Pyrohaculum aerophilum*, PAE1888, an uncharacterized protein with enhanced transcript leels under denitrifying conditions in of *P. aerophilum* (Cozen et al., 2009). PAE1888 clusters instead with McoA of *Aquiftx aeolicus*, CueO of *E. coli* and Mco of *Staphylococcus aureus*. All three of these latter bacterial MCOs have catalytic and/or genetic properties consistent with their proposed role in oxidative stress and/or copper and iron homeostasis (e.g., Singh et al., 2004; Fernandes et al., 2007; Sitthisak et al., 2005). This includes a higher enzyme specificity ($k_{cat}/K_m$) for cuprous and ferrous iron than for aromatic substrates and aromatic oxidation activity that requires addition of copper (Solano et al., 2001). Consistent with this, the methionine-rich helix proposed to be involved in metal sequestration that lies over the type 1 sites of the metal-oxidizing MCOs, such as *E. coli* CueO (Roberts et al., 2002), is not conserved in LccA. The sparse distribution of laccase gene homologs among the archaea and the close relationship of LccA to laccases of the firmicutes (e.g., *B. subtilis* CotA), suggest that lccA was acquired by horizontal gene transfer from the Bacteria domain and that it encodes a laccase that oxidizes phenolic compounds.

Example 2

Laccase Activity in the Culture Broth of *Hfx. Volcanii*

The initial efforts focused on engineering the *Hfx. volcanii* lccA gene for production of the LccA protein in recombinant *E. coli* Rosetta (DE3) with plasmids pJAM821 and pJAM823 (Table 1) using the pET expression system. Although numerous *Hfx. volcanii* proteins have been successfully produced using this type of bacterial system (Kaczowka et al., 2003; and Reuter et al., 2004), LccA protein and laccase activity, however, were not detected in either the culture broth or cell lysate of this *E. coli* strain as determined by SDS-PAGE and SGZ oxidation assay, respectively (data not shown). The undetectable levels of LccA may be due to a number of factors. TAT substrates, "salt-loving" haloarchaeal proteins, enzymes with elaborate metal clusters, and glycoproteins are all notoriously difficult to produce in an active form at high-levels in conventional expression systems, such as *E. coli* and *Saccharomyces cerevisiae* (Connaris et al., 1999; Madzak et al., 2005; Brüser, 2007).

Figure 2A:
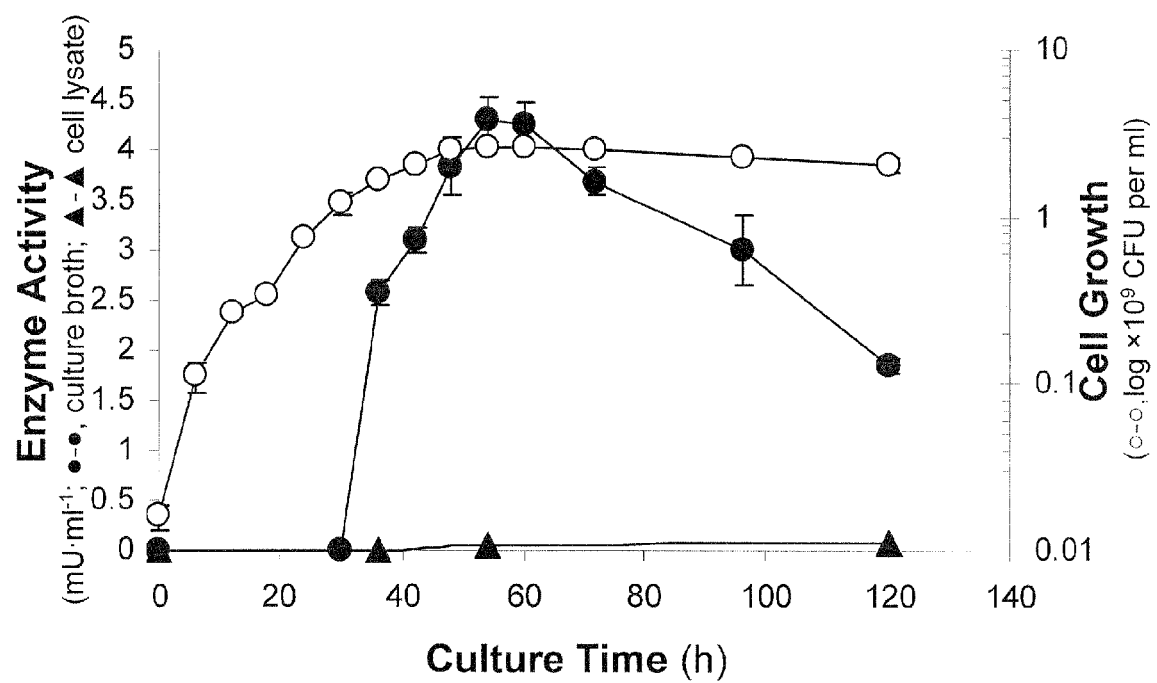
FIG. 2A shows laccase activity of *Hfx. volcanii* SB01 cultures at various stages of growth. *Hfx. volcanii* SB01 cells were inoculated to a final $OD_{600}$ of 0.01 in Hv-LMM supplemented with 0.1 µg per ml novobiocin and 100 µM copper sulfate. Cells were grown for 120 h at 42° C. in an orbital shaker (150-200 rpm). Samples were withdrawn at periodical intervals and used for estimation of growth (1 $OD_{600}$ unit~1× $10^9$ CFU per ml) and laccase activity. For analysis of cell lysate, cells were pelleted by centrifugation (for 10 min at 10,000×g and 4° C.), washed twice in T buffer supplemented with 2 M NaCl, resuspended in T buffer and lysed by sonication (15 s on, 45 s off at 20% amplitude for 3 min). Culture broth and cell lysate were assayed for laccase (SGZ oxidizing) activity under standard conditions.
Figure 2B:
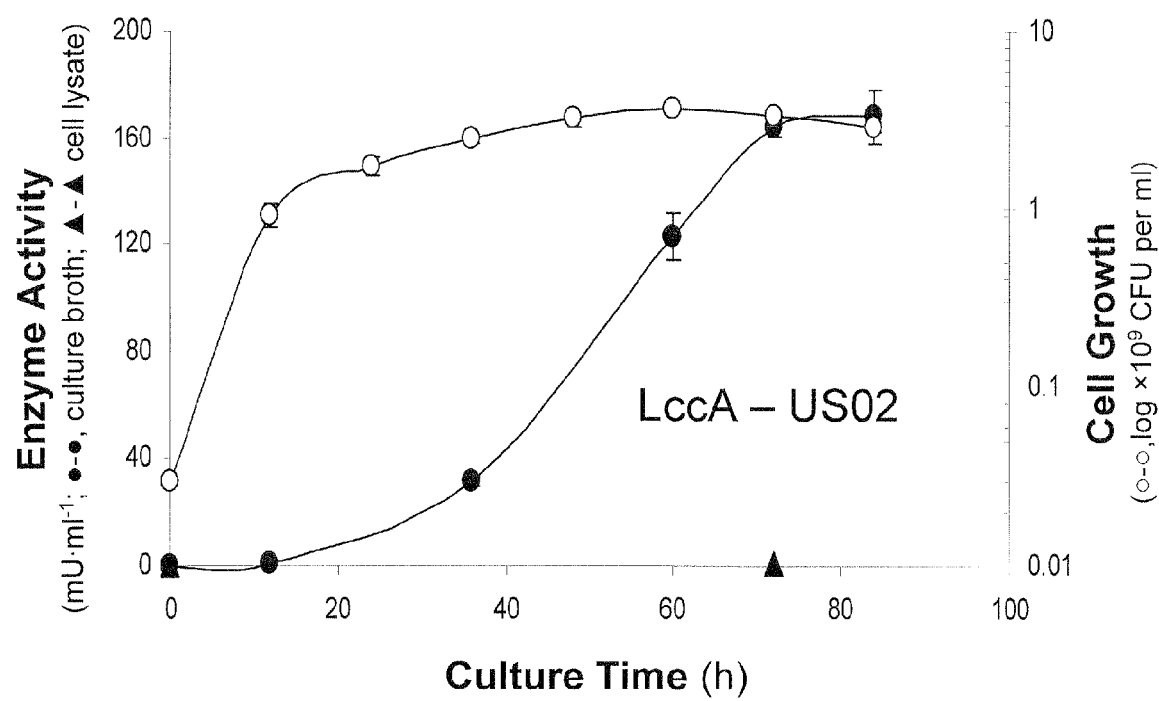
FIG. 2B shows laccase activity of *H. volcanii* US02 strains at various stages of growth. *H. volcanii* US02 and parent H26 (data not shown) were inoculated to a final $OD_{600}$ of 0.01 in medium supplemented with novobiocin and 100 µM copper sulfate. LMM and YPC were optimal for production of laccase activity for US02. Cells were grown for up to 120 h at 42° C. in an orbital shaker (150-200 rpm). Samples were withdrawn at periodical intervals and used for estimation of growth (1 $OD_{600}$ unit~1×$10^9$ CFU per ml) and assay of laccase activity. For analysis of cell lysate, cells were harvested by centrifugation (10 min at 10,000×g and 4° C.), washed twice in T buffer supplemented with 2 M NaCl, resuspended in T buffer and lysed by sonication (15 s on, 45 s off at 20% amplitude for 3 min). Culture broth (filtered by 0.4 µm) and cell lysate were assayed for laccase (SGZ oxidizing) activity under standard conditions.

To overcome the difficulties of producing LccA in *E. coli*, the native host (i.e., *Hfx. volcanii*, known for its halophilic properties and robust TAT system (Rose et al., 2002) was engineered for enhanced expression of lccA. Multicopy plasmids (pJAM822 and pJAM824) with a pHV2 origin of replication, ribosomal RNA P2 promoter and T7 transcriptional terminator were used for this lccA gene-expression. In particular, the lccA gene was positioned downstream of a strong rRNA P2 promoter on a multicopy plasmid (pHV2 based) with and without coding sequence for a 1-Da C-terminal StrepII tag (—WSHPQFEK), and the resulting plasmids were transformed into *H. volcanii* H26. The resulting strains, *Hfx. volcanii* SB01 and US02 (Table 1), were grown in various media supplemented with $CuSO_4$ (50 to 500 μM) and compared to their parent (H26) for the production of laccase activity by monitoring the oxidation of SGZ. Using this approach, laccase activity associated with *H. volcanii* cells was negligible for all three strains examined reaching at most $0.69\pm0.12$ mU·ml$^{-1}$ after 80-120 h of growth (FIGS. 2A and 2B). In contrast to these cellular fractions, significant levels of laccase activity were detected in the culture broth of *H. volcanii* SB01 and US02 with the highest level of activity detected for strain US02 in YPC medium with 100 μM $CuSO_4$ (FIG. 2B). Under these conditions, the laccase activity of US02 reached a maximum of $170\pm10$ mU·ml$^{-1}$ at stationary phase (72 to 80 h); whereas, the level of laccase activity secreted by SB01 was 40-fold lower reaching levels of only $4.3\pm0.23$ mU·ml$^{-1}$ at 54 h. Laccase activity was not detected in the culture broth of US02 and SB01 until stationary phase (FIGS. 2A and 2B) and was not detected at significant levels throughout all phases of growth for parent strain. H26 (data not shown). The reason for the lag in laccase productivity for US02 and SB01 remains to be determined; however, a similar time course has been observed for the secretion of the *Natrialba magadii* subtilisin-like Nep protease from recombinant *H. volcanii* (De Castro et al., 2008). While the addition of a strong, relatively constitutive promoter upstream of lccA enhanced laccase productivity by over 170-fold, addition of a C-terminal StrepII coding sequence significantly decreased LccA productivity. Thus, enhanced expression of lccA coding sequence alone was optimum for secretion of laccase activity by *H. volcanii*.

Although the genetic systems of archaea are not as advanced as those of bacteria or yeast, the productivity of the engineered *H. volcanii* strain US02 was surprisingly high, with 170 mU·ml$^{-1}$ laccase activity produced in the medium in less than 3 days. This level of productivity is comparable to that of yeast systems, such as *Yarrowia lipolytica* and *Pichia methanolica* systems, developed for secretion of the laccase of *Trametes versicolor* (a white-rot fungus). Typically, these yeast systems require 5 to 6 days of cultivation for production of 230 to 1,260 mU·ml$^{-1}$ of laccase activity (Jolivalt et al., 2005; Guo et al., 2006). Secretion of LccA, contrasts with the vast majority of recombinant systems for production of bacterial laccase/MCO enzymes which are based on enzyme purification from the soluble and/or insoluble fractions of recombinant *E. coli* cells, such as those used for *Thermus thermophilus* Tth-laccase (Miyazaki 2005), *Bacillus subtilis* and *Bacillus licheniformis* CotA (Martins et al., 2002; Koschorreck et al., 2008), *Bacillus halodurans* Lbhl (Miyazaki 2005), *Staphylococcus aureus* Mco (Sitthisak et al., 2005), *Aquifex aeolicus* McoA (Fernandes et al., 2007), and *Bacteroides* RL5 from the rumen metagenome (Beloqui et al., 2006).

Example 3

Purification of LccA from the Culture Broth of *Hfx. Volcanii*

Purification of LccA from Culture Broth of *Hfx. Volcanii* SB01

Figure 3A:
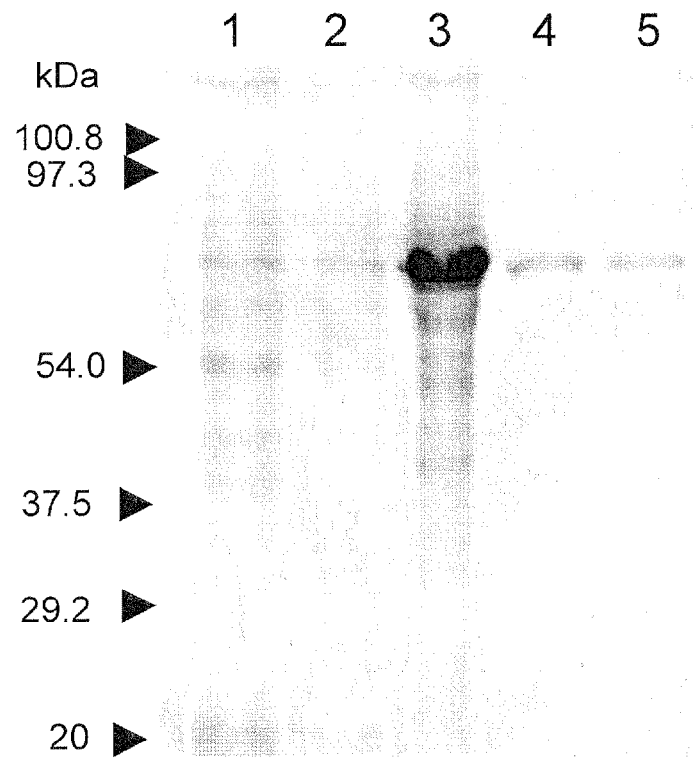
FIGS. 3A-3B show LccA purified to electrophoretic homogeneity from the culture broth of *Hfx. volcanii* SB01. a) SDS PAGE gel of LccA at various stages of purification from *Hfx. volcanii* SB01. Molecular standards indicated on left. Culture broth (lane 1), ethanol precipitate (lane 2), MonoQ 5/5, pH 8.4 fractions (lane 3), Superdex 200 HR 10/30 fractions (lane 4), MonoQ 10/10, pH 8.4 fractions (lane 5); b) Native gels of LccA fractions stained for laccase activity and total protein. MonoQ 5/5 and Superdex 200 HR 10/30 fractions of LccA stained with SGZ (lanes 1 and 2); ABTS (lanes 3 and 4) and Coomassie brilliant blue R-250 (lanes 5 and 6), respectively. Protein standards (prestained BioRad) on left include: PHO b, phosphorylase b; BSA, bovine serum albumin, OVA, ovalbumin; CA, carbonic anhydrase, TRI, trypsin inhibitor; LYS, lysozyme.
Figure 3B:
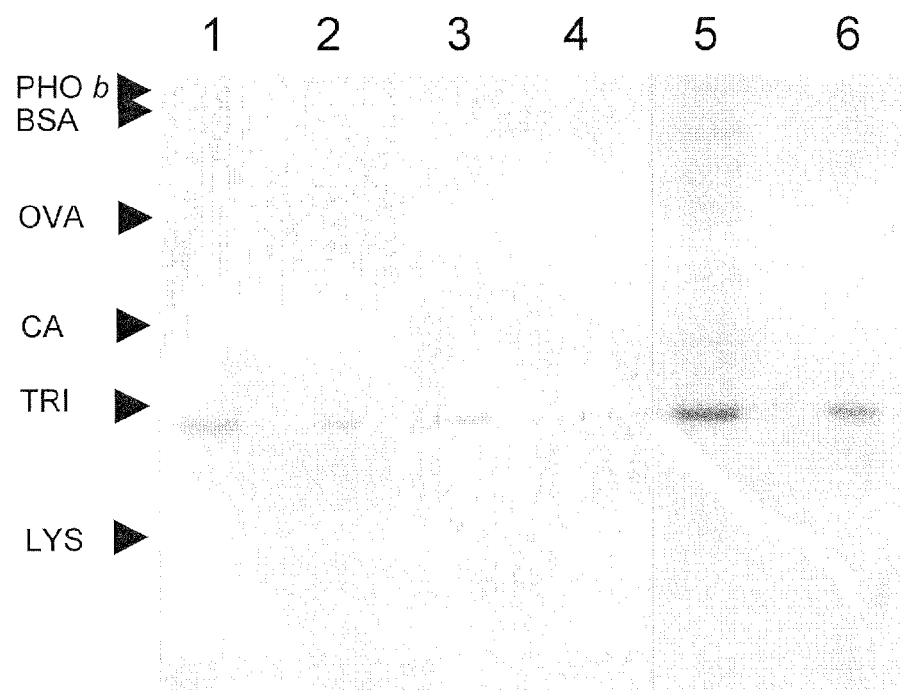
Figure 4:
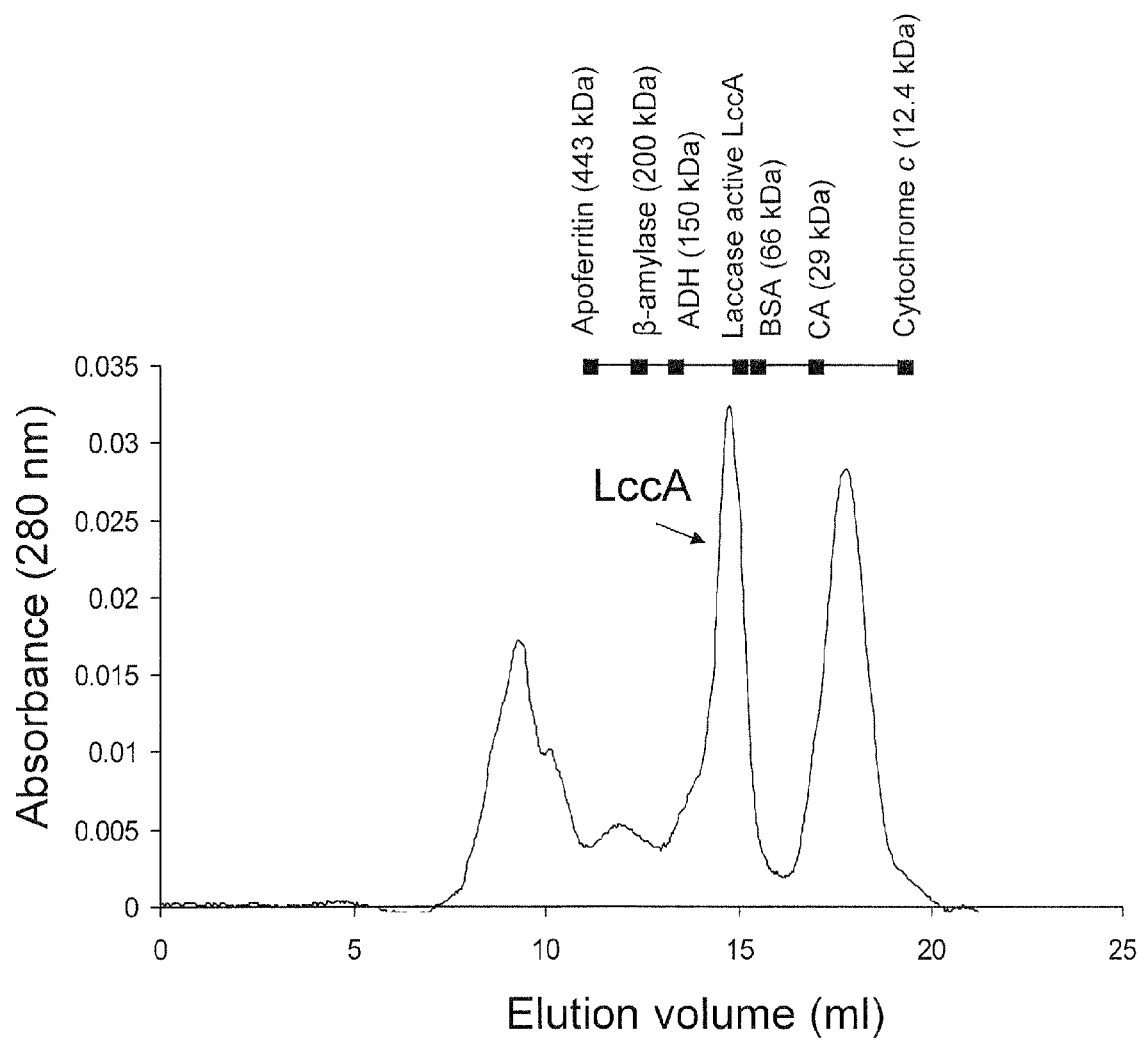
FIG. 4 shows LccA purified as an 65.4-kDa monomer from the culture broth of *Hfx. volcanii* SB01. Native molecular mass of LccA was determined by applying protein fractions eluted at 625 to 650 mM NaCl in 25 mM Tris-HCl buffer at pH 8.4 (T buffer) from MonoQ 5/5 to a Superdex 200 HR 10/30 column calibrated with protein molecular mass standards with elution volumes (■) as indicated.

Laccase activity was purified 12-fold from the culture broth of *Hfx. volcanii* SB01 to a specific activity of 1.3 U·mg$^{-1}$ (SGZ oxidation) as outlined in Table 2. For purification, extracellular proteins were precipitated from culture broth and fractionated by a combination of anion exchange and gel-filtration chromatography steps. It is interesting to note that the laccase activity reproducibly increased 1.4-fold after ethanol precipitation (Table 2), most likely due to the removal of inhibitory compounds and/or proteins from the sample by this technique. The final chromatography steps yielded a homogeneous and laccase-active preparation of LccA based on SDS-PAGE, mass spectroscopy and in gel activity staining (FIG. 3). Separation of protein fractions from the various stages of purification by SDS-PAGE revealed the final MonoQ 10/10 fraction was composed of a single protein band estimated at 70.7 kDa compared to the migration of molecular mass standards (FIG. 3A). This molecular mass was somewhat higher, yet consistent, with the 63,397 Da calculated in silico for the LccA polypeptide. Final MonoQ 10/10 fractions were further analyzed by mass spectrometry, using QSTAR XL hybrid LC/MS/MS, to confirm the protein composition and purity. The MS profiles of tryptic peptide fragments generated from the protein in solution were compared to the fragments generated after excision of the 71-kDa protein from the gel. In all cases, LccA was identified as the protein responsible for the laccase activity with 38 to 68% coverage (Table 5). LccA fractions were further analyzed by native PAGE coupled with in gel activity stain followed by staining for total protein. A single protein band was detected in the Superdex 200 HR 10/30 fractions that was active in the oxidation of both ABTS and SGZ (FIG. 3B). As the mobility in native PAGE gels depends on both the charge and hydrodynamic size of the protein, the low pI of LccA (calculated at 4.34) is likely to account for its rapid migration in the gel compared to proteins of lower molecular mass (e.g., 54-kDa ovalbumin). To estimate the native molecular mass of LccA, the protein was applied to a gel filtration chromatography (Superose 200 HR 10/30 column) calibrated with molecular mass standards. The LccA protein was estimated to be 65.4 kDa and, thus, is most likely associated as a monomer (FIG. 4). Unlike other characterized haloarchaeal proteins [e.g., (Wilson et al., 1999)], N-terminal sequencing of the LccA protein was unsuccessful suggesting it may be blocked by modifications such as $N^\alpha$-acetylation which is common to this organism (Kirkland et al., 2008).

Purification of LccA from Culture Broth of *Hfx. Volcanii* US02

Figure 9:
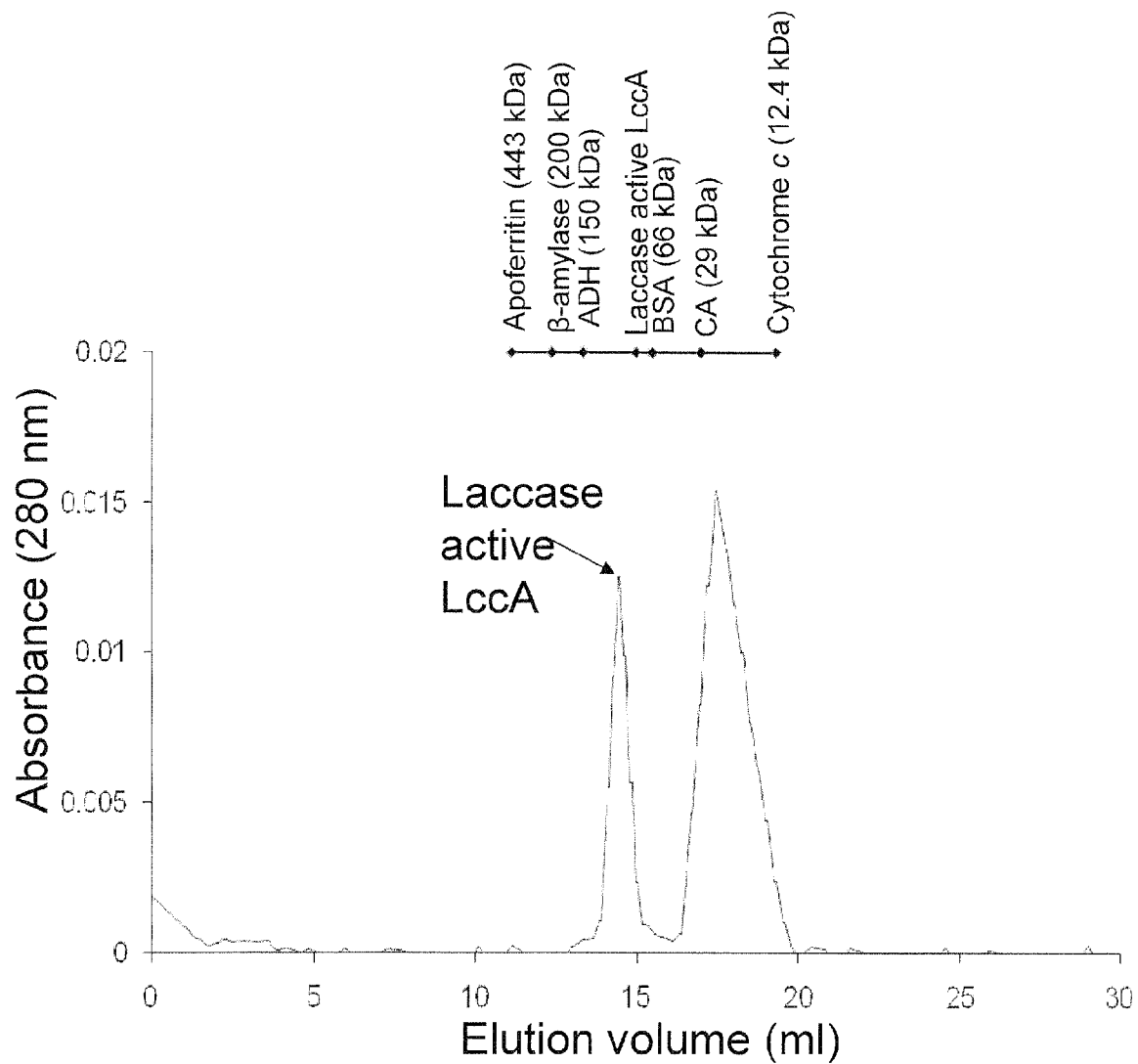
FIG. 9 shows Gel filtration analysis of LccA. LccA (MonoQ 5/5, pH 8.4, MQ1) fractions from *H. volcanii* SB01 were applied to a calibrated Superdex 200 HR 10/30 column as described in methods. The laccase active peak containing LccA protein is indicated by an arrow.

LccA was purified 13-fold from the culture broth of *H. volcanii* US02 to a specific activity of 29.4 U·mg$^{-1}$ by ethanol precipitation, concentration using a Centricon PL-30 centrifugal filter and fractionation by MonoQ chromatography as outlined in Table 2. LccA-StrepII was similarly purified from SB01 with the addition of gel filtration (FIG. 9) and MonoQ chromatography steps at the final stages of purification (Table 2). In contrast to US02 purified LccA, the specific activity of LccA-StrepII was over 20-fold lower at only 1.3 U·mg$^{-1}$. Thus, addition of a C-terminal StrepII tag not only reduced productivity of the strain but also reduced LccA enzyme activity. Incorporation of StrepTactin chromatography did not improve the overall activity or yield of LccA-StrepII from SB01 and, thus, was not further pursued (data not shown).

Figure 11:
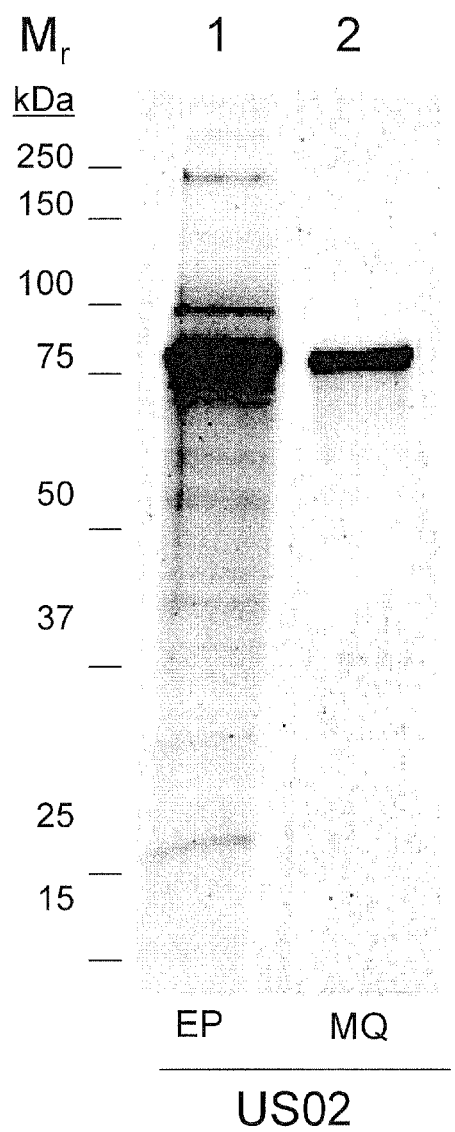
FIG. 11 shows LccA purified to electrophoretic homogeneity from the culture broth of *H. volcanii* US02. Reducing 10% SDS PAGE of LccA at various stages of purification including ethanol precipitate (lanes 1, EP) and MonoQ 10/10, pH 8.4 (lane 2, MQ) as indicated. Molecular standards left. Proteins were stained with Coomassie brilliant blue R-250.

The LccA protein isolated from US02 (as described above) was analyzed for purity by reducing SDS-PAGE and mass spectrometry (MS). Purified LccA migrated as a single protein band of 75-80 kDa (FIG. 11) that was specific for LccA based on MS analysis with 38 to 68% coverage of the LccA polypeptide sequence (FIGS. 7 and 10 and Table 5). The 10-20 kDa difference in migration of LccA by SDS-PAGE compared to that calculated from the polypeptide sequence was consistent with its low pI and/or post-translational modification by glycosylation.

Example 4

Multiple Isoforms of LccA

Figure 12A:
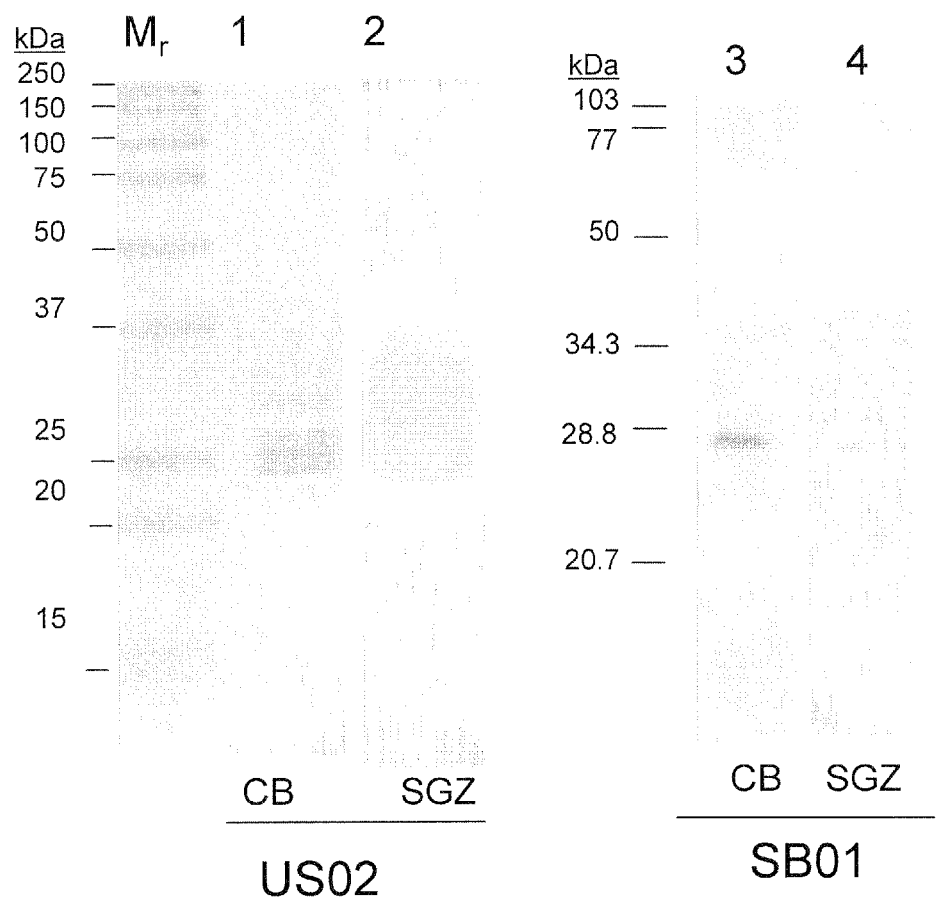
FIGS. 12A-12C show LccA purified from US02 is a glycoprotein. A, Native gels of LccA at its final stages of purification from US02 (Superdex 200 HR 10/30, lanes 1-2) and SB01 (MonoQ 10/10, pH 8.4, lanes 3-5). Gels were stained for total protein by Coomassie brilliant blue R-250 (CB) and laccase activity by in gel oxidation of SGZ (SGZ) as indicated. Prestained kaleidoscope and low range protein standards (Bio-Rad) were included for US02 and SB01, respectively as indicated on left of each gel. B, Pro-Q Emerald glycoprotein analysis of US02-purified LccA. Proteins were separated by reducing 10% SDS-PAGE. Gels were stained for glycosylation by Pro-Q Emerald (left) and total protein by SYPRO-Ruby (right) as indicated. Proteins included carbonic anhydrase (lane 1, CA), *T. versicolor* laccase (lane 2, TvLc), LccA MonoQ 10/10, pH 8.4, fractions (lane 3, HvLc$_{MQ}$), LccA ethanol precipitate (lane 4, HvLc$_{EP}$), CandyCane molecular mass standards (Molecular Probes) including a mixture of glyosylated (G) and nonglycosylated proteins as indicated (lane 5). C, Deglycosylation of LccA. LccA purified from US02 was treated with TFMS on ice for 0 h (lane 1), 10 h (lane 2) and 3 h (lane 3) and separated by reducing 6 and 10% SDS-PAGE as indicated (see methods for details).

LccA (purified as described above) was separated by native PAGE and stained for SGZ oxidizing activity and total protein. In contrast to SB01 purified LccA-StrepII, for which only a single protein band was detected, LccA purified from US02 migrated as at least four separate isoforms that were all active in SGZ oxidation (FIG. 12A). These results suggested that LccA was modified post-translational and that addition of a C-terminal StrepII tag abolished this modification. It should be noted that mobility in native gels depends not only on the hydrodynamic size but also the charge of the protein. The LccA polypeptide sequence is predicted to be highly acidic, and this is likely to account for the rapid migration of all of the LccA isoforms compared to protein standards of similar molecular mass.

Example 5

N-Terminal Cleavage and Glycosylation of LccA

Figure 12B:
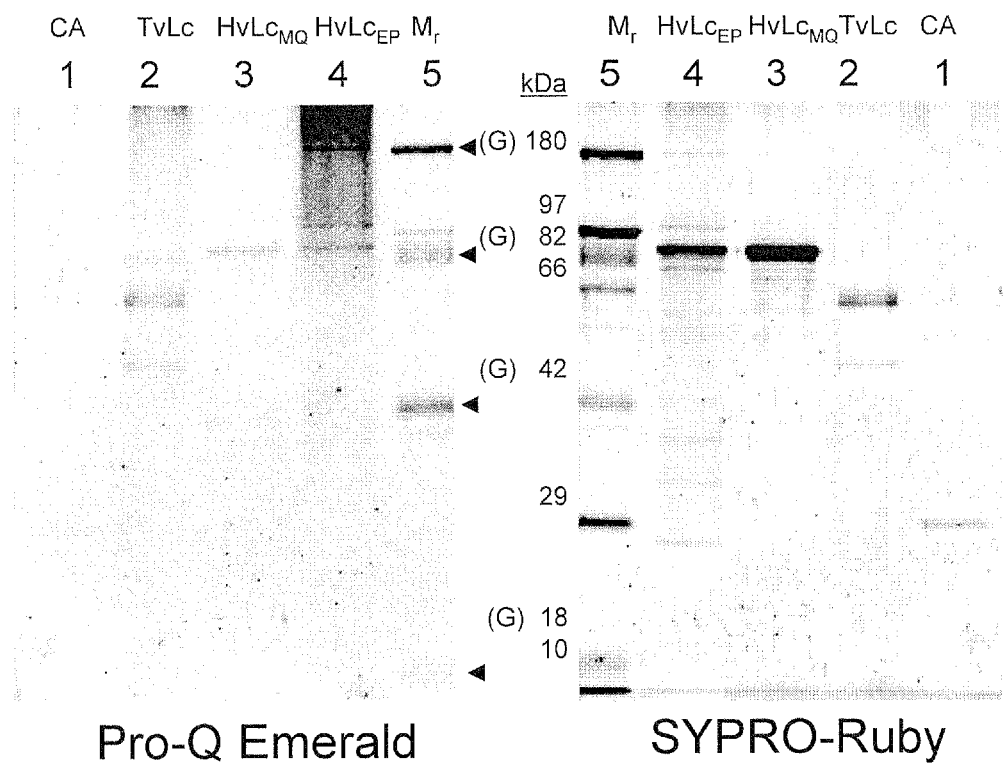
Figure 12C:
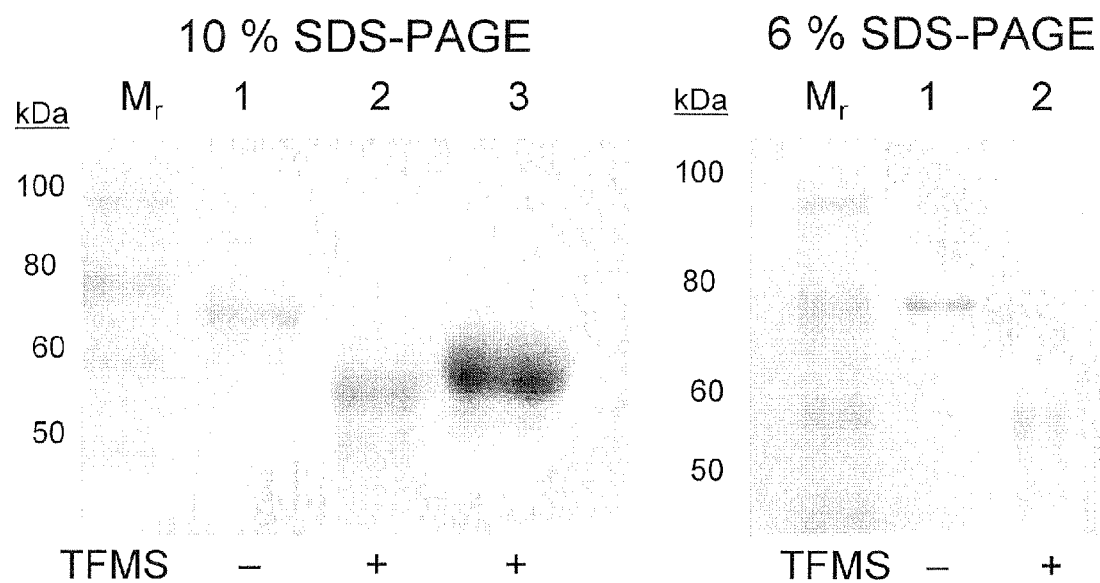
Figure 13:
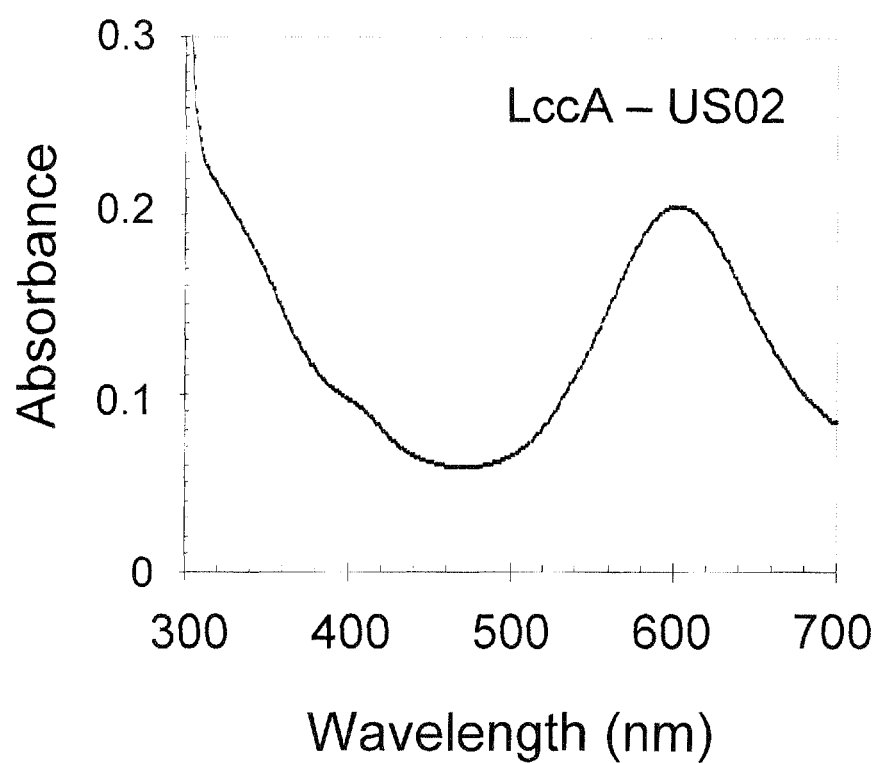
FIG. 13 shows UV-Visible absorbance spectrum of LccA. Absorbance of LccA (1.5 mg·ml$^{-1}$) purified from *H. volcanii* US02 in T buffer containing 185 mM NaCl was analyzed from 300 to 700 nm.

Many fungal laccases are modified post-translationally including removal of N-terminal residues as well as the addition of high-mannose-type glycans to Asn residues (N-glycosylation) [e.g., Bertrand et al., 2002; Giardina et al., 2007; Koikeda et al., 1993; Madzak et al., 2005; Quaratino et al., 2007; and Yaver et al., 1999]. Based on bioinformatics, LccA is predicted to be cleaved between Ala31 and Ala32 and to be N- and/or O-glycosylated (FIG. 7). To investigate these possibilities, the US02-purified LccA was N-terminal sequenced by Edman degradation and analyzed for glycosylation. Purified LccA was cleaved after Ala31 (FIG. 7) and glycosylated based on a carbohydrate content of 6.9±0.06% as determined by a phenol-sulfuric acid method (Dyall-Smith et al., 2008) and staining using Pro-Q Emerald 300 (Hoegger et al., 2006) (FIG. 12B). Although the carbohydrate content of LccA was 2.6-fold lower than observed for the commercial *T. versicolor* laccase, it was similar to the 6.9% previously reported for other fungal laccases (Barreca et al., 2003). To further analyze and confirm LccA glycosylation, the purified protein was treated with trifluoromethanesulfonic acid (TFMS), a strong acid known to remove glycans from polypeptide chains (Edman, P., 1970). A molecular weight shift of 10-20 kDa was observed by SDS-PAGE for the TFMS-treated LccA compared to the untreated control and resulted in its migration at ~60 kDa consistent with the molecular mass calculated from the deduced amino acid sequence (FIG. 12C). TFMS treatment did not shift the migration of non-glycosylated control proteins (e.g., carbonic anhydrase) confirming that polypeptide chains remained intact under these conditions (data not shown). Together these results provide evidence that LccA is secreted, cleaved and glycosylated during its maturation; however, the order of these events remains to be determined.

Interestingly, the LccA-StrepII variant purified from SB01 was not associated with carbohydrate and did not stain by Pro-Q Emerald (data not shown). Furthermore, the N-terminus of LccA-StrepII was not amendable to sequencing by Edman degradation suggesting it may be blocked by $N^\alpha$-acetylation. These results are consistent with the native PAGE analysis and suggest that addition of a StrepII tag to the C-terminus of LccA not only reduces its activity but also inhibits its N-terminal cleavage and glycosylation.

Example 6

Spectroscopic and Catalytic Properties of Purified LccA

Figure 5:
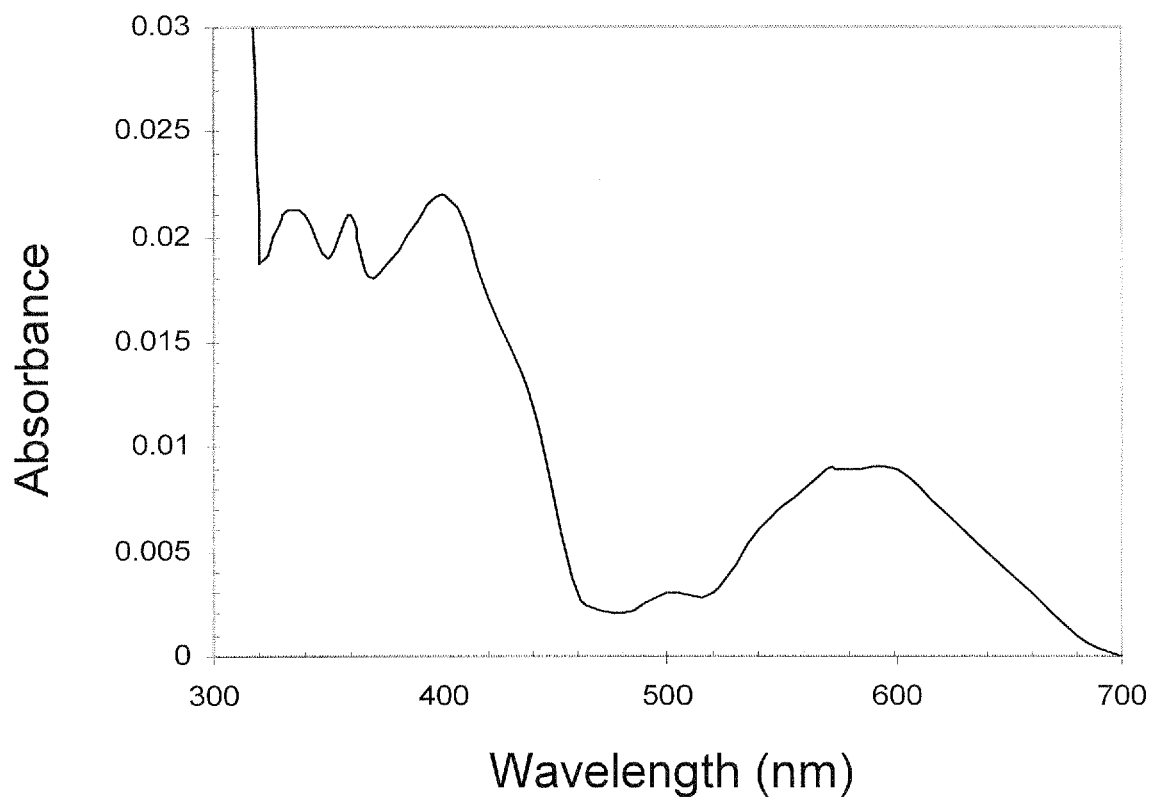
FIG. 5 show UV-Visible absorbance spectrum of LccA purified from HA volcanii SB01. Purified LccA (77 µg·ml$^{-1}$) was dissolved in T buffer containing 185 mM NaCl.

The purified LccA protein (purified from US02) was blue and exhibited an absorbance spectrum typical of blue multicopper oxidases including a peak at approximately 600 nm and shoulder at 330 nm (FIG. 5). Many laccases isolated from fungi and bacteria are blue multicopper oxidases that coordinate four copper atoms into three types of copper-binding sites (Hoegger et al., 2006). All of these 'blue' enzymes produce spectra with a maximum at 605 nm corresponding to the T1 or blue copper atom. The T2 copper site exhibits weakly visible absorbance, and the T3 copper site has two copper centers and is responsible for a shoulder at around 330 nm. The spectrum of LccA is consistent with its clustering to blue laccases including the closely related and structurally characterized *B. subtilis* CotA (Enguita et al., 2003). Thus, the conserved cysteine and 10 histidine residues are likely to coordinate the three types of copper sites in LccA.

The activity of LccA toward different phenolic and nonphenolic compounds was investigated. Four substrates most commonly used for determination of laccase activity were evaluated; 2,2'-azino-bis-3-ethylbenzthiazoline-6-sulphonic acid (ABTS), 2,6-dimethoxyphenol (DMP), 2-methoxyphenol (guaiacol), and 4-hydroxy-3,5-dimethoxybenzaldehyde azine (syringaldazine or SGZ). Oxidation of ferrous ($Fe^{2+}$) ammonium sulphate and bilirubin was also investigated. Although LccA did not oxidize $Fe^{2+}$ or guaiacol in the presence or absence of copper supplementation, it did oxidize the remaining substrates, i.e., ABTS at 6.1±0.39 $U \cdot mg^{-1}$, DMP at 12.6±1.1 $U \cdot mg^{-1}$, SGZ at 29.4±1.4 $U \cdot mg^{-1}$ and bilirubin at 25.5±1 $U \cdot mg^{-1}$ where the values reported are for US02-purified LccA under standard conditions (see methods for details). Note that the oxidation of DMP was highly stable for several hours but, unlike ABTS, SGZ and bilirubin, required addition of $CuSO_4$. LccA presented a higher specificity for SGZ than for ABTS, with $k_{cat}/K_m$ values of 0.62 and 0.015 $s^{-1} \mu M^{-1}$, respectively (Table 3). While the SGZ specificity of LccA was significantly lower than that of the DUF152 RL5-laccases, it is comparable to if not higher than that of *B. subtilis* CotA (Table 3). Furthermore, the specific activity of LccA for oxidation of bilirubin was comparable (if not higher, with a $k_{cat}/K_m$ value of 0.12 $s^{-1}$ ($k_{cat}$, 29 $s^{-1}$; $K_m$, 236 μM)) than reported for the Amano MvBO-3 enzyme at 1.2 $U mg^{-1}$ (Amano Enzyme USA, Product Data Sheet for Bilirubin Oxidase "Amano" 3 [BO-3] (*Myrothecium* sp.).

Recently, laccases have been grouped based on their DMP oxidase activity (Solano et al., 2001). The first group oxidizes DMP without copper supplementation (e.g., laccase of *Pyricularia oryzae*, PpoA of *Marinomonas mediterranea*), the second group of enzymes readily oxidize DMP after addition of copper but are also rapidly inactivated (e.g., CueO of *E. coli*) and the third type shows a very slow rate of DMP oxidation that lasts for hours, but only in the presence of added copper (e.g., CotA of *B. subtilis*). LccA oxidized DMP only in the presence of added $CuSO_4$; hence, it appears most similar to this latter group of laccases.

To further evaluate the catalytic properties of LccA, the temperature, pH and salt optima of the purified enzyme were determined using SGZ and/or ABTS as substrates. LccA activity was optimum at 45 to 50° C. (FIG. 6A), consistent with the optimal growth temperature of this organism (42 to 45° C.) (Robinson et al., 2005). Relative to this optimum, LccA was ~75% active at room temperature (25° C.) and 15, 35, 48 and 67% active at 70, 65, 60 and 55° C. respectively.

The temperature optimum of LccA is similar to a number of bacterial MCOs including the 40 to 45° C. for laccases of *Streptomyces* sp. (Niladevi and Prema, 2008; Endo et al., 2003), 52° C. for *Bacteroides thetaiotaomicron* BTH4389 and 44° C. for *Escherichia coli* YifH (Beloqui et al., 2006). It is also closely related to the temperature optimum for simultaneous saccharification and fermentation (SSF) processes which include fungal cellulases and second generation microbial biocatalysts (Endo et al., 2003). However, it is significantly lower than the 75° C. optimum for *Bacillus subtilis* CotA (Martins et al., 2002) and 70° C. optimum for *Aquifex aeolicus* McoA (Fernandes et al., 2007).

Most extracellular and intracellular enzymes of the haloarchaea, including *Hfx. volcanii*, require salt for activity and stability. Consistent with this, LccA activity was optimal at ~200 mM salt with 1.5-fold higher activity in KCl than NaCl, and the enzyme displayed reduced activity after removal of the salt by dialysis (FIG. 6B). LccA was also active at relatively high concentrations of salt with 65% relative activity at 1 M NaCl (FIG. 6B). The ability of LccA to rapidly oxidize phenolic substrates at molar concentrations of salt is not surprising as this enzyme is secreted by a microbe isolated from the Dead Sea. Similarly Lbh1 from *Bacillus halodurans* was stimulated by addition of 450 mM NaCl (Ruijssenaars and Hartmans, 2004).

While the oxidation of ABTS by LccA was optimal at low (pH of 6.0), its optimum for SGZ oxidization was more alkaline (pH of 8.4) (FIG. 6C). Most microbial laccases display optimal activity at low pH. Those with alkaline or near neutral pH optima are not as common with examples including those of *Acremonium murorum* (Gouka et al., 2001), *Bacillus halodurans* (Ruijssenaars and Hartmans, 2004), *Coprinus cinereus* (Yaver et al., 1999) and *Melanocarpus albomyces* (Kiiskinen et al., 2002). Unlike LccA, the few microbial laccases that are active at alkaline pH do not exhibit significant activity below pH 6.0. The alkalophilic nature of LccA might be of interest in paper pulp bleaching, which requires an alkaline pH optimum. These unique catalytic properties of LccA underline the potential of archaea as a source of high-value laccases.

Example 7

LccA is Stable at High Temperature, Salt and Solvent

To assess the thermostability of LccA, the purified protein was pre-incubated at various temperatures from 37 to 70° C. for up to 2½ days. LccA was fully active after 1 h at 55° C. and 5 h at 50° C., with a half-live of inactivation at 50° C. of 31.5 h (FIG. 6D). The enzyme retained nearly all of its original activity at 37° C. and 35 to 60% of its activity at 45 to 50° C., after incubation for 2½ days. These results reveal that LccA is highly thermostable, retaining most of its activity after prolonged incubation at moderately high temperatures. The multicopper oxidase of *Aquifex aeolicus*, McoA, has remarkably stable activity, with the ability to oxidize metals after incubation for 5 h at 90° C. (Fernandes et al., 2007). Likewise, the recently studied recombinant RL 5 laccase from rumen metagenome has maximal activity at 60° C. and is fully stable at this temperature for 200 min (Beloqui et al., 2006). CotA of *B. subtilis* is also thermostable, with a half-life of nearly 2 h at 80° C. (Martins et al., 2002). The purified LccA was also stable in a wide range of NaCl concentrations from 100 mM to, at least, 1.4 M, retaining nearly all of its original activity if not higher (FIG. 6E). It is noteworthy that prolonged incubation, from 90 min to 24 h, of LccA in salt did not alter this activity profile (data not shown). Recent analysis of a laccase from a bacterium isolated from a mangrove swamp (i.e., *Streptomyces psammoticus*) demonstrated this enzyme is also salt tolerant with full activity after incubation for 24 h in 0.8 M NaCl (Niladevi and Prema, 2008).

Commonly used water miscible organo-solvents (i.e., methanol, ethanol, dimethyl sulfoxide or DMSO and dimethylformamide or DMF) were examined for their compatibility with LccA stability and activity. Purified LccA protein was incubated in T buffer with 25% (v/v) solvent in the presence of salt (185 mM NaCl) for 90 min to 24 h. The enzyme and solvent mixtures were then diluted 4-fold and assayed for SGZ oxidizing activity under standard conditions (FIG. 6F). LccA was relatively stable in all solvents examined, retaining nearly 75% of its activity after 24 h incubation in methanol or ethanol and over 50% of its activity after incubation in DMSO or DMF. The influence of water-miscible cosolvents on enzyme activity and stability has been examined for several fungal laccases (Rodakiewicz-Nowak et al., 1999; Robles et al., 2002; Milstein et al., 1993; Luterek et al., 1998; Cantarella et al., 2003). These prior studies coupled with the current findings reveal a wide-variety of laccases, including LccA, are stable and/or can support catalysis and conversion of phenolic substrates in water-organic mixed solvents. Since most of the substrates and mediators of laccases are insoluble or poorly soluble in water and the degree of polymerization of phenoxyl radicals is higher in aqueous media (Milstein et al., 1993), solvent stability is an important feature to consider in optimizing this group of enzymes. Several industrial applications would greatly benefit from the addition of water-miscible organic cosolvents to laccase-mediated reactions, particularly the conversion of insoluble substrates such as lignin and its derivatives to useful products (Barreca et al., 2003; Potthast et al., 1995; d'Acunzo et al., 2004). Use of compatible organic solvents would also lower the degree of polymerization of phenoxyl radicals generated during the oxidation of substrates such as lignin (Milstein et al., 1993).

Example 8

Effect of Inhibitors

A number of compounds were examined for their influence on LccA activity including small ions (sodium azide or $NaN_3$), sulfhydryl-group containing redox reagents (L-cysteine, dithiothreitol or DTT), denaturants (thiourea) and chelators (EDTA, 1,10-phenanthroline, 2,2-dipyridyl) (Table 4). The most effective laccase inhibitors to date are small anions, especially $N_3^-$, which often bind to the trinuclear copper center and interfere with electron flow and substrate oxidation (Johnson et al., 2003). Consistent with this, LccA was inhibited nearly 50% by addition of 1 mM $NaN_3$. In contrast, some fungal laccases, such as that reported by Saito et al. (Saito et al., 2003), are relatively unaltered by $NaN_3$ (at 10 mM). Of the redox reagents examined, both L-cysteine and DTT were strong inhibitors of the observed LccA activity and were effective at relatively low concentrations (i.e., 0.1 to 1 mM). As has been observed for other laccases, this inhibition is likely caused by reduction of the oxidized substrate by the sulfhydryl-groups of the redox reagents and not by inhibition of the enzyme (Johannes et al., 2000). The LccA protein was also susceptible to denaturation by thiourea with 90% inhibition at 10 mM. Although the general chelator EDTA had no inhibitory activity toward LccA at 50 mM, the transition metal chelators 2,2-dipyridyl and 1,10-phenanthroline were inhibitory with a 25% and 90% reduction in LccA activity at 10 mM, respectively. These results are consistent with the recalcitrant nature of the copper-containing laccases toward chelation by EDTA (e.g., (Saito et al., 2003), yet reveal a likely role of metals in LccA activity, based on inhibition by phenanthroline.

Example 9

Improved Production of Laccase Activity by *Hfx. Volcanii*

Figure 14:
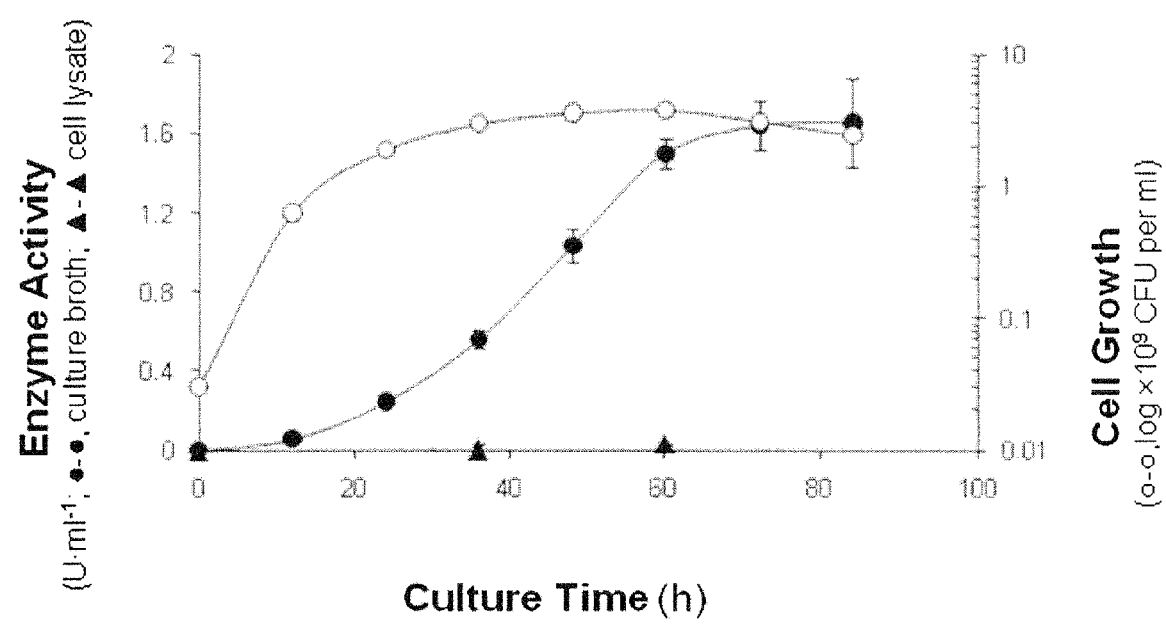
FIG. 14 shows laccase activity produced culture broth of *H. volcanii* strain US02 in accordance with the subject invention.

Laccase activity was produced at high-levels (1.65±0.22 $U \cdot ml^{-1}$) in the culture broth of *H. volcanii* strain US02 after 72 h of growth (at 42° C.; 150 rpm) in YPC medium supplemented with 100 µM $CuSO_4$ (see FIG. 14). Activity was enhanced 10-fold by improved culture and enzyme assay conditions compared to earlier report (Uthandi et al., 2010).

Example 10

Delignification of Sugarcane Bagasse by LccA

Prior to enzymatic treatment, sugarcane bagasse was treated with 1% (v/v) phosphoric acid and steam exploded in a shotgun reactor at 190° C. for 10 min. The resultant bagasse was adjusted to pH 8.4 with 5M NaOH.

Stream exploded bagasse was delignified using the laccase, LccA, from *H. volcanii* US02. LccA was prepared for the delignification reaction by concentrating *H. volcanii* US02 culture supernatant 5-fold with ethanol precipitation and dialyzing the concentrate against 25 mM Tris buffer pH 8.4 supplemented with 200 mM NaCl (T buffer) with regenerated cellulose dialysis tubing (3500 Da molecular weight cut off; Thermo Scientific SnakeSkin Pleated Dialysis Tubing).

Assays were performed with 3.7 g of steam exploded bagasse (~1 g dry weight equivalents) dissolved in 15 ml of T buffer in 250 ml Erlenmeyer flasks. Bagasse samples were treated with LccA in a rotary shaker at 150 rpm with similar doses of heat killed LccA enzyme (HKE) as a control. Periodically clear supernatant obtained by centrifugation of small fraction of hydrolysate was used for total phenol estimation by Folin-Ciocalteau method (Singleton and Rossi, 1965). Optimal conditions were determined to be treatment with 3 $Uml^1$ LccA at 37° C. in T buffer at pH 8.4 for 3-6 h.

Figure 15:
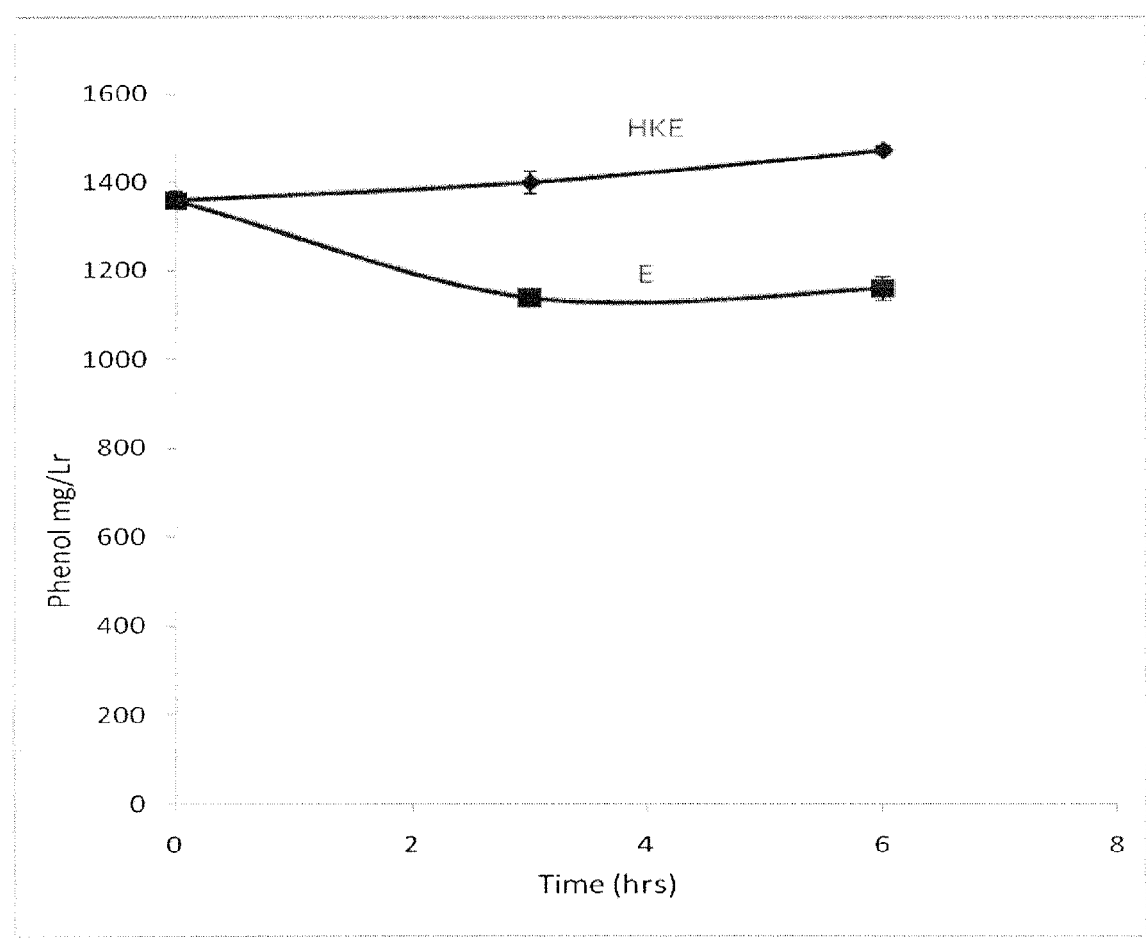
FIG. 15 shows ability of LccA to delignify sugarcane bagasse.

A 21% reduction in the phenol content from 1473±10 to 1160±26 mg phenol per liter after 3 h of treatment was reproducibly observed (see FIG. 15). Further dilution of steam exploded bagasse (~1 g dry weight equivalents) dissolved in 50 ml of T buffer resulted in a 38-43% reduction in the phenol content that was LccA-dependent.

Example 11

Improved Purification of Laccase (LccA) from *Hfx. Volcanii*

An improved protocol was developed for 22-fold purification of LccA from recombinant *H. volcanii* US02 to a specific activity of 51.5 $U \cdot mg^{-1}$. This protocol included ethanol precipitation of LccA from culture broth. The ethanol precipitates were then dialyzed (50 kDa MWCO) against 25 mM Tris buffer at pH 8.4 supplemented with 185 mM NaCl and concentrated to 15 mg protein per 11 ml with a Centricon PL-30 filter. LccA protein was further purified by MonoQ 10/10 anion exchange chromatography with T buffer and a linear gradient of NaCl. Results are shown in Table 6.

Example 12

Production and Activation of Laccase (LccA) from Recombinant E. coli

The *Hfx. volcanii* LccA gene was altered by site-directed mutagenesis for production of an LccA protein with an altered TAT signalling motif (Arg6Lys, Arg7Lys and Arg8Lys) (LccAΔTAT). This LccA protein variant was produced in recombinant *E. coli* Rosetta (DE3) (Table 1) using the pET expression system. Cells were lysed by French press (1,000 lb/in$^2$) in 20 mM Tris buffer at pH 7.5 with 150 mM NaCl. Cell lysate was clarified by centrifugation (10,000×g at 4° C. for 15 min) and NaCl was added to the supernatant to a final concentration of 2 M NaCl in 20 mM Tris buffer at pH 7.5. Laccase activity was assayed by the oxidation of SGZ using standard conditions. Specific activity of LccAΔTAT protein in cell lysate was 0.6 U·mg$^{-1}$ for a total of 1,100 U activity per liter of culture.

TABLE 1

List of strains, plasmids and oligonucleotide primers used in this study.

| Strain or plasmid | Description | Source or reference |
| --- | --- | --- |
| Strains | | |
| *E. coli* | | |
| DH5α | F$^-$ recA1 endA1 hsdR17($r_k^-$ $m_k^+$) supE44 thi-1 gyrA relA1 | Life Technologies |
| GM2163 | F$^-$ ara-14 leuB6 fhuA31 lacY1 tsx78 glnV44 galK2 galT22 mcrA dcm-6 hisG4 rfbD1 rpsL 136 dam13::Tn9 xylA5 mtl-1 thi-1 mcrB1 hsdR2 | New England Biolabs |
| Rosetta (DE3) | F$^-$ ompT hsdS$_B$($r_B^-$ $m_B^-$) gal dcm (DE3) pRARE (Cam$^R$) | Novagen |
| *Hfx. volcanii* DS70 | Wild-type isolate DS2 cured of plasmid pHV2 | (Wendoloski et al., 2001) |
| H26 | DS70 pyrE | (Allers et al., 2004) |
| SB01 | H26 carrying plasmid pJAM822 | This study |
| US02 | H26 carrying plasmid pJAM824 | This study |
| Plasmids | | |
| pET24b | Km$^r$; *E. coli* expression vector | Novagen |
| pBAP5010 | Ap$^r$; Nv$^r$; 11-kb *Hfx. volcanii*-*E. coli* shuttle vector derived from pBAP5009, includes *Halobacterium cutirubrum* rRNA P2 promoter (P2$_{rrn}$), T7 transcription terminator and pHV2 ori for expression of cloned genes in *Hfx. volcanii* | (Jolley et al., 1997) |
| pJAM202 | Ap$^r$; Nv$^r$; pBAP5010 containing P$_{rrn}$-psmB-H6 | (Kaczowka et al., 2003) |
| pJAM202c | Ap$^r$; Nv$^r$; pJAM202 with P$_{rrn}$-psmB-H6 deleted | (Zhou et al., 2008) |
| pJAM821 | Km$^r$; pET24b with lccA-strepII for expression of LccA (HvoB0205, laccase) with a C-terminal StrepII tag in *E. coli* Rosetta (DE3) | This study |
| pJAM822 | Ap$^r$; Nv$^r$; pJAM202 with P2$_{rrn}$-lccA-strepII for synthesis of LccA (HvoB0205, laccase) with a C-terminal StrepII tag in *Hfx. volcanii* | This study |
| pJAM823 | Km$^r$; pET24b with lccA for expression of LccA (HvoB0205, laccase) in *E. coli* Rosetta (DE3) | This study |
| pJAM824 | Ap$^r$; Nv$^r$; pJAM202 with P2$_{rrn}$-lccA for synthesis of LccA (HvoB0205, laccase) in *Hfx. volcanii* | This study |
| Primers | | |
| HvoB0205 (lccA) up | 5'-tgggcgtCATATGacagactggtctaggcggcgg-3' (SEQ ID NO: 7); NdeI site uppercase | This study |
| HvoB0205 (lccA) down | 5'-aaAAGCTTcacttctcgaactgcgggtgcgaccaAGTACTG gcgacttcgtcgccgcttc-3' (SEQ ID NO: 8); HindIII and ScaI site uppercase | This study |
| HvoB0205 (lccA) down 2 | 5'-aaAAGCTTtcaggccacttcgtcgccgcttc-3' (SEQ ID NO: 9); HindIII site uppercase | This study |

TABLE 2

Purification of LccA from the culture broth of Hfx. volcanii SB01 and US02 cells[a].

| Fraction | Total Activity (mU) | Protein (mg) | Yield (%) | Specific Activity (U · mg$^{-1}$) | Purification (-fold enrichment) |
|---|---|---|---|---|---|
| *Hfx. volcanii* SB01 | | | | | |
| 60-h culture broth (130 ml) | 740 | 6.72[a] | 100 | 0.11 | 1 |
| 60-h culture broth filtered | 765 | 6.43 | 103 | 0.12 | 1.1 |
| ethanol ppt. | 1010 | 6.33 | 136 | 0.16 | 1.5 |
| MonoQ 5/5, pH 8.4 | 467 | 0.92 | 63 | 0.51 | 4.6 |
| Superdex 200 HR 10/30 | 173 | 0.23 | 23 | 0.76 | 6.9 |
| MonoQ 10/10, pH 8.4 | 95.3 | 0.07 | 13 | 1.34 | 12 |
| *Hfx. volcanii* US02 | | | | | |
| 72-h culture broth (360 ml) | 57 | 25 | 100 | 1.4 | 1 |
| Ethanol precipitate | 55 | 13 | 94 | 4.3 | 2 |
| Centricon PL-30 and MonoQ 10/10, pH 8.4 | F1, 41.5; F2, 14.2 | F1, 1.4; F2, 2.1 | F1, 72; F2, 24 | F1 29.4; F2, 6.7 | F1, 13; F2, 2.9 |

[a]*Hfx. volcanii* SB01 and US02 were grown for 60 to 72 h in HvLMM (42° C., 200 rpm), respectively. LccA protein was purified from culture broth as indicated. Activity was monitored by oxidation of SGZ under standard assay conditions (see methods). F1 and F2 represents the lower (viscous) and upper fractions generated after concentration by centrifugal filtration using a Centricon PL-30, respectively (see methods).

TABLE 4

Effect of various compounds on activity of LccA isolated from *Hfx. volcanii* SB01.

| Compound[a] | Concentration (mM) | Relative Activity (%)[b] |
|---|---|---|
| Control | | 100.0 ± 0.9 |
| L-Cysteine | 0.1 | 83.0 ± 3.7 |
|  | 1 | u.d.[c] |
| Sodium azide | 1 | 55.2 ± 2.7 |
| DL-Dithiothretol | 0.01 | 90.5 ± 5.5 |
|  | 0.1 | u.d. |
|  | 1 | u.d. |
| EDTA | 0.1 | 100.6 ± 1.8 |
|  | 1 | 106.3 ± 5.8 |
|  | 5 | 123.6 ± 3.2 |
|  | 50 | 123.7 ± 3.0 |
| Thiourea | 1 | 96.5 ± 3.9 |
|  | 10 | 9.5 ± 1.3 |
| 1,10-Phenanthroline | 1 | 85.3 ± 3.4 |
|  | 10 | 10.9 ± 3.9 |
| 2,2-Dipyridyl | 1 | 86.6 ± 3.3 |
|  | 10 | 75.2 ± 2.3 |

[a]LccA was incubated with the various compounds for 10 min at 45° C. in T buffer with 185 mM NaCl and assayed for SGZ oxidizing activity under standard conditions.
[b]Values represent the average of at least 3 replicates.
[c]u.d., undetectable.

TABLE 3

Kinetic parameters of Hfx. volcanii LccA compared to select laccase-like enzymes.

| Enzyme, Origin of Encoding Gene | Source of Purified Enzyme | ABTS | | | SGZ | | | |
|---|---|---|---|---|---|---|---|---|
| | | $K_m$ (μM) | $k_{cat}$ (s$^{-1}$) | $k_{cat}/K_m$ (s$^{-1}$μM$^{-1}$) | $K_m$ (μM) | $k_{cat}$ (s$^{-1}$) | $k_{cat}/K_m$ (s$^{-1}$μM$^{-1}$) | Ref. |
| LccA, Hfx. volcanii | Culture broth of Hfx. volcanii BS01 | 700 | 10.0 | 0.014 | 67 | 19.4 | 0.3 | This study |
| | Culture broth of Hfx. volcanii US02 | 671 | 9.9 | 0.015 | 35 | 21.7 | 0.62 | This study |
| CotA, *Bacillus subtilis* | Cell lysate of recombinant *E. coli* | 106 | 16.8 | 0.16 | 26 | 3.7 | 0.14 | (Martins et al., 2002 |
| CotA, *Bacillus licheniformis* | Cell lysate of recombinant *E. coli* | 6.5 | 83 | 13 | 4.3 | 100 | 23 | (Koschorreck et al., 2008) |
| McoA, *Aquifex aeolicus* | Refolded from cell lysate of recombinant *E. coli* | 128 | 2.1 | 0.016 | 38 | 0.48 | 0.013 | (Fernandes et al., 2007) |
| LAC2, white-rot basidiomycete C30 | Culture supernatant of C30 | 536 | 683 | 1.27 | 6.8 | 1,093 | 160 | (Klonowska et al., 2002) |
| LAC1, white-rot basidiomycete C30 | Culture supernatant of C30 | 56 | 10.7 | 5.22 | 1.8 | 30 | 17 | (Klonowska et al., 2002) |
| RL5, metagenome library of bovine rumen (tentative *Bacteroides* origin) | Cell lysate of recombinant *E. coli* | 26 | 18 | 0.69 | 0.43 | 660 | 1,534 | (Beloqui et al., 2006) |
| BT4348, *Bacteroides thetaiotaomicron* | Cell lysate of recombinant *E. coli* | 10 | 217 | 21.7 | 0.83 | 555 | 669 | (Beloqui et al., 2006) |
| YifH, *E. coli* | Cell lysate of recombinant *E. coli* | 23 | 24 | 1.05 | 1.1 | 362 | 329 | (Beloqui et al., 2006) |

TABLE 5

Peptide summary report of Mascot search results generated from MS analysis of the tryptic peptides generated from LccA purified from *H. volcanii* SB01 and US02.

LccA from SB01:

| Residue no. Start-End | Observed | Mr(expt) | Mr(calc) | Delta | Miss | Peptide Sequence |
|---|---|---|---|---|---|---|
| 39-49 | 626.79 | 1251.57 | 1251.73 | -0.16 | 0 | K.FVQPLPIPSVR.E (Ions score 55) (SEQ ID NO: 10) |
| 39-55 | 645.63 | 1933.88 | 1934.04 | -0.16 | 1 | K.FVQPLPIPSVREPDGQR.D (Ions score 30) (SEQ ID NO: 11) |
| 105-121 | 648.91 | 1943.7 | 1943.9 | -0.2 | 0 | R.FDNSGLPSEHLFPVDDR.L (Ions score 74) (SEQ ID NO: 13) |
| 105-121 | 648.93 | 1943.77 | 1943.9 | -0.14 | 0 | R.FDNSGLPSEHLFPVDDR.L (Ions score 52) (SEQ ID NO: 13) |
| 122-141 | 689.26 | 2064.75 | 2064.99 | -0.23 | 0 | R.LGGTTAENHPGYDGPVPEVR.T (Ions score 85) (SEQ ID NO: 14) |
| 173-186 | 565.21 | 1692.61 | 1692.76 | -0.15 | 0 | R.FDSAWQELPMEQGR.T (Ions score 53) (SEQ ID NO: 16) |
| 187-200 | 801.81 | 1601.6 | 1601.78 | -0.18 | 0 | R.TTSTYHDHTLGITR.L (Ions score 103) (SEQ ID NO: 17) |
| 201-219 | 680.96 | 2039.87 | 2040.05 | -0.19 | 0 | R.LNAYAGLLGLYSITTDAER.E (Ions score 97) (SEQ ID NO: 18) |
| 220-237 | 662.63 | 1984.87 | 1985.04 | -0.17 | 0 | R.ELGLPSGDYDIPLLLQDK.E (Ions score 60) (SEQ ID NO: 19) |
| 407-415 | 518.15 | 1034.28 | 1034.51 | -0.23 | 0 | R.EMTLGTEVR.N (Ions score 44) (SEQ ID NO: 21) |
| 455-465 | 457.22 | 1368.63 | 1368.78 | -0.14 | 0 | R.HPIHLHLVTFR.V (Ions score 55) (SEQ ID NO: 23) |
| 466-485 | 681.96 | 2042.87 | 2043.04 | -0.17 | 1 | R.VIGRGPDGTQPPDPNELGPK.D (Ions score 68) (SEQ ID NO: 24) |
| 466-489 | 629.51 | 2513.99 | 2514.28 | -0.29 | 2 | R.VIGRGPDGTQPPDPNELGPKDTVR.V (Ions score 66) (SEQ ID NO: 25) |
| 470-485 | 809.76 | 1617.5 | 1617.76 | -0.26 | 0 | R.GPDGTQPPDPNELGPK.D (Ions score 77) (SEQ ID NO: 26) |
| 470-489 | 697.29 | 2088.84 | 2089.01 | -0.17 | 1 | R.GPDGTQPPDPNELGPKDTVR.V (Tons score 67) (SEQ ID NO: 27) |

LccA from US02:

| Start-End | Observed | Mr(expt) | Mr(calc) | Delta | Miss | Sequence |
|---|---|---|---|---|---|---|
| 39-49 | 626.94 | 1,252.03 | 1251.88 | 0.14 | 0 | K.FVQPLPIPSVR.E (Ion score 44) (SEQ ID NO: 10) |
| 39-55 | 968.06 | 1,934.20 | 1934.12 | 0.08 | 1 | K.FVQPLPIPSVREPDGQR.D (Ion score 18) (SEQ ID NO: 11) |
| 105-121 | 973.01 | 1,944.14 | 1944.01 | 0.11 | 0 | R.FDNSGLPSEHLFPVDDR.L (Ion score 70) (SEQ ID NO: 13) |
| 122-141 | 689.41 | 2,065.43 | 2065.21 | 0.22 | 0 | R.LGGTTAENHPGYDGPVPEVR.T (Ion score 45) (SEQ ID NO: 14) |
| 142-172 | 1103.22 | 3,306.77 | 3306.63 | 0.13 | 0 | R.TVTHFHGLELDPANDGQSDMWTSPGGVEGPR.F (Ion score 51) (SEQ ID NO: 15) |
| 173-186 | 565.37 | 1,693.44 | 1693.09 | 0.33 | 0 | R.FDSAWQELPMEQGR.T (Ion score 50 )(SEQ ID NO: 16) |
| 187-200 | 801.92 | 1,601.90 | 1601.83 | 0.06 | 0 | R.TTSTYHDHTLGITR.L (Ion score 98) (SEQ ID NO: 17) |
| 201-219 | 1021.07 | 2,040.20 | 2040.12 | 0.074 | 0 | R.LNAYAGLLGLYSITTDAER.E (Ion score 110) (SEQ ID NO: 18) |
| 220-237 | 993.58 | 1,985.28 | 1985.15 | 0.12 | 0 | R.ELGLPSGDYDIPLLLQDK.E (Ion score 68) (SEQ ID NO: 19) |
| 238-275 | 1419.11 | 4,254.65 | 4254.31 | 0.32 | 0 | K.EFNDDGSLHYPEEFVSAFLGDTAVVNGAVWRYVEVEPR.R (Ion score 28) (SEQ ID NO: 12) |
| 279-288 | 599.38 | 1,196.84 | 1196.74 | 0.09 | 1 | R.FRILNGANHR.S (Ion score 33) (SEQ ID NO: 20) |
| 372-406 | 1211.65 | 3,633.18 | 3631.93 | 1.25 | 1 | R.VSDPSTPPEDASADPTSLSLPTPASYDESDARVTR.E (SEQ ID NO: 22) |

TABLE 5-continued

Peptide summary report of Mascot search results generated from MS analysis of the tryptic peptides generated from LccA purified from H. volcanii SB01 and US02.

| 407-415 | 518.34 | 1,034.85 | 1034.68 | 0.17 | 0 | R.EMTLGTEVR.N (Ion score 48) (SEQ ID NO: 21) |
| 466-489 | 1022.59 | 2,043.31 | 2043.17 | 0.13 | 2 | R.VIGRGPDGTQPPDPNELGPK.D (Ion score 47) (SEQ ID NO: 24) |
| 466-485 | 839.16 | 2,514.63 | 2514.45 | 0.17 | 1 | R.VIGRGPDGTQPPDPNELGPKDTVR.V (SEQ ID NO: 25) |
| 470-489 | 697.40 | 2,089.37 | 2089.19 | 0.18 | I | R.GPDGTQPPDPNELGPKDTVR.V (Ion score 31) (SEQ ID NO: 27) |
| 470-485 | 37.25 | 1,617.92 | 1617.84 | 0.07 | 0 | R.GPDGTQPPDPNELGPK.D (Ion score 37) (SEQ ID NO: 26) |

TABLE 6

Improved purification of laccase (LccA) from H. volcanii

| Fraction | Total Activity (U) | Protein (mg) | Yield (%) | Specific Activity (U·mg$^{-1}$) | Purification (-fold enrichment) |
|---|---|---|---|---|---|
| 72 h-culture broth (295 ml) | 439.5 | 189.8 | 100 | 2.3 | 1.0 |
| Concentration by ethanol ppt, dialysis & Centricon | 249.2 | 15.3 | 56.7 | 16.2 | 7.0 |
| MonoQ 10/10, pH 8.4 | 123.8 | 2.4 | 28.1 | 51.5 | 22.2 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Solomon, E. I., Sundaram, U. M., and Machonkin, T. E. (1996) Chem. Rev. 96, 2563-2606.
Hoegger, P. J., Kilaru, S., James, T. Y., Thacker, J. R., and Kues, U. (2006) FEBS J. 273, 2308-2326.
Hüttermann, A., Mai, C., and Kharazipour, A. (2001) Appl. Microbiol. Biotechnol. 55, 387-394.
Sakurai, T. and Kataoka, K. (2007) Chem. Rec. 7, 220-229.
Shleev, S., Tkac, J., Christenson, A., Ruzgas, T., Yaropolov, A. I., Whittaker, J. W., and Gorton, L. (2005) Biosens. Bioelectron. 20, 2517-2554.
Claus, H. (2004) Micron. 35, 93-96.
Ranocha, P., Chabannes, M., Chamayou, S., Danoun, S., Jauneau, A., Boudet, A. M., and Goffner, D. (2002) Plant Physiol. 129, 145-155.
Widsten, P. and Kandelbauer, A. (2008) Biotechnol. Adv. 26, 379-386.
Claus, H. and Filip, Z. (1998) Acta Hydrochim Hydrobiol 26, 180-185.
Claus, H. (2003) Arch. Microbiol. 179, 145-150.
Fitz-Gibbon, S. T., Ladner, H., Kim, U. J., Stetter, K. O., Simon, M. I., and Miller, J. H. (2002) Proc. Natl. Acad. Sci. U.S.A. 99, 984-989.
Copeland, A., Lucas, S., Lapidus, A., Barry, K., Glavina del Rio, T., Dalin, E., Tice, H., Bruce, D., Pitluck, S., and Richardson, P. (2008) GenBank 153896174.
Hartman, A. L., Norais, C., Badger, J., Madupu, R., Robinson, J., Khouri, H., Ren, Q., Lowe, T., Maupin-Furlow, J., Pohlschröder, M., Allers, T., Daniels, C., and Eisen, J. A. (2009) PLoS One, 5, 1-20.
Dyall-Smith, M. (2008) The Halohandbook: Protocols for Halobacterial Genetics.
Altschul, S. F., Madden, T. L., Schaffer, A. A., Zhang, J., Zhang, Z., Miller, W., and Lipman, D. J. (1997) Nucleic Acids Res. 25, 3389-3402.
Hall, T. A. (1999) Nucl. Acids. Symp. Ser. 41, 95-98.
Mander, G. J., Wang, H., Bodie, E., Wagner, J., Vienken, K., Vinuesa, C., Foster, C., Leeder, A. C., Allen, G., Hamill, V., Janssen, G. G., Dunn-Coleman, N., Karos, M., Lemaire, H. G., Subkowski, T., Bollschweiler, C., Turner, G., Nusslein, B., and Fischer, R. (2006) Appl. Environ. Microbiol. 72, 5020-5026.
Martins, L. O., Soares, C. M., Pereira, M. M., Teixeira, M., Costa, T., Jones, G. H., and Henriques, A. O. (2002) J. Biol. Chem. 277, 18849-18859.
Suzuki, T., Endo, K., Ito, M., Tsujibo, H., Miyamoto, K., and Inamori, Y. (2003) Biosci. Biotechnol. Biochem. 67, 2167-2175.
Kumar, S., Tamura, K., and Nei, M. (2004) Brief Bioinform. 5, 150-163.
Thompson, J. D., Higgins, D. G., and Gibson, T. J. (1994) Nucleic Acids Res. 22, 4673-4680.
Bendtsen, J. D., H. Nielsen, D. Widdick, T. Palmer, and S. Brunak. (2005) BMC Bioinformatics. 6, 167.
Rose, R. W., Bruser, T., Kissinger, J. C., and Pohlschroder, M. (2002) Mol. Microbiol. 45, 943-950.
Caragea, C., Sinapov, J., Silvescu, A., Dobbs, D., and Honavar, V. (2007) BMC Bioinformatics. 8, 438.
Wendoloski, D., C. Ferrer, and M. L. Dyall-Smith (2001) Microbiology. 147, 959-964.
Bradford, M. M. (1976) Anal. Biochem. 72, 248-254.
Edman, P. (1970) Mol. Biol. Biochem. Biophys. 8, 211-255.
Dubois, M., K. A. Gilles, J. K. Hamilton, P. A. Rebers, and F. Smith. (1956) Anal. Chem. 28, 350-356.
Edge, A. S., C. R. Faltynek, L. H of, L. E. Reichert, Jr., and P. Weber. (1981) Anal. Biochem. 118, 131-137.
Norais, C., M. Hawkins, A. L. Hartman, J. A. Eisen, H. Myllykalio, and T. Allers. (2007) Plos Genet., 3, e77.
Ng, W. V., Kennedy, S. P., Mahairas, G. G., Berquist, B., Pan, M., Shukla, H. D., Lasky, S. R., Baliga, N. S., Thorsson, V., Sbrogna, J., Swartzell, S., Weir, D., Hall, J., Dahl, T. A., Welti, R., Goo, Y. A., Leithauser, B., Keller, K., Cruz, R., Danson, M. J., Hough, D. W., Maddocks, D. G., Jablonski, P. E., Krebs, M. P., Angevine, C. M., and Dale, H. (2000) *Proc. Natl. Acad. Sci. U.S.A.* 97, 12176-12181.

Bolhuis, H. H., Palm, P. P., Wende, A. A., Falb, M. M., Rampp, M. M., Rodriguez-Valera, F. F., Pfeiffer, F. F., and Oesterhelt, D. D. (2006) *BMC Genomics.* 7, 169.

Baliga, N. S., Bonneau, R., Facciotti, M. T., Pan, M., Glusman, G., Deutsch, E. W., Shannon, P., Chiu, Y., Weng, R. S., Gan, R. R., Hung, P., Date, S. V., Marcotte, E., Hood, L., and Ng, W. V. (2004) *Genome Res.* 14, 2221-2234.

Falb, M., Pfeiffer, F., Palm, P., Rodewald, K., Hickman, V., Tittor, J., and Oesterhelt, D. (2005) *Genome Res.* 15, 1336-1343.

Koschorreck, K., Richter, S. M., Ene, A. B., Roduner, E., Schmid, R. D., and Urlacher, V. B. (2008) *Appl. Microbiol. Biotechnol.* 79, 217-224.

Cozen, A. E., M. T. Weirauch, K. S. Pollard, D. L. Bernick, J. M. Stuart, and T. M. Lowe. (2009) *J. Bacteriol.* 191, 782-794.

Singh, S. K., Grass, G., Rensing, C., and Montfort, W. R. (2004) *J. Bacteriol.* 186, 7815-7817.

Fernandes, A. T., Soares, C. M., Pereira, M. M., Huber, R., Grass, G., and Martins, L. O. (2007) *FEBS J.* 274, 2683-2694

Sitthisak, S., Howieson, K., Amezola, C., and Jayaswal, R. K. (2005) *Appl. Environ. Microbiol.* 71, 5650-5653.

Solano, F., Lucas-Elio, P., Lopez-Serrano, D., Fernandez, E., and Sanchez-Amat, A. (2001) *FEMS Microbiol. Lett.* 204, 175-181.

Roberts, S. A., A. Weichsel, G. Grass, K. Thakali, J. T. Hazzard, G. Tollin, C. Rensing, and W. R. Montfort. (2002) *Proc. Natl. Acad. Sci. U.S.A.* 99, 2766-2771.

Kaczowka, S. J., and J. A. Maupin-Furlow. (2003) *J. Bacteriol.* 185, 165-174.

Reuter, C. J., S. J. Kaczowka, and J. A. Maupin-Furlow. (2004) *J. Bateriol.* 186, 7763-7772.

Connaris, H., Chaudhuri, J. B., Danson, M. J., and Hough, D. W. (1999) *Biotechnol. Bioeng.* 64, 38-45.

Madzak, C., Otterbein, L., Chamkha, M., Moukha, S., Asther, M., Gaillardin, C., and Beckerich, J. M. (2005) *FEMS Yeast Res.* 5, 635-646.

Brüser, T. (2007) *Appl. Microbiol. Biotechnol.* 76, 35-45.

Koikeda, S., Ando, K., Kaji, H., Inoue, T., Murao, S., Takeuchi, K., and Samejima, T. (1993) *J. Biol. Chem.* 268, 18801-18809.

Jolivalt, C., Madzak, C., Brault, A., Caminade, E., Malosse, C., and Mougin, C. (2005) *Appl. Microbiol. Biotechnol.* 66, 450-456.

Guo, M., Lu, F., Du, L., Pu, J., and Bai, D. (2006) *Appl. Microbiol. Biotechnol.* 71, 848-852.

Kataoka, K., Tanaka, K., Sakai, Y., and Sakurai, T. (2005) *Protein Expr. Purif.* 41, 77-83.

Miyazaki, K. (2005) *Extremophiles.* 9, 415-425.

Ruijssenaars, H. J. and Hartmans, S. (2004) *Appl. Microbiol. Biotechnol.* 65, 177-182.

Beloqui, A., Pita, M., Polaina, J., Martinez-Arias, A., Golyshina, O. V., Zumarraga, M., Yakimov, M. M., Garcia-Arellano, H., Alcalde, M., Fernandez, V. M., Elborough, K., Andreu, J. M., Ballesteros, A., Plou, F. J., Timmis, K. N., Ferrer, M., and Golyshin, P. N. (2006) *J. Biol. Chem.* 281, 22933-22942.

Wilson, H. L., Aldrich, H. C., and Maupin-Furlow, J. A. (1999) *J. Bacteriol.* 181, 5814-5824.

Kirkland, P. A., Humbard, M. A., Daniels, C. J., and Maupin-Furlow, J. A. (2008) *J. Proteome Res.* 7, 5033-5039.

Enguita, F. J., Martins, L. O., Henriques, A. O., and Carrondo, M. A. (2003) *J. Biol. Chem.* 278, 19416-19425.

Robinson, J. L., Pyzyna, B., Atrasz, R. G., Henderson, C. A., Morrill, K. L., Burd, A. M., Desoucy, E., Fogleman, R. E., III, Naylor, J. B., Steele, S. M., Elliott, D. R., Leyva, K. J., and Shand, R. F. (2005) *J. Bacteriol.* 187, 923-929.

Niladevi, K. N. and Prema, P. (2008) *Bioresour. Technol.* 99, 4583-4589.

Endo, K., Hayashi, Y., Hibi, T., Hosono, K., Beppu, T., and Ueda, K. (2003) *J. Biochem.* 133, 671-677.

Patel, M. A., Ou, M. S., Harbrucker, R., Aldrich, H. C., Buszko, M. L., Ingram, L. O., and Shanmugam, K. T. (2006) *Appl. Environ. Microbiol.* 72, 3228-3235.

Gouka, R. J., van der, H. M., Swarthoff, T., and Verrips, C. T. (2001) *Appl. Environ. Microbiol.* 67, 2610-2616.

Yaver, D. S., Overjero, M. D., Xu, F., Nelson, B. A., Brown, K. M., Halkier, T., Bernauer, S., Brown, S. H., and Kauppinen, S. (1999) *Appl. Environ. Microbiol.* 65, 4943-4948.

Kiiskinen, L. L., Viikari, L., and Kruus, K. (2002) *Appl. Microbiol. Biotechnol.* 59, 198-204.

Rodakiewicz-Nowak, J., Haber, J., Pozdnyakova, N., Leontievsky, A., and Golovleva, L. A. (1999) *Biosci. Rep.* 19, 589-600.

Robles, A., Lucas, R., Martinez-Caòamero, M., Ben Omar, N., Pérez, R., and Gàlvez, A. (2002) *Enzyme Microb. Technol.* 31, 516-522.

Milstein, O., Hüttermann, A., Majcherczyk, A., Schulze, K., Fründ, R., and Lüdemann, H. D. (1993) *J. Biotechnol.* 30, 37-47.

Luterek, J., Gianfreda, L., Wotjas-Wasilewska, M., Cho, N. S., Rogalski, J., Jaszek, M., Malarczyke, E., Staxzczak, M., Fink-Boots, M., and Leonowicz, A. (1998) *Holzforschung* 52, 589-595.

Cantarella, G., d'Acunzo, F., and Galli, C. (2003) *Biotechnol. Bioeng.* 82, 395-398.

Barreca, A. M., Fabbrini, M., Galli, C., Gentili, P., and Ljunggren, S. (2003) *J. Mol. Catal. B: Enzym.* 26, 105-110.

Potthast, A., Rosenau, T., Chen, C. L., and Gratzl, J. S. (1995) *J. Org. Chem.* 60, 4320-4321.

d'Acunzo, F., Barreca, A. M., and Galli, C. (2004) *J. Mol. Catal. B: Enzym.* 31, 25-30.

Johnson, D. L., Thompson, J. L., Brinkmann, S. M., Schuller, K. A., and Martin, L. L. (2003) *Biochemistry.* 42, 10229-10237.

Saito, T., Hong, P., Kato, K., Okazaki, M., Inagaki, H., Maeda, S., and Yokogawa, Y. (2003) *Enzyme Microb. Technol.* 33, 520-526.

Johannes, C. and Majcherczyk, A. (2000) *J. Biotechnol.* 78, 193-199.

Wendoloski, D., Ferrer, C., and Dyall-Smith, M. L. (2001) *Microbiology* 147, 959-964.

Allers, T., Ngo, H. P., Mevarech, M., and Lloyd, R. G. (2004) *Appl. Environ. Microbiol.* 70, 943-953.

Jolley, K. A., Russell, R. J., Hough, D. W., and Danson, M. J. (1997) *Eur. J. Biochem.* 248, 362-368.

Kaczowka, S. J. and Maupin-Furlow, J. A. (2003) *J. Bacteriol.* 185, 165-174.

Zhou, G. Y., Kowalczyk, D., Humbard, M. A., Rohatgi, S., and Maupin-Furlow, J. A. (2008) *J. Bacteriol.* 190, 8096-8105.

Klonowska, A., Gaudin, C., Fournel, A., Asso, M., Le Petit, J., Giorgi, M., and Tron, T. (2002) *Eur. J. Biochem.* 269, 6119-6125.

Svistoonoff, S., Creff, A., Reymond, M., Sigoillot-Claude, C., Ricaud, L., Blanchet, A., Nussaume, L., and Desnos, T. (2007) *Nat. Genet.* 39, 792-796.

Wang, G., Kennedy, S. P., Fasiludeen, S., Rensing, C., and DasSarma, S. (2004) *J. Bacteriol.* 186, 3187-3194.

Joo, S. S., Ryu, I. W., Park, J. K., Yoo, Y. M., Lee, D. H., Hwang, K. W., Choi, H. T., Lim, C. J., Lee, d., I, and Kim, K. (2008) *Mol. Cells.* 25, 112-118.

Sakamoto, Y., Nakade, K., Yano, A., Nakagawa, Y., Hirano, T., Irie, T., Watanabe, H., Nagai, M., and Sato, T. (2008) *Appl. Microbiol. Biotechnol.* 79, 971-980.

Sanchez-Amat, A., Lucas-Elio, P., Fernandez, E., Garcia-Borron, J. C., and Solano, F. (2001) *Biochim. Biophys. Acta.* 1547, 104-116.

Choy, H. A. and Jones, G. H. (1981) *Arch. Biochem. Biophys.* 211, 55-65.

Machczynski, M. C., Vijgenboom, E., Samyn, B., and Canters, G. W. (2004) *Protein Sci.* 13, 2388-2397.

We claim:

1. A purified polypeptide comprising:
   a) the amino acid sequence of SEQ ID NO: 2;
   b) a polypeptide having laccase activity and comprising an amino acid sequence that has greater than 90% amino acid sequence identity to the amino acid sequence of SEQ ID NO: 2;
   c) a fragment of the polypeptide set forth in a) or b), said fragment having laccase activity or a fragment of the amino acid sequence of SEQ ID NO:2, the N-terminal residue of the fragment being any one of the residues 140-145 of SEQ ID NO: 2 and the C-terminal residue of the fragment being any one of the residues 524-579 of SEQ ID NO: 2, said fragment having laccase activity; or
   d) a polypeptide having laccase activity and comprising the amino acid sequence of amino acids 32-579 of SEQ ID NO: 2.

2. A composition comprising the purified polypeptide of claim 1 and a carrier.

3. A method of oxidizing a phenolic substrate comprising contacting the purified polypeptide according to claim 1 with a phenolic substrate under conditions that allow for the oxidation of the phenolic substrate.

4. A method of oxidizing bilirubin to biliverdin and water comprising contacting the purified polypeptide according to claim 1 with a solution comprising bilirubin under conditions that allow for oxidizing bilirubin to biliverdin and water.

5. A method for delignification and/or detoxification of acid-pretreated biomass comprising contacting acid-pretreated biomass with-a the purified polypeptide according to claim 1 under conditions that allow for the delignification and/or detoxification of acid-pretreated biomass.

6. A method of bleaching dye comprising contacting a solution comprising a dye with the purified polypeptide according to claim 1 under conditions that allow for the bleaching of said dye.

7. A method of bleaching pulp for paper production comprising contacting pulp for paper production with the purified polypeptide according to claim 1 under conditions that allow for the bleaching of said pulp.

8. A method of modifying lignin comprising contacting lignin with the purified polypeptide according to claim 1 under conditions that allow for the modification of said lignin.

9. A method for the treatment of waste water comprising contacting waste water containing a phenolic compound with the purified polypeptide according to claim 1 under conditions that allow for the oxidation of said phenolic compound.

10. The purified polypeptide according to claim 1, wherein said polypeptide comprises the amino acid sequence of SEQ ID NO: 2.

11. The purified polypeptide according to claim 1, wherein said polypeptide has laccase activity and comprises the amino acid sequence of amino acids 32-579 of SEQ ID NO: 2.

12. The purified polypeptide according to claim 1, wherein said polypeptide has laccase activity and comprises an amino acid sequence that has greater than 90% amino acid sequence identity to the amino acid sequence of SEQ ID NO: 2.

13. The purified polypeptide according to claim 1, wherein said polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

14. The purified polypeptide according to claim 12, wherein said polypeptide has laccase activity and comprises an amino acid sequence that has greater than 95% amino acid sequence identity to the amino acid sequence of SEQ ID NO: 2.

15. The method according to claim 3, wherein said purified polypeptide comprises the amino acid sequence of SEQ ID NO: 2.

16. The method according to claim 3, wherein said purified polypeptide has laccase activity and comprises the amino acid sequence of amino acids 32-579 of SEQ ID NO: 2.

17. The method according to claim 3, wherein said purified polypeptide has laccase activity and comprises an amino acid sequence that has greater than 90% amino acid sequence identity to the amino acid sequence of SEQ ID NO: 2.

18. The method according to claim 17, wherein said purified polypeptide has laccase activity and comprises an amino acid sequence that has greater than 95% amino acid sequence identity to the amino acid sequence of SEQ ID NO: 2.

19. The method according to claim 3, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

20. The method according to claim 4, wherein said purified polypeptide comprises the amino acid sequence of SEQ ID NO: 2.

21. The method according to claim 4, wherein said purified polypeptide has laccase activity and comprises the amino acid sequence of amino acids 32-579 of SEQ ID NO: 2.

22. The method according to claim 4, wherein said purified polypeptide has laccase activity and comprises an amino acid sequence that has greater than 90% amino acid sequence identity to the amino acid sequence of SEQ ID NO: 2.

23. The method according to claim 22, wherein said purified polypeptide has laccase activity and comprises an amino acid sequence that has greater than 95% amino acid sequence identity to the amino acid sequence of SEQ ID NO: 2.

24. The method according to claim 4, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

25. The method according to claim 5, wherein said purified polypeptide comprises the amino acid sequence of SEQ ID NO: 2.

26. The method according to claim 5, wherein said purified polypeptide has laccase activity and comprises the amino acid sequence of amino acids 32-579 of SEQ ID NO: 2.

27. The method according to claim 5, wherein said purified polypeptide has laccase activity and comprises an amino acid sequence that has greater than 90% amino acid sequence identity to the amino acid sequence of SEQ ID NO: 2.

28. The method according to claim 27, wherein said purified polypeptide has laccase activity and comprises an amino acid sequence that has greater than 95% amino acid sequence identity to the amino acid sequence of SEQ ID NO: 2.

29. The method according to claim 5, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

30. The method according to claim 6, wherein said purified polypeptide comprises the amino acid sequence of SEQ ID NO: 2.

31. The method according to claim 6, wherein said purified polypeptide has laccase activity and comprises the amino acid sequence of amino acids 32-579 of SEQ ID NO: 2.

32. The method according to claim 6, wherein said purified polypeptide has laccase activity and comprises an amino acid sequence that has greater than 90% amino acid sequence identity to the amino acid sequence of SEQ ID NO: 2.

33. The method according to claim 32, wherein said purified polypeptide has laccase activity and comprises an amino acid sequence that has greater than 95% amino acid sequence identity to the amino acid sequence of SEQ ID NO: 2.

34. The method according to claim 6, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

35. The method according to claim 7, wherein said purified polypeptide comprises the amino acid sequence of SEQ ID NO: 2.

36. The method according to claim 7, wherein said purified polypeptide has laccase activity and comprises the amino acid sequence of amino acids 32-579 of SEQ ID NO: 2.

37. The method according to claim 7, wherein said purified polypeptide has laccase activity and comprises an amino acid sequence that has greater than 90% amino acid sequence identity to the amino acid sequence of SEQ ID NO: 2.

38. The method according to claim 37, wherein said purified polypeptide has laccase activity and comprises an amino acid sequence that has greater than 95% amino acid sequence identity to the amino acid sequence of SEQ ID NO: 2.

39. The method according to claim 7, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

40. The method according to claim 8, wherein said purified polypeptide comprises the amino acid sequence of SEQ ID NO: 2.

41. The method according to claim 8, wherein said purified polypeptide has laccase activity and comprises the amino acid sequence of amino acids 32-579 of SEQ ID NO: 2.

42. The method according to claim 8, wherein said purified polypeptide has laccase activity and comprises an amino acid sequence that has greater than 90% amino acid sequence identity to the amino acid sequence of SEQ ID NO: 2.

43. The method according to claim 42, wherein said purified polypeptide has laccase activity and comprises an amino acid sequence that has greater than 95% amino acid sequence identity to the amino acid sequence of SEQ ID NO: 2.

44. The method according to claim 8, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

45. The method according to claim 9, wherein said purified polypeptide comprises the amino acid sequence of SEQ ID NO: 2.

46. The method according to claim 9, wherein said purified polypeptide has laccase activity and comprises the amino acid sequence of amino acids 32-579 of SEQ ID NO: 2.

47. The method according to claim 9, wherein said purified polypeptide has laccase activity and comprises an amino acid sequence that has greater than 90% amino acid sequence identity to the amino acid sequence of SEQ ID NO: 2.

48. The method according to claim 47, wherein said purified polypeptide has laccase activity and comprises an amino acid sequence that has greater than 95% amino acid sequence identity to the amino acid sequence of SEQ ID NO: 2.

49. The method according to claim 9, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

50. The composition according to claim 2, wherein said purified polypeptide comprises the amino acid sequence of SEQ ID NO: 2.

51. The composition according to claim 2, wherein said purified polypeptide has laccase activity and comprises the amino acid sequence of amino acids 32-579 of SEQ ID NO: 2.

52. The composition according to claim 2, wherein said purified polypeptide has laccase activity and comprises an amino acid sequence that has greater than 90% amino acid sequence identity to the amino acid sequence of SEQ ID NO: 2.

53. The composition according to claim 2, wherein said purified polypeptide comprises a fragment of the amino acid sequence of SEQ ID NO: 2, the N-terminal residue of the fragment being any one of the residues 140-145 of SEQ ID NO: 2 and the C-terminal residue of the fragment being any one of the residues 524-579 of SEQ ID NO: 2 and said fragment has laccase activity.

54. The composition according to claim 2, wherein said purified polypeptide has laccase activity and comprises an amino acid sequence that has greater than 95% amino acid sequence identity to the amino acid sequence of SEQ ID NO: 2.

* * * * *

UNITED STATES PATENT AND TRADEMARK OFFICE
CERTIFICATE OF CORRECTION

PATENT NO. : 8,414,660 B2
APPLICATION NO. : 13/264165
DATED : April 9, 2013
INVENTOR(S) : Julie A. Maupin-Furlow et al.

It is certified that error appears in the above-identified patent and that said Letters Patent is hereby corrected as shown below:

In the Specification

Column 1,
Line 4, "This application" should read
 --CROSS-REFERENCE TO RELATED APPLICATIONS
  This application--.

Column 3,
Lines 10-11, "AT7 (ZP 02185070.1)," should read --AT7 (ZP_02185070.1),--.
Line 32, "(NC 008148)," should read --(NC_008148),--.
Line 40, "(NP 630785," should read --(NP_630785,--.
Lines 60-61, "SAM-032" should read --SAFR-032--.

Column 4,
Line 28, "periodical intervals" should read --periodic intervals--.
Line 60, "from HA" should read --from *Hfx*.--.

Column 10,
Line 42, "half-live" should read --half-life--.

Column 11,
Line 46, "(h), (c)," should read --(b), (c),--.
Line 47, "a genetic" should read --f) a genetic--.
Line 56, "(0, or" should read --(f), or--.

Column 20,
Line 5, "*volcanii* 1126" should read --*volcanii* H26--.

Signed and Sealed this
Twelfth Day of November, 2013

Teresa Stanek Rea
*Deputy Director of the United States Patent and Trademark Office*

Column 21,
Line 34, "SGZ activity" should read --SGZ and activity--.
Line 63, "HA volcanii" should read --*Hfx. volcanii*--.

Column 22,
Line 21, "LocA" should read --LccA--.

Column 23,
Line 15, "leels under" should read --levels under--.

Column 27,
Line 45, "0.12s$^{-1}$ ($k_{cat}$," should read --0.12s$^{-1}$ μM$^{-1}$ ($k_{cat}$,--.

Column 30,
Lines 44-45, "with 3 Uml$^1$" should read --with 3 U·ml$^{-1}$--.

Column 39,
Line 10, "Hickman," should read --Hickmann,--.

In the Claims

Column 74,
Line 54, Claim 5, "with-a the" should read --with the--.